(12) United States Patent
Naryshkina

(10) Patent No.: US 11,702,666 B2
(45) Date of Patent: *Jul. 18, 2023

(54) CELL-BASED ASSAY FOR DETERMINING ACTIVITY IN THE RETINOBLASTOMA PATHWAY

(71) Applicant: Medical Diagnostic Laboratories, LLC, Hamilton, NJ (US)

(72) Inventor: Tatyana Naryshkina, East Brunswick, NJ (US)

(73) Assignee: Medical Diagnostic Laboratories, LLC, Hamilton, NJ (US)

( * ) Notice: Subject to any disclaimer, the term of this patent is extended or adjusted under 35 U.S.C. 154(b) by 105 days.

This patent is subject to a terminal disclaimer.

(21) Appl. No.: 17/502,217

(22) Filed: Oct. 15, 2021

(65) Prior Publication Data
US 2022/0073935 A1   Mar. 10, 2022

Related U.S. Application Data

(63) Continuation of application No. 16/192,993, filed on Nov. 16, 2018, now Pat. No. 11,180,766.

(60) Provisional application No. 62/756,750, filed on Nov. 7, 2018, provisional application No. 62/587,107, filed on Nov. 16, 2017.

(51) Int. Cl.
| C12N 15/79 | (2006.01) |
| C12N 9/02  | (2006.01) |
| G01N 33/50 | (2006.01) |
| C12Q 1/48  | (2006.01) |
| C12N 9/12  | (2006.01) |

(52) U.S. Cl.
CPC .......... *C12N 15/79* (2013.01); *C12N 9/0069* (2013.01); *C12N 9/12* (2013.01); *C12Q 1/485* (2013.01); *G01N 33/5005* (2013.01); *C07K 2319/60* (2013.01); *C12Y 113/12009* (2013.01)

(58) Field of Classification Search
None
See application file for complete search history.

(56) References Cited

U.S. PATENT DOCUMENTS

2016/0216251 A1*  7/2016 Aplin ............... A61K 49/0008

* cited by examiner

*Primary Examiner* — Erin M. Bowers
(74) *Attorney, Agent, or Firm* — Arnold Braun; Jessica Dowling

(57) ABSTRACT

Disclosed are methods of determining activity of CDK4 and CDK6 variants upon exposure to CDK inhibitors, methods for determining activity of a Rb variant, methods for determining the activity of a p16 variant in a cell, and methods for determining the sensitivity of a CDK4 variant or a CDK6 variant to p16 in a cell. Stable cell lines for determining activity of CDK4 variants, CDK6 variants, Rb variants, and p16 variants are also disclosed.

3 Claims, 42 Drawing Sheets

Specification includes a Sequence Listing.

Figure 3A

ATGGTGACCGGCTACCGGCTGTTCGAGGAGATTCTC agg aat tca
agaatcttagtatcaattggtgaatcattcgggacttctgagaagttccagaaaataaatcagatggtatgtaacagcgac
cgtgtgctcaaaagaagtgctgaaggaagcaaccctcctaaaccactgtaa

Figure 3B

AAGCTT gcc acc ATG
ACGGCTTGAGGGGTTGACCCAGGACCTCCGACAGCTGCAGGAGAGCGA
GCAGCAGCTGGACCACCTGATGAATATCTGTACTACGCAGCTGCGCCT
GCTCTCCGAGGACACTGACAGCCAGCGCCTGGCCTACGTGACGTGTCA
GGACCTTCGTAGCATTGCAGACCCTGCAGAGCAGATGGTTATGGTGAT
CAAAGCCCCTCCTGAGACCCAGCTCCAAGCCGTGGACTCTTCGGAGAA
CTTTCAGATCTCCCTTAAGAGCAAACAAGGCCCGATCGATGTTTTCCTG
TGCCCTGAGGAG gggaattctgCAGAAGTGTGAGCTTCTAAAGCAA....

Figure 3C

TACCAGAAGTGT....agg aat tca
TCAGGAATGTCAGAACTTAGAGGTGGAAAGACAGAGGAGACTTGAAA
GAATAAAACAGAAACAGTCTCAACTTCAAGAACTTATTCTACAGCAAA
TTGCCTTCAAGAACCTGGTGCAGAGAAACCGGCATGCGGAGCAGCAGG
CCAGCCGGCCACCGCCACCCAACTCAGTCATCCACCTGCCCTTCATCAT
CGTCAACACCAGCAAGAAGACGGTCATCGACTGCAGCATCTCCAATGA
CAAATTTGAGTATCTGTTTAATTTTGACAACACATTTGAAATCCACGAT
GACATAGAAGTGCTGAAGCGGATGGGCATGGCTTGCGGGCTGGAGTCG
GGGAGCTGCTCTGCCGAAGACCTTAAAATGGCCAGAAGTCTGGTCCCC
AAGGCTCTGGAGCCATACGTGACAGAAATGGCTCAGGGAACTGTTGGA
GGCGTGTTC TAA

MLLRAQENIDRALFALKGDLKVLRRVHGLELGLRRG
FDHHNHLLCRVCNATKVLTRHVGQALAVSVLGEQAQ
LRSTDIHQVVQLLLALLQLSEVLGQPLKP

Figure 3F

GMLATSSNGSQYSGSRVETPVSYVAQECQNLEVERQ
RRLERIKQKQSQLQELILQQIAFKNLVQRNRHAEQQA
SRPPPPNSVIHLPFIIVNTSKKTVIDCSISNDKFEYLFN
FDNTFEIHDDIEVLKRMGMACGLESGCSAEDLKMA
RSLVPKALEPYVTEMAQGTVGGVF

SEQUENCE LISTING

```
<160> NUMBER OF SEQ ID NOS: 217

<210> SEQ ID NO 1
<211> LENGTH: 912
<212> TYPE: DNA
<213> ORGANISM: Homo sapiens

<400> SEQUENCE: 1
atggctacct ctcgatatga gccagtggct gaaattggtg tcggtgccta tgggacagtg      60
tacaaggccc gtgatcccca cagtggccac tttgtggccc tcaagagtgt gagagtcccc     120
aatggaggag gaggtggagg aggccttccc atcagcacag ttcgtgaggt ggctttactg     180
aggcgactgg aggcttttga gcatcccaat gttgtccggc tgatggacgt ctgtgccaca     240
tcccgaactg accgggagat caaggtaacc ctggtgtttg agcatgtaga ccaggaccta     300
aggacatatc tggacaaggc accccacca ggcttgccag ccgaaacgat caaggatctg     360
atgcgccagt ttctaagagg cctagatttc cttcatgcca attgcatcgt tcaccgagat     420
ctgaagccag agaacattct ggtgacaagt ggtggaacag tcaagctggc tgactttggc     480
ctggccagaa tctacagcta ccagatggca cttacacccg tggttgttac actctggtac     540
cgagctcccg aagttcttct gcagtccaca tatgcaacac ctgtggacat gtggagtgtt     600
ggctgtatct ttgcagagat gtttcgtcga aagcctctct tctgtggaaa ctctgaagcc     660
gaccagttgg gcaaaatctt tgacctgatt gggctgcctc cagaggatga ctggcctcga     720
gatgtatccc tgccccgtgg agcctttccc cccagagggc ccgcccagt gcagtcggtg      780 gtacctgaga tggaggagtc gggagcacag ctgctgctga aaatgctgac ttttaaccca     840
cacaagcgaa tctctgcctt tcgagctctg cagcactctt atctacataa ggatgaaggt     900
aatccggagt ga                                                         912

<210> SEQ ID NO 2
<211> LENGTH: 981
<212> TYPE: DNA
<213> ORGANISM: Homo sapiens

<400> SEQUENCE: 2
atggagaagg acggcctgtg ccgcgctgac cagcagtacg aatgcgtggc ggagatcggg      60
gagggcgcct atgggaaggt gttcaaggcc cgcgacttga gaacggagg ccgtttcgtg      120 gcgttgaagc gcgtgcgggt gcagaccggc gaggagggca tgccgctctc caccatccgc     180
```

| | |
|---|---:|
| gaggtggcgg tgctgaggca cctggagacc ttcgagcacc ccaacgtggt caggttgttt | 240 |
| gatgtgtgca cagtgtcacg aacagacaga gaaaccaaac taactttagt gtttgaacat | 300 |
| gtcgatcaag acttgaccac ttacttggat aaagttccag agcctggagt gcccactgaa | 360 |
| accataaagg atatgatgtt tcagcttctc cgaggtctgg actttcttca ttcacaccga | 420 |
| gtagtgcatc gcgatctaaa accacagaac attctggtga ccagcagcgg acaaataaaa | 480 |
| ctcgctgact tcggccttgc ccgcatctat agtttccaga tggctctaac ctcagtggtc | 540 |
| gtcacgctgt ggtacagagc acccgaagtc ttgctccagt ccagctacgc caccccgtg | 600 |
| gatctctgga gtgttggctg catatttgca gaaatgtttc gtagaaagcc tcttttcgt | 660 |
| ggaagttcag atgttgatca actaggaaaa atcttggacg tgattggact cccaggagaa | 720 |
| gaagactggc ctagagatgt tgcccttccc aggcaggctt tcattcaaa atctgcccaa | 780 |
| ccaattgaga agtttgtaac agatatcgat gaactaggca aagacctact tctgaagtgt | 840 |
| ttgacattta acccagccaa aagaatatct gcctacagtg ccctgtctca cccatacttc | 900 |
| caggacctgg aaaggtgcaa agaaaacctg gattcccacc tgccgcccag ccagaacacc | 960 |
| tcggagctga atacagcctg a | 981 |

<210> SEQ ID NO 3
<211> LENGTH: 504
<212> TYPE: DNA
<213> ORGANISM: Homo sapiens

<400> SEQUENCE: 3

| | |
|---|---:|
| atggagccgg cggcggggag cagcatggag ccttcggctg actggctggc cacggccgcg | 60 |
| gcccggggtc gggtagagga ggtgcgggcg ctgctggagg cggggcgct gcccaacgca | 120 |
| ccgaatagtt acgtcggag gccgatccag gtcatgatga tgggcagcgc ccagtggcg | 180 |
| gagctgctgc tgctccacgg cgcggagccc aactgcgccg accccgccac tctcacccga | 240 |
| cccgtgcacg acgctgcccg ggagggcttc ctggacacgc tggtggtgct gcaccgggcc | 300 |
| ggggcgcggc tggacgtgcg cgatgcctgg ggccgtctgc ccgtggacct ggctgaggag | 360 |
| ctgggccatc gcgatgtcgc acggtacctg gcgcgcggctg cgggggcac cagaggcagt | 420 |
| aaccatgccc gcatagatgc cgcggaaggt ccctcagaaa tgatcggaaa ccatttgtgg | 480 |
| gtttgtagaa gcaggcatgc gtag | 504 |

<210> SEQ ID NO 4
<211> LENGTH: 2787
<212> TYPE: DNA
<213> ORGANISM: Homo sapiens

<400> SEQUENCE: 4

| | |
|---|---:|
| atgccgccca aaccccccg aaaacggcc gccaccgccg ccgctgccgc cgcggaaccc | 60 |
| ccggcaccgc cgccgccgcc cctcctgag gaggacccag agcaggacag cggcccggag | 120 |
| gacctgcctc tcgtcaggct tgagtttgaa gaaacagaag aacctgattt tactgcatta | 180 |
| tgtcagaaat taagatacc agatcatgtc agagagagag cttggttaac ttgggagaaa | 240 |
| gtttcatctg tggatggagt attgggaggt tatattcaaa agaaaaagga actgtgggga | 300 |
| atctgtatct ttattgcagc agttgaccta gatgagatgt cgttcacttt tactgagcta | 360 |
| cagaaaaaca tagaaatcag tgtccataaa ttctttaact tactaaaaga aattgatacc | 420 |
| agtaccaaag ttgataatgc tatgtcaaga ctgttgaaga agtatgatgt attgtttgca | 480 |
| ctcttcagca aattggaaag gacatgtgaa cttatatatt tgacacaacc cagcagttcg | 540 |

```
atatctactg aaataaattc tgcattggtg ctaaaagttt cttggatcac attttttatta    600
gctaaagggg aagtattaca aatggaagat gatctggtga tttcatttca gttaatgcta    660
tgtgtccttg actattttat taaactctca cctcccatgt tgctcaaaga accatataaa    720
acagctgtta tacccattaa tggttcacct cgaacaccca ggcgaggtca gaacaggagt    780
gcacggatag caaaacaact agaaaatgat acaagaatta ttgaagttct ctgtaaagaa    840
catgaatgta atatagatga ggtgaaaaat gtttatttca aaaattttat accttttatg    900
aattctcttg gacttgtaac atctaatgga cttccagagg ttgaaaatct ttctaaacga    960
tacgaagaaa tttatcttaa aaataaagat ctagatgcaa gattattttt ggatcatgat   1020
aaaactcttc agactgattc tatagacagt tttgaaacac agagaacacc acgaaaaagt   1080
aaccttgatg aagaggtgaa tgtaattcct ccacacactc cagttaggac tgttatgaac   1140
actatccaac aattaatgat gattttaaat tcagcaagtg atcaaccttc agaaaatctg   1200
atttcctatt ttaacaactg cacagtgaat ccaaaagaaa gtatactgaa aagagtgaag   1260
gatataggat acatctttaa agagaaattt gctaaagctg tgggacaggg ttgtgtcgaa   1320
attggatcac agcgatacaa acttggagtt cgcttgtatt accgagtaat ggaatccatg   1380
cttaaatcag aagaagaacg attatccatt caaaatttta gcaaacttct gaatgacaac   1440
atttttcata tgtctttatt ggcgtgcgct cttgaggttg taatggccac atatagcaga   1500
agtacatctc agaatcttga ttctggaaca gatttgtctt tcccatggat tctgaatgtg   1560
cttaatttaa aagcctttga tttttacaaa gtgatcgaaa gttttatcaa agcagaaggc   1620
aacttgacaa gagaaatgat aaaacattta gaacgatgtg aacatcgaat catggaatcc   1680
cttgcatggc tctcagattc acctttattt gatcttatta acaatcaaa ggaccgagaa   1740
ggaccaactg atcaccttga atctgcttgt cctcttaatc ttcctctcca gaataatcac   1800
actgcagcag atatgtatct ttctcctgta agatctccaa agaaaaaagg ttcaactacg   1860
cgtgtaaatt ctactgcaaa tgcagagaca caagcaacct cagccttcca gacccagaag   1920
ccattgaaat ctacctctct ttcactgttt tataaaaag tgtatcggct agcctatctc   1980
cggctaaata cactttgtga acgccttctg tctgagcacc cagaattaga acatatcatc   2040
tggaccctt tccagcacac cctgcagaat gagtatgaac tcatgagaga caggcatttg   2100
gaccaaatta tgatgtgttc catgtatggc atatgcaaag tgaagaatat agaccttaaa   2160
ttcaaaatca ttgtaacagc atacaaggat cttcctcatg ctgttcagga gacattcaaa   2220
cgtgttttga tcaagaaga gggagtatgat tctattatag tattctataa ctcggtcttc   2280
atgcagagac tgaaaacaaa tattttgcag tatgcttcca ccaggccccc taccttgtca   2340
ccaataccctc acattcctcg aagcccttac aagtttccta gttcaccctt acggattcct   2400
ggagggaaca tctatatttc acccctgaag agtccatata aatttcaga aggtctgcca   2460
acaccaacaa aaatgactcc aagatcaaga atcttagtat caattggtga atcattcggg   2520
acttctgaga agttccagaa aataaatcag atggtatgta acagcgaccg tgtgctcaaa   2580
agaagtgctg aaggaagcaa ccctcctaaa ccactgaaaa aactacgctt tgatattgaa   2640
ggatcagatg aagcagatgg aagtaaacat ctcccaggag agtccaaatt tcagcagaaa   2700
ctggcagaaa tgacttctac tcgaacacga atgcaaaagc agaaaatgaa tgatagcatg   2760
gatacctcaa acaaggaaga gaaatga                                       2787
```

<210> SEQ ID NO 5

```
<211> LENGTH: 1314
<212> TYPE: DNA
<213> ORGANISM: Homo sapiens

<400> SEQUENCE: 5
atggccttgg ccggggcccc tgcgggcggc ccatgcgcgc cggcgctgga ggccctgctc      60
ggggccggcg cgctgcggct gctcgactcc tcgcagatcg tcatcatctc cgccgcgcag     120
gacgccagcg ccccgccggc tcccaccggc cccgcgcgc cgccgccgg ccctgcgac       180 cctgacctgc tgctcttcgc cacaccgcag gcgccccggc ccacacccag tgcgccgcgg     240
cccgcgctcg gccgcccgcc ggtgaagcgg aggctggacc tggaaactga ccatcagtac     300
ctggccgaga gcagtgggcc agctcgggc agaggccgcc atccaggaaa aggtgtgaaa     360 tccccgggg agaagtcacg ctatgagacc tcactgaatc tgaccaccaa gcgcttcctg     420
gagctgctga gccactcggc tgacggtgtc gtcgacctga actgggctgc cgaggtgctg     480
aaggtgcaga gcggcgcat ctatgacatc accaacgtcc ttgagggcat ccagctcatt     540
gccaagaagt ccaagaacca catccagtgg ctgggcagcc acaccacagt gggcgtcggc     600
ggacggcttg aggggttgac ccaggacctc cgacagctgc aggagagcga gcagcagctg     660
gaccacctga tgaatatctg tactacgcag ctgcgcctgc tctccgagga cactgacagc     720
cagcgcctgg cctacgtgac gtgtcaggac cttcgtagca ttgcagaccc tgcagagcag     780
atggttatgg tgatcaaagc ccctcctgag acccagctcc aagccgtgga ctcttcggag     840
aactttcaga tctcccttaa gagcaaacaa ggcccgatcg atgttttcct gtgccctgag     900
gagaccgtag gtgggatcag ccctgggaag accccatccc aggaggtcac ttctgaggag     960
gagaacaggg ccactgactc tgccaccata gtgtcaccac caccatcatc tcccccctca    1020
tccctcacca cagatcccag ccagtctcta ctcagcctgg agcaagaacc gctgttgtcc    1080
cggatgggca gcctgcgggc tcccgtggac gaggaccgcc tgtccccgct ggtggcggcc    1140
gactcgctcc tggagcatgt gcgggaggac ttctccggcc tcctccctga ggagttcatc    1200
agcctttccc caccccacga ggccctcgac taccacttcg gcctcgagga gggcgagggc    1260
atcagagacc tcttcgactg tgactttggg gacctcaccc ccctggattt ctga         1314

<210> SEQ ID NO 6
<211> LENGTH: 1233
<212> TYPE: DNA
<213> ORGANISM: Homo sapiens

<400> SEQUENCE: 6
atggcaaaag atgccggtct aattgaagcc aacggagaac tcaaggtctt catagaccag      60
aaccttagtc ccgggaaagg cgtggtgtcc ctcgtggccg ttcacccctc caccgtcaac     120
ccgctcggga agcagctctt gccaaaaacc tttggacagt ccaatgtcaa cattgcccag     180
caagtggtaa ttggtacgcc tcagagaccg gcagcgtcaa acaccctggt ggtaggaagc     240
ccacacaccc ccagcactca ctttgcctct cagaaccagc cttccgactc ctcaccttgg     300
tctgccggga gcgcaacag gaaaggagag aagaatggca agggcctacg gcatttctcc     360
atgaaggtct gcgagaaggt gcagaggaaa gggaccactt cctacaacga gtggcagac     420 gagctggttg cggagttcag tgctgccgac aaccacatct taccaaacga gtcagcttat     480
gaccagaaaa acataagacg gcgcgtctac gatgccttaa acgtgctaat ggccatgaac     540
atcatctcca aggagaagaa ggagatcaag tggattggtc tgcccaccaa ctcggctcag     600
gaatgtcaga acttagaggt ggaaagacag aggagacttg aaagaataaa acagaaacag     660
```

```
tctcaacttc aagaacttat tctacagcaa attgccttca agaacctggt gcagagaaac    720
cggcatgcgg agcagcaggc cagccggcca ccgccaccca actcagtcat ccacctgccc    780
ttcatcatcg tcaacaccag caagaagacg gtcatcgact gcagcatctc caatgacaaa    840
tttgagtatc tgtttaattt tgacaacaca tttgaaatcc acgatgacat agaagtgctg    900
aagcggatgg gcatggcttg cgggctggag tcggggagct gctctgccga agaccttaaa    960
atggccagaa gtctggtccc caaggctctg gagccatacg tgacagaaat ggctcaggga   1020
actgttggag gcgtgttcat cacgacggca ggttccacgt ctaacggcac aaggttctct   1080
gccagtgacc tgaccaacgg tgcagatggg atgctggcca caagctccaa tgggtctcag   1140
tacagcggct ccagggtgga gactccggtg tcctacgtcg gggaggacga cgaggaggac   1200
gatgacttca acgagaatga cgaggacgac tga                                1233

<210> SEQ ID NO 7
<211> LENGTH: 888
<212> TYPE: DNA
<213> ORGANISM: Homo sapiens

<400> SEQUENCE: 7
atggaacacc agctcctgtg ctgcgaagtg aaaccatcc gccgcgcgta ccccgatgcc      60
aacctcctca cgaccgggt gctgcgggcc atgctgaagg cggaggagac ctgcgcgccc    120
tcggtgtcct acttcaaatg tgtgcagaag aggtcctgc cgtccatgcg gaagatcgtc    180
gccacctgga tgctggaggt ctgcgaggaa cagaagtgcg aggaggaggt cttcccgctg    240
gccatgaact acctggaccg cttcctgtcg ctggagcccg tgaaaaagag ccgcctgcag    300
ctgctggggg ccacttgcat gttcgtggcc tctaagatga aggagaccat ccccctgacg    360
gccgagaagc tgtgcatcta caccgacaac tccatccggc ccgaggagct gctgcaaatg    420
gagctgctcc tggtgaacaa gctcaagtgg aacctggccg caatgacccc gcacgatttc    480
attgaacact tcctctccaa aatgccagag gcggaggaga caaacagat catccgcaaa    540 cacgcgcaga ccttcgttgc cctctgtgcc acagatgtga agttcatttc caatccgccc    600
tccatggtgg cagcggggag cgtggtgccc gcagtgcaag gctgaacct gaggagcccc    660 aacaacttcc tgtcctacta ccgcctcaca cgcttcctct ccagagtgat caagtgtgac    720
ccggactgcc tccgggcctg ccaggagcag atcgaagccc tgctggagtc aagcctgcgc    780
caggcccagc agaacatgga ccccaaggcc gccgaggagg aggaagagga ggaggaggag    840
gtggacctgg cttgcacacc caccgacgtg cgggacgtgg acatctga                 888

<210> SEQ ID NO 8
<211> LENGTH: 36
<212> TYPE: DNA
<213> ORGANISM: Homo sapiens

<400> SEQUENCE: 8
tggctagccg ccaccatggc tacctctcga tatgag                                36

<210> SEQ ID NO 9
<211> LENGTH: 32
<212> TYPE: DNA
<213> ORGANISM: Homo sapiens

<400> SEQUENCE: 9
cgagcggccg ctcactccgg attaccttca tc                                    32
```

```
<210> SEQ ID NO 10
<211> LENGTH: 36
<212> TYPE: DNA
<213> ORGANISM: Homo sapiens

<400> SEQUENCE: 10
tggctagccg ccaccatgga aaggacggc ctgtgc                                  36

<210> SEQ ID NO 11
<211> LENGTH: 29
<212> TYPE: DNA
<213> ORGANISM: Homo sapiens

<400> SEQUENCE: 11
gactcgagtc aggctgtatt cagctccga                                         29

<210> SEQ ID NO 12
<211> LENGTH: 36
<212> TYPE: DNA
<213> ORGANISM: Homo sapiens

<400> SEQUENCE: 12
attagctagc gccgccacca tggaacacca gctcct                                 36

<210> SEQ ID NO 13
<211> LENGTH: 30
<212> TYPE: DNA
<213> ORGANISM: Homo sapiens

<400> SEQUENCE: 13
atactcgagt cagatgtcca cgtcccgcac                                        30

<210> SEQ ID NO 14
<211> LENGTH: 37
<212> TYPE: DNA
<213> ORGANISM: Homo sapiens

<400> SEQUENCE: 14
ctaagcttgc caccatgctc gactaccact tcggcct                                37

<210> SEQ ID NO 15
<211> LENGTH: 31
<212> TYPE: DNA
<213> ORGANISM: Homo sapiens

<400> SEQUENCE: 15
cagaattccc ctcctcaggg cacaggaaaa c                                      31

<210> SEQ ID NO 16
<211> LENGTH: 38
<212> TYPE: DNA
<213> ORGANISM: Homo sapiens

<400> SEQUENCE: 16
ctaagcttgc caccatgtat gcttccacca ggcccct                                38

<210> SEQ ID NO 17
<211> LENGTH: 37
<212> TYPE: DNA
<213> ORGANISM: Homo sapiens

<400> SEQUENCE: 17
cagaattccc tttctcttcc ttgtttgagg tatccat                                37
```

<210> SEQ ID NO 18
<211> LENGTH: 41
<212> TYPE: DNA
<213> ORGANISM: Homo sapiens

<400> SEQUENCE: 18
ctaagcttgc caccatggct caggaatgtc agaacttaga g         41

<210> SEQ ID NO 19
<211> LENGTH: 31
<212> TYPE: DNA
<213> ORGANISM: Homo sapiens

<400> SEQUENCE: 19
cagaattccc tgccgtcgtg atgaacacgc c                    31

<210> SEQ ID NO 20
<211> LENGTH: 29
<212> TYPE: DNA
<213> ORGANISM: Homo sapiens

<400> SEQUENCE: 20
aggaattcac tcgactacca cttcggcct                       29

<210> SEQ ID NO 21
<211> LENGTH: 32
<212> TYPE: DNA
<213> ORGANISM: Homo sapiens

<400> SEQUENCE: 21
actctagatt actcctcagg gcacaggaaa ac                   32

<210> SEQ ID NO 22
<211> LENGTH: 30
<212> TYPE: DNA
<213> ORGANISM: Homo sapiens

<400> SEQUENCE: 22
aggaattcat atgcttccac caggccccct                      30

<210> SEQ ID NO 23
<211> LENGTH: 38
<212> TYPE: DNA
<213> ORGANISM: Homo sapiens

<400> SEQUENCE: 23
actctagatt atttctcttc cttgtttgag gtatccat              38

<210> SEQ ID NO 24
<211> LENGTH: 33
<212> TYPE: DNA
<213> ORGANISM: Homo sapiens

<400> SEQUENCE: 24
aggaattcag ctcaggaatg tcagaactta gag                  33

<210> SEQ ID NO 25
<211> LENGTH: 32
<212> TYPE: DNA
<213> ORGANISM: Homo sapiens

<400> SEQUENCE: 25

```
actctagatt atgccgtcgt gatgaacacg cc                                    32

<210> SEQ ID NO 26
<211> LENGTH: 20
<212> TYPE: DNA
<213> ORGANISM: Homo sapiens

<400> SEQUENCE: 26
atgcaaggca tgtgtcatgt                                                  20

<210> SEQ ID NO 27
<211> LENGTH: 20
<212> TYPE: DNA
<213> ORGANISM: Homo sapiens

<400> SEQUENCE: 27
ttgttgctgc aggctcatac                                                  20

<210> SEQ ID NO 28
<211> LENGTH: 20
<212> TYPE: DNA
<213> ORGANISM: Homo sapiens

<400> SEQUENCE: 28
gcaagagttc aagaccagcc                                                  20

<210> SEQ ID NO 29
<211> LENGTH: 20
<212> TYPE: DNA
<213> ORGANISM: Homo sapiens

<400> SEQUENCE: 29
tatgggaagg tgttcaaggc                                                  20

<210> SEQ ID NO 30
<211> LENGTH: 20
<212> TYPE: DNA
<213> ORGANISM: Homo sapiens

<400> SEQUENCE: 30
tgcacagtgt cacgaacaga                                                  20

<210> SEQ ID NO 31
<211> LENGTH: 20
<212> TYPE: DNA
<213> ORGANISM: Homo sapiens

<400> SEQUENCE: 31
ctgtgcctgg attacccact                                                  20

<210> SEQ ID NO 32
<211> LENGTH: 33
<212> TYPE: DNA
<213> ORGANISM: Homo sapiens

<400> SEQUENCE: 32
tatgggacag tgtacatggc ccgtgatccc cac                                   33

<210> SEQ ID NO 33
<211> LENGTH: 33
<212> TYPE: DNA
<213> ORGANISM: Homo sapiens

<400> SEQUENCE: 33
```

```
gtggggatca cgggccatgt acactgtccc ata                              33

<210> SEQ ID NO 34
<211> LENGTH: 39
<212> TYPE: DNA
<213> ORGANISM: Homo sapiens

<400> SEQUENCE: 34
gcctatggga cagtgtacgc ggcccgtgat ccccacagt                        39

<210> SEQ ID NO 35
<211> LENGTH: 39
<212> TYPE: DNA
<213> ORGANISM: Homo sapiens

<400> SEQUENCE: 35
actgtgggga tcacgggccg cgtacactgt cccataggc                        39

<210> SEQ ID NO 36
<211> LENGTH: 33
<212> TYPE: DNA
<213> ORGANISM: Homo sapiens

<400> SEQUENCE: 36
acagtgtaca aggcctgtga tccccacagt ggc                              33

<210> SEQ ID NO 37
<211> LENGTH: 33
<212> TYPE: DNA
<213> ORGANISM: Homo sapiens

<400> SEQUENCE: 37
gccactgtgg ggatcacagg ccttgtacac tgt                              33

<210> SEQ ID NO 38
<211> LENGTH: 39
<212> TYPE: DNA
<213> ORGANISM: Homo sapiens

<400> SEQUENCE: 38
gcctatggga cagtgtacaa ggccgcggat ccccacagt                        39

<210> SEQ ID NO 39
<211> LENGTH: 33
<212> TYPE: DNA
<213> ORGANISM: Homo sapiens

<400> SEQUENCE: 39
tatgggacag tgtacatggc ccgtgatccc cac                              33

<210> SEQ ID NO 40
<211> LENGTH: 39
<212> TYPE: DNA
<213> ORGANISM: Homo sapiens

<400> SEQUENCE: 40
ggccactttg tggccctcat gagtgtgaga gtccccaat                        39

<210> SEQ ID NO 41
<211> LENGTH: 39
<212> TYPE: DNA
<213> ORGANISM: Homo sapiens
```

<400> SEQUENCE: 41
attggggact ctcacactca tgagggccac aaagtggcc                           39

<210> SEQ ID NO 42
<211> LENGTH: 39
<212> TYPE: DNA
<213> ORGANISM: Homo sapiens

<400> SEQUENCE: 42
ggccactttg tggccctcag gagtgtgaga gtccccaat                           39

<210> SEQ ID NO 43
<211> LENGTH: 39
<212> TYPE: DNA
<213> ORGANISM: Homo sapiens

<400> SEQUENCE: 43
attggggact ctcacactcc tgagggccac aaagtggcc                           39

<210> SEQ ID NO 44
<211> LENGTH: 39
<212> TYPE: DNA
<213> ORGANISM: Homo sapiens

<400> SEQUENCE: 44
acaagtggtg gaacagtcca gctggctgac tttggcctg                           39

<210> SEQ ID NO 45
<211> LENGTH: 39
<212> TYPE: DNA
<213> ORGANISM: Homo sapiens

<400> SEQUENCE: 45
caggccaaag tcagccagct ggactgttcc accacttgt                           39

<210> SEQ ID NO 46
<211> LENGTH: 45
<212> TYPE: DNA
<213> ORGANISM: Homo sapiens

<400> SEQUENCE: 46
gtagattctg gccaggccaa accgagccag cttgactgtt ccacc                    45

<210> SEQ ID NO 47
<211> LENGTH: 45
<212> TYPE: DNA
<213> ORGANISM: Homo sapiens

<400> SEQUENCE: 47
ggtggaacag tcaagctggc tcggtttggc ctggccagaa tctac                    45

<210> SEQ ID NO 48
<211> LENGTH: 39
<212> TYPE: DNA
<213> ORGANISM: Homo sapiens

<400> SEQUENCE: 48
ggaacagtca agctggctca gtttggcctg gccagaatc                           39

<210> SEQ ID NO 49
<211> LENGTH: 39
<212> TYPE: DNA
<213> ORGANISM: Homo sapiens

<400> SEQUENCE: 49
gattctggcc aggccaaact gagccagctt gactgttcc                                  39

<210> SEQ ID NO 50
<211> LENGTH: 39
<212> TYPE: DNA
<213> ORGANISM: Homo sapiens

<400> SEQUENCE: 50
ggaacagtca agctggctgc ctttggcctg gccagaatc                                  39

<210> SEQ ID NO 51
<211> LENGTH: 39
<212> TYPE: DNA
<213> ORGANISM: Homo sapiens

<400> SEQUENCE: 51
gattctggcc aggccaaagg cagccagctt gactgttcc                                  39

<210> SEQ ID NO 52
<211> LENGTH: 39
<212> TYPE: DNA
<213> ORGANISM: Homo sapiens

<400> SEQUENCE: 52
ggaacagtca agctggctga ttttggcctg gccagaatc                                  39

<210> SEQ ID NO 53
<211> LENGTH: 39
<212> TYPE: DNA
<213> ORGANISM: Homo sapiens

<400> SEQUENCE: 53
gattctggcc aggccaaaat cagccagctt gactgttcc                                  39

<210> SEQ ID NO 54
<211> LENGTH: 39
<212> TYPE: DNA
<213> ORGANISM: Homo sapiens

<400> SEQUENCE: 54
ggaacagtca agctggctta ctttggcctg gccagaatc                                  39

<210> SEQ ID NO 55
<211> LENGTH: 39
<212> TYPE: DNA
<213> ORGANISM: Homo sapiens

<400> SEQUENCE: 55
gattctggcc aggccaaagt aagccagctt gactgttcc                                  39

<210> SEQ ID NO 56
<211> LENGTH: 39
<212> TYPE: DNA
<213> ORGANISM: Homo sapiens

<400> SEQUENCE: 56
ggaacagtca agctggctta ctttggcctg gccagaatc                                  39

<210> SEQ ID NO 57
<211> LENGTH: 39
<212> TYPE: DNA

<213> ORGANISM: Homo sapiens

<400> SEQUENCE: 57
gattctggcc aggccaaagt aagccagctt gactgttcc          39

<210> SEQ ID NO 58
<211> LENGTH: 33
<212> TYPE: DNA
<213> ORGANISM: Homo sapiens

<400> SEQUENCE: 58
ccacacaagc gaatctgtgc ctttcgagct ctg                33

<210> SEQ ID NO 59
<211> LENGTH: 33
<212> TYPE: DNA
<213> ORGANISM: Homo sapiens

<400> SEQUENCE: 59
cagagctcga aaggcacaga ttcgcttgtg tgg                33

<210> SEQ ID NO 60
<211> LENGTH: 39
<212> TYPE: DNA
<213> ORGANISM: Homo sapiens

<400> SEQUENCE: 60
aagctggctg actttggctt ggccagaatc tacagctac          39

<210> SEQ ID NO 61
<211> LENGTH: 39
<212> TYPE: DNA
<213> ORGANISM: Homo sapiens

<400> SEQUENCE: 61
gtagctgtag attctggcca agccaaagtc agccagctt          39

<210> SEQ ID NO 62
<211> LENGTH: 39
<212> TYPE: DNA
<213> ORGANISM: Homo sapiens

<400> SEQUENCE: 62
cttcatgcca attgcatcat tcaccgagat ctgaagcca          39

<210> SEQ ID NO 63
<211> LENGTH: 39
<212> TYPE: DNA
<213> ORGANISM: Homo sapiens

<400> SEQUENCE: 63
tggcttcaga tctcggtgaa tgatgcaatt ggcatgaag          39

<210> SEQ ID NO 64
<211> LENGTH: 39
<212> TYPE: DNA
<213> ORGANISM: Homo sapiens

<400> SEQUENCE: 64
cagatggcac ttacacccat ggttgttaca ctctggtac          39

<210> SEQ ID NO 65
<211> LENGTH: 39

<212> TYPE: DNA
<213> ORGANISM: Homo sapiens

<400> SEQUENCE: 65
gtaccagagt gtaacaacca tgggtgtaag tgccatctg          39

<210> SEQ ID NO 66
<211> LENGTH: 39
<212> TYPE: DNA
<213> ORGANISM: Homo sapiens

<400> SEQUENCE: 66
cagatggcac ttacacccgg ggttgttaca ctctggtac          39

<210> SEQ ID NO 67
<211> LENGTH: 39
<212> TYPE: DNA
<213> ORGANISM: Homo sapiens

<400> SEQUENCE: 67
gtaccagagt gtaacaaccc cgggtgtaag tgccatctg          39

<210> SEQ ID NO 68
<211> LENGTH: 39
<212> TYPE: DNA
<213> ORGANISM: Homo sapiens

<400> SEQUENCE: 68
gggaaggtgt tcaaggcctg cgacttgaag aacggaggc          39

<210> SEQ ID NO 69
<211> LENGTH: 39
<212> TYPE: DNA
<213> ORGANISM: Homo sapiens

<400> SEQUENCE: 69
gcctccgttc ttcaagtcgc aggccttgaa caccttccc          39

<210> SEQ ID NO 70
<211> LENGTH: 39
<212> TYPE: DNA
<213> ORGANISM: Homo sapiens

<400> SEQUENCE: 70
ggccgtttcg tggcgttgat gcgcgtgcgg gtgcagacc          39

<210> SEQ ID NO 71
<211> LENGTH: 39
<212> TYPE: DNA
<213> ORGANISM: Homo sapiens

<400> SEQUENCE: 71
ggtctgcacc cgcacgcgca tcaacgccac gaaacggcc          39

<210> SEQ ID NO 72
<211> LENGTH: 33
<212> TYPE: DNA
<213> ORGANISM: Homo sapiens

<400> SEQUENCE: 72
caccgagtag tgcatcacga tctaaaacca cag          33

<210> SEQ ID NO 73

-continued

```
<211> LENGTH: 33
<212> TYPE: DNA
<213> ORGANISM: Homo sapiens

<400> SEQUENCE: 73
ctgtggtttt agatcgtgat gcactactcg gtg                              33

<210> SEQ ID NO 74
<211> LENGTH: 39
<212> TYPE: DNA
<213> ORGANISM: Homo sapiens

<400> SEQUENCE: 74
ggacaaataa aactcgctaa cttcggcctt gcccgcatc                        39

<210> SEQ ID NO 75
<211> LENGTH: 39
<212> TYPE: DNA
<213> ORGANISM: Homo sapiens

<400> SEQUENCE: 75
gatgcgggca aggccgaagt tagcgagttt tatttgtcc                        39

<210> SEQ ID NO 76
<211> LENGTH: 33
<212> TYPE: DNA
<213> ORGANISM: Homo sapiens

<400> SEQUENCE: 76
tccagctacg ccaccctcgt ggatctctgg agt                              33

<210> SEQ ID NO 77
<211> LENGTH: 33
<212> TYPE: DNA
<213> ORGANISM: Homo sapiens

<400> SEQUENCE: 77
actccagaga tccacgaggg tggcgtagct gga                              33

<210> SEQ ID NO 78
<211> LENGTH: 39
<212> TYPE: DNA
<213> ORGANISM: Homo sapiens

<400> SEQUENCE: 78
cgtagaaagc ctctttttg tggaagttca gatgttgat                         39

<210> SEQ ID NO 79
<211> LENGTH: 39
<212> TYPE: DNA
<213> ORGANISM: Homo sapiens

<400> SEQUENCE: 79
atcaacatct gaacttccac aaaaaagagg ctttctacg                        39

<210> SEQ ID NO 80
<211> LENGTH: 39
<212> TYPE: DNA
<213> ORGANISM: Homo sapiens

<400> SEQUENCE: 80
cgtagaaagc ctctttttag tggaagttca gatgttgat                        39
```

<210> SEQ ID NO 81
<211> LENGTH: 39
<212> TYPE: DNA
<213> ORGANISM: Homo sapiens

<400> SEQUENCE: 81
atcaacatct gaacttccac taaaaagagg ctttctacg                                   39

<210> SEQ ID NO 82
<211> LENGTH: 42
<212> TYPE: DNA
<213> ORGANISM: Homo sapiens

<400> SEQUENCE: 82
ctggctgact ttggcctggt cagaatctac agctaccaga tg                              42

<210> SEQ ID NO 83
<211> LENGTH: 42
<212> TYPE: DNA
<213> ORGANISM: Homo sapiens

<400> SEQUENCE: 83
catctggtag ctgtagattc tgaccaggcc aaagtcagcc ag                              42

<210> SEQ ID NO 84
<211> LENGTH: 39
<212> TYPE: DNA
<213> ORGANISM: Homo sapiens

<400> SEQUENCE: 84
ggtggaggag gccttccctt cagcacagtt cgtgaggtg                                   39

<210> SEQ ID NO 85
<211> LENGTH: 39
<212> TYPE: DNA
<213> ORGANISM: Homo sapiens

<400> SEQUENCE: 85
cacctcacga actgtgctga agggaaggcc tcctccacc                                   39

<210> SEQ ID NO 86
<211> LENGTH: 39
<212> TYPE: DNA
<213> ORGANISM: Homo sapiens

<400> SEQUENCE: 86
gtagaccagg acctaaggaa atatctggac aaggcaccc                                   39

<210> SEQ ID NO 87
<211> LENGTH: 39
<212> TYPE: DNA
<213> ORGANISM: Homo sapiens

<400> SEQUENCE: 87
gggtgccttg tccagatatt tccttaggtc ctggtctac                                   39

<210> SEQ ID NO 88
<211> LENGTH: 42
<212> TYPE: DNA
<213> ORGANISM: Homo sapiens

<400> SEQUENCE: 88
catgtagacc aggacctaag gagatatctg gacaaggcac cc                              42

```
<210> SEQ ID NO 89
<211> LENGTH: 42
<212> TYPE: DNA
<213> ORGANISM: Homo sapiens

<400> SEQUENCE: 89
gggtgccttg tccagatatc tccttaggtc ctggtctaca tg              42

<210> SEQ ID NO 90
<211> LENGTH: 39
<212> TYPE: DNA
<213> ORGANISM: Homo sapiens

<400> SEQUENCE: 90
ggaggaggtg gaggaggccg tcccatcagc acagttcgt                  39

<210> SEQ ID NO 91
<211> LENGTH: 39
<212> TYPE: DNA
<213> ORGANISM: Homo sapiens

<400> SEQUENCE: 91
acgaactgtg ctgatgggac ggcctcctcc acctcctcc                  39

<210> SEQ ID NO 92
<211> LENGTH: 45
<212> TYPE: DNA
<213> ORGANISM: Homo sapiens

<400> SEQUENCE: 92
tctcgatatg agccagtggc tgaacttggt gtcggtgcct atggg           45

<210> SEQ ID NO 93
<211> LENGTH: 45
<212> TYPE: DNA
<213> ORGANISM: Homo sapiens

<400> SEQUENCE: 93
cccataggca ccgacaccaa gttcagccac tggctcatat cgaga           45

<210> SEQ ID NO 94
<211> LENGTH: 39
<212> TYPE: DNA
<213> ORGANISM: Homo sapiens

<400> SEQUENCE: 94
attggtgtcg gtgcctatgc gacagtgtac aaggcccgt                  39

<210> SEQ ID NO 95
<211> LENGTH: 39
<212> TYPE: DNA
<213> ORGANISM: Homo sapiens

<400> SEQUENCE: 95
acgggccttg tacactgtcg cataggcacc gacaccaat                  39

<210> SEQ ID NO 96
<211> LENGTH: 39
<212> TYPE: DNA
<213> ORGANISM: Homo sapiens

<400> SEQUENCE: 96
cacagtggcc actttgtgtc cctcaagagt gtgagagtc                  39
```

<210> SEQ ID NO 97
<211> LENGTH: 39
<212> TYPE: DNA
<213> ORGANISM: Homo sapiens

<400> SEQUENCE: 97
gactctcaca ctcttgaggg acacaaagtg gccactgtg                                  39

<210> SEQ ID NO 98
<211> LENGTH: 39
<212> TYPE: DNA
<213> ORGANISM: Homo sapiens

<400> SEQUENCE: 98
atcaaggtaa ccctggtgat tgagcatgta gaccaggac                                  39

<210> SEQ ID NO 99
<211> LENGTH: 39
<212> TYPE: DNA
<213> ORGANISM: Homo sapiens

<400> SEQUENCE: 99
gtcctggtct acatgctcaa tcaccagggt taccttgat                                  39

<210> SEQ ID NO 100
<211> LENGTH: 39
<212> TYPE: DNA
<213> ORGANISM: Homo sapiens

<400> SEQUENCE: 100
ggtggaacag tcaagctgtc tgactttggc ctggccaga                                  39

<210> SEQ ID NO 101
<211> LENGTH: 39
<212> TYPE: DNA
<213> ORGANISM: Homo sapiens

<400> SEQUENCE: 101
tctggccagg ccaaagtcag acagcttgac tgttccacc                                  39

<210> SEQ ID NO 102
<211> LENGTH: 39
<212> TYPE: DNA
<213> ORGANISM: Homo sapiens

<400> SEQUENCE: 102
agcggacaaa taaaactcgt tgacttcggc cttgcccgc                                  39

<210> SEQ ID NO 103
<211> LENGTH: 39
<212> TYPE: DNA
<213> ORGANISM: Homo sapiens

<400> SEQUENCE: 103
gcgggcaagg ccgaagtcaa cgagttttat ttgtccgct                                  39

<210> SEQ ID NO 104
<211> LENGTH: 39
<212> TYPE: DNA
<213> ORGANISM: Homo sapiens

<400> SEQUENCE: 104
ctaaaaccac agaacattgt ggtgaccagc agcggacaa            39

<210> SEQ ID NO 105
<211> LENGTH: 39
<212> TYPE: DNA
<213> ORGANISM: Homo sapiens

<400> SEQUENCE: 105
ttgtccgctg ctggtcacca caatgttctg tggttttag            39

<210> SEQ ID NO 106
<211> LENGTH: 39
<212> TYPE: DNA
<213> ORGANISM: Homo sapiens

<400> SEQUENCE: 106
gtcgatcaag acttgaccaa atacttggat aaagttcca            39

<210> SEQ ID NO 107
<211> LENGTH: 39
<212> TYPE: DNA
<213> ORGANISM: Homo sapiens

<400> SEQUENCE: 107
tggaacttta tccaagtatt tggtcaagtc ttgatcgac            39

<210> SEQ ID NO 108
<211> LENGTH: 39
<212> TYPE: DNA
<213> ORGANISM: Homo sapiens

<400> SEQUENCE: 108
tttgaacatg tcgatcaaaa cttgaccact tacttggat            39

<210> SEQ ID NO 109
<211> LENGTH: 39
<212> TYPE: DNA
<213> ORGANISM: Homo sapiens

<400> SEQUENCE: 109
atccaagtaa gtggtcaagt tttgatcgac atgttcaaa            39

<210> SEQ ID NO 110
<211> LENGTH: 39
<212> TYPE: DNA
<213> ORGANISM: Homo sapiens

<400> SEQUENCE: 110
ctaactttag tgtttgaata tgtcgatcaa gacttgacc            39

<210> SEQ ID NO 111
<211> LENGTH: 39
<212> TYPE: DNA
<213> ORGANISM: Homo sapiens

<400> SEQUENCE: 111
ggtcaagtct tgatcgacat attcaaacac taaagttag            39

<210> SEQ ID NO 112
<211> LENGTH: 39
<212> TYPE: DNA
<213> ORGANISM: Homo sapiens

<400> SEQUENCE: 112
accaaactaa ctttagtgat tgaacatgtc gatcaagac                                    39

<210> SEQ ID NO 113
<211> LENGTH: 39
<212> TYPE: DNA
<213> ORGANISM: Homo sapiens

<400> SEQUENCE: 113
gtcttgatcg acatgttcaa tcactaaagt tagtttggt                                    39

<210> SEQ ID NO 114
<211> LENGTH: 39
<212> TYPE: DNA
<213> ORGANISM: Homo sapiens

<400> SEQUENCE: 114
aacggaggcc gtttcgtggt gttgaagcgc gtgcgggtg                                    39

<210> SEQ ID NO 115
<211> LENGTH: 39
<212> TYPE: DNA
<213> ORGANISM: Homo sapiens

<400> SEQUENCE: 115
cacccgcacg cgcttcaaca ccacgaaacg gcctccgtt                                    39

<210> SEQ ID NO 116
<211> LENGTH: 39
<212> TYPE: DNA
<213> ORGANISM: Homo sapiens

<400> SEQUENCE: 116
gagggcgcct atgggaaggc gttcaaggcc cgcgacttg                                    39

<210> SEQ ID NO 117
<211> LENGTH: 39
<212> TYPE: DNA
<213> ORGANISM: Homo sapiens

<400> SEQUENCE: 117
caagtcgcgg gccttgaacg ccttcccata ggcgccctc                                    39

<210> SEQ ID NO 118
<211> LENGTH: 39
<212> TYPE: DNA
<213> ORGANISM: Homo sapiens

<400> SEQUENCE: 118
tacgaatgcg tggcggagct cggggagggc gcctatggg                                    39

<210> SEQ ID NO 119
<211> LENGTH: 39
<212> TYPE: DNA
<213> ORGANISM: Homo sapiens

<400> SEQUENCE: 119
cccataggcg ccctccccga gctccgccac gcattcgta                                    39

<210> SEQ ID NO 120
<211> LENGTH: 34
<212> TYPE: DNA
<213> ORGANISM: Homo sapiens

```
<400> SEQUENCE: 120
taatggatcc gccgccacca tgccgcccaa aacc                                    34

<210> SEQ ID NO 121
<211> LENGTH: 33
<212> TYPE: DNA
<213> ORGANISM: Homo sapiens

<400> SEQUENCE: 121
gcggctcgag tcatttctct tccttgtttg agg                                     33

<210> SEQ ID NO 122
<211> LENGTH: 39
<212> TYPE: DNA
<213> ORGANISM: Homo sapiens

<400> SEQUENCE: 122
tggctagccg ccaccatggc aaaagatgcc ggtctaatt                               39

<210> SEQ ID NO 123
<211> LENGTH: 29
<212> TYPE: DNA
<213> ORGANISM: Homo sapiens

<400> SEQUENCE: 123
gactcgagtc agtcgtcctc gtcattctc                                          29

<210> SEQ ID NO 124
<211> LENGTH: 37
<212> TYPE: DNA
<213> ORGANISM: Homo sapiens

<400> SEQUENCE: 124
ctaagcttgc caccatgctc gactaccact tcggcct                                 37

<210> SEQ ID NO 125
<211> LENGTH: 31
<212> TYPE: DNA
<213> ORGANISM: Homo sapiens

<400> SEQUENCE: 125
cagaattccc ctcctcaggg cacaggaaaa c                                       31

<210> SEQ ID NO 126
<211> LENGTH: 38
<212> TYPE: DNA
<213> ORGANISM: Homo sapiens

<400> SEQUENCE: 126
ctaagcttgc caccatgtat gcttccacca ggcccct                                 38

<210> SEQ ID NO 127
<211> LENGTH: 37
<212> TYPE: DNA
<213> ORGANISM: Homo sapiens

<400> SEQUENCE: 127
cagaattccc tttctcttcc ttgtttgagg tatccat                                 37

<210> SEQ ID NO 128
<211> LENGTH: 29
<212> TYPE: DNA
<213> ORGANISM: Homo sapiens
```

<400> SEQUENCE: 128
aattcactag gcgactacca cttcggcct                                    29

<210> SEQ ID NO 129
<211> LENGTH: 32
<212> TYPE: DNA
<213> ORGANISM: Homo sapiens

<400> SEQUENCE: 129
actctagatt actcctcagg gcacaggaaa ac                                32

<210> SEQ ID NO 130
<211> LENGTH: 30
<212> TYPE: DNA
<213> ORGANISM: Homo sapiens

<400> SEQUENCE: 130
aggaattcat atgcttccac caggccccct                                   30

<210> SEQ ID NO 131
<211> LENGTH: 38
<212> TYPE: DNA
<213> ORGANISM: Homo sapiens

<400> SEQUENCE: 131
actctagatt atttctcttc cttgtttgag gtatccat                          38

<210> SEQ ID NO 132
<211> LENGTH: 39
<212> TYPE: DNA
<213> ORGANISM: Homo sapiens

<400> SEQUENCE: 132
tatcggctag cctatctctg gctaaataca ctttgtgaa                         39

<210> SEQ ID NO 133
<211> LENGTH: 39
<212> TYPE: DNA
<213> ORGANISM: Homo sapiens

<400> SEQUENCE: 133
ttcacaaagt gtatttagcc agagataggc tagccgata                         39

<210> SEQ ID NO 134
<211> LENGTH: 39
<212> TYPE: DNA
<213> ORGANISM: Homo sapiens

<400> SEQUENCE: 134
ttggaccaaa ttatgatgtt ttccatgtat ggcatatgc                         39

<210> SEQ ID NO 135
<211> LENGTH: 39
<212> TYPE: DNA
<213> ORGANISM: Homo sapiens

<400> SEQUENCE: 135
gcatatgcca tacatggaaa acatcataat ttggtccaa                         39

<210> SEQ ID NO 136
<211> LENGTH: 40
<212> TYPE: DNA

<213> ORGANISM: Homo sapiens

<400> SEQUENCE: 136
gtgggacagg gttgtgtcaa aattggatca cagcgataca                    40

<210> SEQ ID NO 137
<211> LENGTH: 40
<212> TYPE: DNA
<213> ORGANISM: Homo sapiens

<400> SEQUENCE: 137
tgtatcgctg tgatccaatt ttgacacaac cctgtcccac                    40

<210> SEQ ID NO 138
<211> LENGTH: 40
<212> TYPE: DNA
<213> ORGANISM: Homo sapiens

<400> SEQUENCE: 138
ttcatatgtc tttattggtg tgcgctcttg aggttgtaat                    40

<210> SEQ ID NO 139
<211> LENGTH: 40
<212> TYPE: DNA
<213> ORGANISM: Homo sapiens

<400> SEQUENCE: 139
attacaacct caagagcgca caccaataaa gacatatgaa                    40

<210> SEQ ID NO 140
<211> LENGTH: 39
<212> TYPE: DNA
<213> ORGANISM: Homo sapiens

<400> SEQUENCE: 140
ttttataaaa aagtgtattg gctagcctat ctccggcta                     39

<210> SEQ ID NO 141
<211> LENGTH: 39
<212> TYPE: DNA
<213> ORGANISM: Homo sapiens

<400> SEQUENCE: 141
tagccggaga taggctagcc aatacacttt tttataaaa                     39

<210> SEQ ID NO 142
<211> LENGTH: 41
<212> TYPE: DNA
<213> ORGANISM: Homo sapiens

<400> SEQUENCE: 142 gaaaaaggt tcaactacga gtgtaaattc tactgcaaat g                   41

<210> SEQ ID NO 143
<211> LENGTH: 41
<212> TYPE: DNA
<213> ORGANISM: Homo sapiens

<400> SEQUENCE: 143
catttgcagt agaatttaca ctcgtagttg aaccttttt c                   41

<210> SEQ ID NO 144
<211> LENGTH: 39

```
<212> TYPE: DNA
<213> ORGANISM: Homo sapiens

<400> SEQUENCE: 144
tcactgtttt ataaaaaaat gtatcggcta gcctatctc                              39

<210> SEQ ID NO 145
<211> LENGTH: 39
<212> TYPE: DNA
<213> ORGANISM: Homo sapiens

<400> SEQUENCE: 145
gagataggct agccgataca tttttttata aaacagtga                              39

<210> SEQ ID NO 146
<211> LENGTH: 39
<212> TYPE: DNA
<213> ORGANISM: Homo sapiens

<400> SEQUENCE: 146
atctccggct aaatacacgt tgtgaacgcc ttctgtctg                              39

<210> SEQ ID NO 147
<211> LENGTH: 39
<212> TYPE: DNA
<213> ORGANISM: Homo sapiens

<400> SEQUENCE: 147
cagacagaag gcgttcacaa cgtgtattta gccggagat                              39

<210> SEQ ID NO 148
<211> LENGTH: 39
<212> TYPE: DNA
<213> ORGANISM: Homo sapiens

<400> SEQUENCE: 148
ttcctagttc acccttacag attcctggag ggaacatct                              39

<210> SEQ ID NO 149
<211> LENGTH: 39
<212> TYPE: DNA
<213> ORGANISM: Homo sapiens

<400> SEQUENCE: 149
agatgttccc tccaggaatc tgtaagggtg aactaggaa                              39

<210> SEQ ID NO 150
<211> LENGTH: 39
<212> TYPE: DNA
<213> ORGANISM: Homo sapiens

<400> SEQUENCE: 150
cagaattaga acatatcacc tggacccttt tccagcaca                              39

<210> SEQ ID NO 151
<211> LENGTH: 39
<212> TYPE: DNA
<213> ORGANISM: Homo sapiens

<400> SEQUENCE: 151
tgtgctggaa aagggtccag gtgatatgtt ctaattctg                              39

<210> SEQ ID NO 152
```

```
<211> LENGTH: 39
<212> TYPE: DNA
<213> ORGANISM: Homo sapiens

<400> SEQUENCE: 152
tatgaactca tgagagactg gcatttggac caaattatg                                  39

<210> SEQ ID NO 153
<211> LENGTH: 39
<212> TYPE: DNA
<213> ORGANISM: Homo sapiens

<400> SEQUENCE: 153
cataatttgg tccaaatgcc agtctctcat gagttcata                                  39

<210> SEQ ID NO 154
<211> LENGTH: 39
<212> TYPE: DNA
<213> ORGANISM: Homo sapiens

<400> SEQUENCE: 154
accttaaatt caaaatcaat gtaacagcat acaaggatc                                  39

<210> SEQ ID NO 155
<211> LENGTH: 39
<212> TYPE: DNA
<213> ORGANISM: Homo sapiens

<400> SEQUENCE: 155
gatccttgta tgctgttaca ttgattttga atttaaggt                                  39

<210> SEQ ID NO 156
<211> LENGTH: 39
<212> TYPE: DNA
<213> ORGANISM: Homo sapiens

<400> SEQUENCE: 156
ttcctagttc acccttacag attcctggag ggaacatct                                  39

<210> SEQ ID NO 157
<211> LENGTH: 39
<212> TYPE: DNA
<213> ORGANISM: Homo sapiens

<400> SEQUENCE: 157
agatgttccc tccaggaatc tgtaagggtg aactaggaa                                  39

<210> SEQ ID NO 158
<211> LENGTH: 41
<212> TYPE: DNA
<213> ORGANISM: Homo sapiens

<400> SEQUENCE: 158
gagacaggca tttggaccaa acattcaaac gtgttttgat c                               41

<210> SEQ ID NO 159
<211> LENGTH: 41
<212> TYPE: DNA
<213> ORGANISM: Homo sapiens

<400> SEQUENCE: 159
gatcaaaaca cgtttgaatg tttggtccaa atgcctgtct c                               41
```

```
<210> SEQ ID NO 160
<211> LENGTH: 41
<212> TYPE: DNA
<213> ORGANISM: Homo sapiens

<400> SEQUENCE: 160
gatcaaaaca cgtttgaatg tttggtccaa atgcctgtct c              41

<210> SEQ ID NO 161
<211> LENGTH: 39
<212> TYPE: DNA
<213> ORGANISM: Homo sapiens

<400> SEQUENCE: 161
cgttcacaaa gtgtatttag agataggcta gccgataca                 39

<210> SEQ ID NO 162
<211> LENGTH: 39
<212> TYPE: DNA
<213> ORGANISM: Homo sapiens

<400> SEQUENCE: 162
agtaccaaag ttgataatgt tatgtcaaga ctgttgaag                 39

<210> SEQ ID NO 163
<211> LENGTH: 39
<212> TYPE: DNA
<213> ORGANISM: Homo sapiens

<400> SEQUENCE: 163
cttcaacagt cttgacataa cattatcaac tttggtact                 39

<210> SEQ ID NO 164
<211> LENGTH: 39
<212> TYPE: DNA
<213> ORGANISM: Homo sapiens

<400> SEQUENCE: 164
attgatacca gtaccaaaag tgataatgct atgtcaaga                 39

<210> SEQ ID NO 165
<211> LENGTH: 39
<212> TYPE: DNA
<213> ORGANISM: Homo sapiens

<400> SEQUENCE: 165
tcttgacata gcattatcac ttttggtact ggtatcaat                 39

<210> SEQ ID NO 166
<211> LENGTH: 39
<212> TYPE: DNA
<213> ORGANISM: Homo sapiens

<400> SEQUENCE: 166
aagaaaaagg aactgtgggc aatctgtatc tttattgca                 39

<210> SEQ ID NO 167
<211> LENGTH: 39
<212> TYPE: DNA
<213> ORGANISM: Homo sapiens

<400> SEQUENCE: 167
tgcaataaag atacagattg cccacagttc cttttttctt                39
```

```
<210> SEQ ID NO 168
<211> LENGTH: 39
<212> TYPE: DNA
<213> ORGANISM: Homo sapiens

<400> SEQUENCE: 168
aagaaaaagg aactgtggag aatctgtatc tttattgca                              39

<210> SEQ ID NO 169
<211> LENGTH: 39
<212> TYPE: DNA
<213> ORGANISM: Homo sapiens

<400> SEQUENCE: 169
tgcaataaag atacagattc tccacagttc cttttctt                               39

<210> SEQ ID NO 170
<211> LENGTH: 39
<212> TYPE: DNA
<213> ORGANISM: Homo sapiens

<400> SEQUENCE: 170
atgtaattcc tccacacagc ccagttagga ctgttatga                              39

<210> SEQ ID NO 171
<211> LENGTH: 39
<212> TYPE: DNA
<213> ORGANISM: Homo sapiens

<400> SEQUENCE: 171
tcataacagt cctaactggg ctgtgtggag gaattacat                              39

<210> SEQ ID NO 172
<211> LENGTH: 39
<212> TYPE: DNA
<213> ORGANISM: Homo sapiens

<400> SEQUENCE: 172
atgtaattcc tccacacaat ccagttagga ctgttatga                              39

<210> SEQ ID NO 173
<211> LENGTH: 39
<212> TYPE: DNA
<213> ORGANISM: Homo sapiens

<400> SEQUENCE: 173
tcataacagt cctaactgga ttgtgtggag gaattacat                              39

<210> SEQ ID NO 174
<211> LENGTH: 39
<212> TYPE: DNA
<213> ORGANISM: Homo sapiens

<400> SEQUENCE: 174
gtaattcctc cacacactgc agttaggact gttatgaac                              39

<210> SEQ ID NO 175
<211> LENGTH: 39
<212> TYPE: DNA
<213> ORGANISM: Homo sapiens

<400> SEQUENCE: 175
gttcataaca gtcctaactg cagtgtgtgg aggaattac                              39
```

<210> SEQ ID NO 176
<211> LENGTH: 39
<212> TYPE: DNA
<213> ORGANISM: Homo sapiens

<400> SEQUENCE: 176
agttcgatat ctactgaaac aaattctgca ttggtgcta                              39

<210> SEQ ID NO 177
<211> LENGTH: 39
<212> TYPE: DNA
<213> ORGANISM: Homo sapiens

<400> SEQUENCE: 177
tagcaccaat gcagaatttg tttcagtaga tatcgaact                              39

<210> SEQ ID NO 178
<211> LENGTH: 39
<212> TYPE: DNA
<213> ORGANISM: Homo sapiens

<400> SEQUENCE: 178
atatctactg aaataaatac tgcattggtg ctaaaagtt                              39

<210> SEQ ID NO 179
<211> LENGTH: 39
<212> TYPE: DNA
<213> ORGANISM: Homo sapiens

<400> SEQUENCE: 179 aactttagc accaatgcag tatttatttc agtagatat                               39

<210> SEQ ID NO 180
<211> LENGTH: 39
<212> TYPE: DNA
<213> ORGANISM: Homo sapiens

<400> SEQUENCE: 180
ctttaactta ctaaaagata ttgataccag taccaaagt                              39

<210> SEQ ID NO 181
<211> LENGTH: 39
<212> TYPE: DNA
<213> ORGANISM: Homo sapiens

<400> SEQUENCE: 181
actttggtac tggtatcaat atcttttagt aagttaaag                              39

<210> SEQ ID NO 182
<211> LENGTH: 39
<212> TYPE: DNA
<213> ORGANISM: Homo sapiens

<400> SEQUENCE: 182
actctcaccc gacccgtgta cgacgctgcc cgggagggc                              39

<210> SEQ ID NO 183
<211> LENGTH: 39
<212> TYPE: DNA
<213> ORGANISM: Homo sapiens

<400> SEQUENCE: 183
gccctcccgg gcagcgtcgt acacgggtcg ggtgagagt                              39

<210> SEQ ID NO 184
<211> LENGTH: 39
<212> TYPE: DNA
<213> ORGANISM: Homo sapiens

<400> SEQUENCE: 184
atgcctgggg ccgtctgctc gtggacctgg ctgaggagc                              39

<210> SEQ ID NO 185
<211> LENGTH: 39
<212> TYPE: DNA
<213> ORGANISM: Homo sapiens

<400> SEQUENCE: 185
gctcctcagc caggtccacg agcagacggc cccaggcat                              39

<210> SEQ ID NO 186
<211> LENGTH: 39
<212> TYPE: DNA
<213> ORGANISM: Homo sapiens

<400> SEQUENCE: 186
gcgctgctgg aggcgggggg gctgcccaac gcaccgaat                              39

<210> SEQ ID NO 187
<211> LENGTH: 39
<212> TYPE: DNA
<213> ORGANISM: Homo sapiens

<400> SEQUENCE: 187
attcggtgcg ttgggcagcc ccccgcctc cagcagcgc                               39

<210> SEQ ID NO 188
<211> LENGTH: 39
<212> TYPE: DNA
<213> ORGANISM: Homo sapiens

<400> SEQUENCE: 188
gagctgggcc atcgcgatga cgcacggtac ctgcgcgcg                              39

<210> SEQ ID NO 189
<211> LENGTH: 39
<212> TYPE: DNA
<213> ORGANISM: Homo sapiens

<400> SEQUENCE: 189
cgcgcgcagg taccgtgcgt catcgcgatg gcccagctc                              39

<210> SEQ ID NO 190
<211> LENGTH: 45
<212> TYPE: DNA
<213> ORGANISM: Homo sapiens

<400> SEQUENCE: 190
cggaggccga tccaggtcat gataatgggc agcgcccgag tggcg                       45

<210> SEQ ID NO 191
<211> LENGTH: 45
<212> TYPE: DNA
<213> ORGANISM: Homo sapiens

<400> SEQUENCE: 191

```
cgccactcgg gcgctgccca ttatcatgac ctggatcggc ctccg            45
```

<210> SEQ ID NO 192
<211> LENGTH: 39
<212> TYPE: DNA
<213> ORGANISM: Homo sapiens

<400> SEQUENCE: 192

```
acggccgcgg cccggggtcc ggtagaggag gtgcgggcg                   39
```

<210> SEQ ID NO 193
<211> LENGTH: 39
<212> TYPE: DNA
<213> ORGANISM: Homo sapiens

<400> SEQUENCE: 193

```
cgcccgcacc tcctctaccg daccccgggc cgcggccgt                   39
```

<210> SEQ ID NO 194
<211> LENGTH: 39
<212> TYPE: DNA
<213> ORGANISM: Homo sapiens

<400> SEQUENCE: 194

```
gactggctgg ccacggcccc ggcccggggt cgggtagag                   39
```

<210> SEQ ID NO 195
<211> LENGTH: 39
<212> TYPE: DNA
<213> ORGANISM: Homo sapiens

<400> SEQUENCE: 195

```
ctctacccga ccccgggccg gggccgtggc cagccagtc                   39
```

<210> SEQ ID NO 196
<211> LENGTH: 39
<212> TYPE: DNA
<213> ORGANISM: Homo sapiens

<400> SEQUENCE: 196

```
catgcccgca tagatgccac ggaaggtccc tcagacatc                   39
```

<210> SEQ ID NO 197
<211> LENGTH: 39
<212> TYPE: DNA
<213> ORGANISM: Homo sapiens

<400> SEQUENCE: 197

```
gatgtctgag ggaccttccg tggcatctat gcgggcatg                   39
```

<210> SEQ ID NO 198
<211> LENGTH: 39
<212> TYPE: DNA
<213> ORGANISM: Homo sapiens

<400> SEQUENCE: 198

```
caggtcatga tgatgggcaa cgcccgagtg gcggagctg                   39
```

<210> SEQ ID NO 199
<211> LENGTH: 39
<212> TYPE: DNA
<213> ORGANISM: Homo sapiens -continued

<400> SEQUENCE: 199
cagctccgcc actcgggcgt tgcccatcat catgacctg                                  39

<210> SEQ ID NO 200
<211> LENGTH: 45
<212> TYPE: DNA
<213> ORGANISM: Homo sapiens

<400> SEQUENCE: 200
atccaggtca tgatgatggg catcgcccga gtggcggagc tgctg                           45

<210> SEQ ID NO 201
<211> LENGTH: 45
<212> TYPE: DNA
<213> ORGANISM: Homo sapiens

<400> SEQUENCE: 201
cagcagctcc gccactcggg cgatgccat catcatgacc tggat                            45

<210> SEQ ID NO 202
<211> LENGTH: 39
<212> TYPE: DNA
<213> ORGANISM: Homo sapiens

<400> SEQUENCE: 202
gtggtgctgc accgggcctg ggcgcggctg gacgtgcgc                                  39

<210> SEQ ID NO 203
<211> LENGTH: 39
<212> TYPE: DNA
<213> ORGANISM: Homo sapiens

<400> SEQUENCE: 203
gcgcacgtcc agccgcgccc aggcccggtg cagcaccac                                  39

<210> SEQ ID NO 204
<211> LENGTH: 39
<212> TYPE: DNA
<213> ORGANISM: Homo sapiens

<400> SEQUENCE: 204
agaggcagta accatgcctg catagatgcc gcggaaggt                                  39

<210> SEQ ID NO 205
<211> LENGTH: 39
<212> TYPE: DNA
<213> ORGANISM: Homo sapiens

<400> SEQUENCE: 205
accttccgcg gcatctatgc aggcatggtt actgcctct                                  39

<210> SEQ ID NO 206
<211> LENGTH: 39
<212> TYPE: DNA
<213> ORGANISM: Homo sapiens

<400> SEQUENCE: 206
agcatggagc cttcggctgg ctggctggcc acggccgcg                                  39

<210> SEQ ID NO 207
<211> LENGTH: 39
<212> TYPE: DNA
<213> ORGANISM: Homo sapiens

<400> SEQUENCE: 207
cgcggccgtg gccagccagc cagccgaagg ctccatgct         39

<210> SEQ ID NO 208
<211> LENGTH: 39
<212> TYPE: DNA
<213> ORGANISM: Homo sapiens

<400> SEQUENCE: 208
cgggcgctgc tggaggcgga ggcgctgccc aacgcaccg         39

<210> SEQ ID NO 209
<211> LENGTH: 39
<212> TYPE: DNA
<213> ORGANISM: Homo sapiens

<400> SEQUENCE: 209
cggtgcgttg ggcagcgcct ccgcctccag cagcgcccg         39

<210> SEQ ID NO 210
<211> LENGTH: 39
<212> TYPE: DNA
<213> ORGANISM: Homo sapiens

<400> SEQUENCE: 210
gcgcggctgg acgtgcgcaa tgcctggggc cgtctgccc         39

<210> SEQ ID NO 211
<211> LENGTH: 39
<212> TYPE: DNA
<213> ORGANISM: Homo sapiens

<400> SEQUENCE: 211
gggcagacgg ccccaggcat tgcgcacgtc cagccgcgc         39

<210> SEQ ID NO 212
<211> LENGTH: 6574
<212> TYPE: DNA
<213> ORGANISM: Homo sapiens

<400> SEQUENCE: 212
gacggatcgg gagatctccc gatcccctat ggtgcactct cagtacaatc tgctctgatg        60
ccgcatagtt aagccagtat ctgctccctg cttgtgtgtt ggaggtcgct gagtagtgcg       120
cgagcaaaat ttaagctaca acaaggcaag gcttgaccga caattgcatg aagaatctgc       180
ttagggttag gcgttttgcg ctgcttgcg atgtacgggc cagatatacg cgttgacatt        240
gattattgac tagttattaa tagtaatcaa ttacggggtc attagttcat agcccatata       300
tggagttccg cgttacataa cttacggtaa atggcccgcc tggctgaccg cccaacgacc       360
cccgcccatt gacgtcaata atgacgtatg ttcccatagt aacgccaata ggactttcc        420 attgacgtca atgggtggag tatttacggt aaactgccca cttggcagta catcaagtgt       480
atcatatgcc aagtacgccc cctattgacg tcaatgacgg taaatggccc gcctggcatt       540
atgcccagta catgacctta tgggactttc ctacttggca gtacatctac gtattagtca       600
tcgctattac catggtgatg cggttttggc agtacatcaa tgggcgtgga tagcggtttg       660
actcacgggg atttccaagt ctccacccca ttgacgtcaa tgggagtttg ttttggcacc       720
aaaatcaacg ggactttcca aaatgtcgta acaactccgc cccattgacg caaatgggcg       780

```
gtaggcgtgt acggtgggag gtctatataa gcagagctct ctggctaact agagaaccca    840
ctgcttactg gcttatcgaa attaatacga ctcactatag ggagacccaa gctggctagc    900
cgccaccatg ccggtctaat tgaagccaac ggagaactca aggtcttcat agaccagaac    960
cttagtcccg ggaaaggcgt ggtgtccctc gtggccgttc acccctccac cgtcaacccg   1020
ctcgggaagc agctcttgcc aaaaaccttt ggacagtcca atgtcaacat tgcccagcaa   1080
gtggtaattg gtacgcctca gagaccggca gcgtcaaaca ccctggtggt aggaagccca   1140
cacacccca gcactcactt tgcctctcag aaccagcctt ccgactcctc accttggtct   1200
gccgggaagc gcaacaggaa aggagagaag aatggcaagg gcctacggca tttctccatg   1260
aaggtctgcg agaaggtgca gaggaaaggg accacttcct acaacgaagt ggcagacgag   1320
ctggttgcgg agttcagtgc tgccgacaac acatcttac caaacgagtc agcttatgac   1380
cagaaaaaca taagacggcg cgtctacgat gccttaaacg tgctaatggc catgaacatc   1440
atctccaagg agaagaagga gatcaagtgg attggtctgc ccaccaactc ggctcaggaa   1500
tgtcagaact tagaggtgga aagacagagg agacttgaaa gaataaaaca gaaacagtct   1560
caacttcaag aacttattct acagcaaatt gccttcaaga acctggtgca gagaaaccgg   1620
catgcggagc agcaggccag ccggccaccg ccacccaact cagtcatcca cctgcccttc   1680
atcatcgtca acaccagcaa gaagacggtc atcgactgca gcatctccaa tgacaaattt   1740
gagtatctgt ttaattttga caacacattt gaaatccacg atgacataga agtgctgaag   1800
cggatgggca tggcttgcgg gctggagtcg gggagctgct ctgccgaaga ccttaaaatg   1860
gccagaagtc tggtccccaa ggctctggag ccatacgtga cagaaatggc tcagggaact   1920
gttggaggcg tgttcatcac gacggcaggt tccacgtcta acggcacaag gttctctgcc   1980
agtgacctga ccaacggtgc agatgggatg ctggccacaa gctccaatgg gtctcagtac   2040
agcggctcca gggtggagac tccggtgtcc tacgtcgggg aggacgacga ggaggacgat   2100
gacttcaacg agaatgacga ggacgactga ctcgagtcta gagggcccgt ttaaacccgc   2160
tgatcagcct cgactgtgcc ttctagttgc cagccatctg ttgtttgccc ctccccgtg   2220
ccttccttga ccctggaagg tgccactccc actgtccttt cctaataaaa tgaggaaatt   2280
gcatcgcatt gtctgagtag gtgtcattct attctggggg gtggggtggg gcaggacagc   2340
aagggggagg attgggaaga caatagcagg catgctgggg atgcggtggg ctctatggct   2400
tctgaggcgg aaagaaccag ctggggctct agggggtatc cccacgcgcc ctgtagcggc   2460
gcattaagcg cggcgggtgt ggtggttacg cgcagcgtga ccgctacact tgccagcgcc   2520
ctagcgcccg ctcctttcgc tttcttccct tcctttctcg ccacgttcgc cggctttccc   2580
cgtcaagctc taaatcgggg gctcccttta gggttccgat ttagtgcttt acggcacctc   2640
gaccccaaaa aacttgatta gggtgatggt tcacgtagtg gccatcgcc ctgatagacg   2700
gtttttcgcc ctttgacgtt ggagtccacg ttctttaata gtggactctt gttccaaact   2760
ggaacaacac tcaaccctat ctcggtctat tcttttgatt tataagggat tttgccgatt   2820
tcggcctatt ggttaaaaaa tgagctgatt taacaaaaat ttaacgcgaa ttaattctgt   2880
ggaatgtgtg tcagttaggg tgtggaaagt ccccaggctc cccagcaggc agaagtatgc   2940
aaagcatgca tctcaattag tcagcaacca ggtgtggaaa gtccccaggc tccccagcag   3000
gcagaagtat gcaaagcatg catctcaatt agtcagcaac catagtcccg cccctaactc   3060
cgcccatccc gcccctaact ccgcccagtt ccgcccattc tccgcccat ggctgactaa   3120
tttttttttat ttatgcagag gccgaggccg cctctgcctc tgagctattc cagaagtagt   3180
```

```
gaggaggctt ttttggaggc ctaggctttt gcaaaaagct cccgggagct tgtatatcca   3240
ttttcggatc tgatcaagag acaggatgag gatcgtttcg catgattgaa caagatggat   3300
tgcacgcagg ttctccggcc gcttgggtgg agaggctatt cggctatgac tgggcacaac   3360
agacaatcgg ctgctctgat gccgccgtgt tccggctgtc agcgcagggg cgcccggttc   3420
tttttgtcaa gaccgacctg tccggtgccc tgaatgaact gcaggacgag gcagcgcggc   3480
tatcgtggct ggccacgacg ggcgttcctt gcgcagctgt gctcgacgtt gtcactgaag   3540
cgggaaggga ctggctgcta ttgggcgaag tgccggggca ggatctcctg tcatctcacc   3600
ttgctcctgc cgagaaagta tccatcatgg ctgatgcaat gcggcggctg catacgcttg   3660
atccggctac ctgcccattc gaccaccaag cgaaacatcg catcgagcga gcacgtactc   3720
ggatggaagc cggtcttgtc gatcaggatg atctggacga agagcatcag gggctcgcgc   3780
cagccgaact gttcgccagg ctcaaggcgc gcatgcccga cggcgaggat ctcgtcgtga   3840
cccatggcga tgcctgcttg ccgaatatca tggtggaaaa tggccgcttt tctggattca   3900
tcgactgtgg ccggctgggt gtggcggacc gctatcagga catagcgttg gctacccgtg   3960
atattgctga gagcttggc ggcgaatggg ctgaccgctt cctcgtgctt tacggtatcg   4020
ccgctcccga ttcgcagcgc atcgccttct atcgccttct tgacgagttc ttctgagcgg   4080
gactctgggg ttcgaaatga ccgaccaagc gacgcccaac ctgccatcac gagatttcga   4140
ttccaccgcc gccttctatg aaaggttggg cttcggaatc gttttccggg acgccggctg   4200
gatgatcctc cagcgcgggg atctcatgct ggagttcttc gcccacccca acttgtttat   4260
tgcagcttat aatggttaca aataaagcaa tagcatcaca aatttcacaa ataaagcatt   4320
tttttcactg cattctagtt gtggtttgtc caaactcatc aatgtatctt atcatgtctg   4380
tataccgtcg acctctagct agagcttggc gtaatcatgg tcatagctgt ttcctgtgtg   4440
aaattgttat ccgctcacaa ttccacacaa catacgagcc ggaagcataa agtgtaaagc   4500
ctggggtgcc taatgagtga gctaactcac attaattgcg ttgcgctcac tgcccgcttt   4560
ccagtcggga aacctgtcgt gccagctgca ttaatgaatc ggccaacgcg cggggagagg   4620
cggtttgcgt attgggcgct cttccgcttc ctcgctcact gactcgctgc gctcggtcgt   4680
tcggctgcgg cgagcggtat cagctcactc aaaggcggta atacggttat ccacagaatc   4740
aggggataac gcaggaaaga acatgtgagc aaaaggccag caaaaggcca ggaaccgtaa   4800
aaaggccgcg ttgctggcgt ttttccatag gctccgcccc cctgacgagc atcacaaaaa   4860
tcgacgctca agtcagaggt ggcgaaaccc gacaggacta taaagatacc aggcgtttcc   4920
ccctggaagc tccctcgtgc gctctcctgt tccgaccctg ccgcttaccg gatacctgtc   4980
cgcctttctc ccttcgggaa gcgtggcgct ttctcatagc tcacgctgta ggtatctcag   5040
ttcggtgtag gtcgttcgct ccaagctggg ctgtgtgcac gaaccccccg ttcagcccga   5100
ccgctgcgcc ttatccggta actatcgtct tgagtccaac ccggtaagac acgacttatc   5160
gccactggca gcagccactg gtaacaggat tagcagagcg aggtatgtag gcggtgctac   5220
agagttcttg aagtggtggc ctaactacgg ctacactaga agaacagtat ttggtatctg   5280
cgctctgctg aagccagtta ccttcggaaa aagagttggt agctcttgat ccggcaaaca   5340
aaccaccgct ggtagcggtt ttttttgtttg caagcagcag attacgcgca gaaaaaaagg   5400
atctcaagaa gatcctttga tcttttctac ggggtctgac gctcagtgga acgaaaactc   5460
acgttaaggg attttggtca tgagattatc aaaaaggatc ttcacctaga tccttttaaa   5520
```

```
ttaaaaatga agttttaaat caatctaaag tatatatgag taaacttggt ctgacagtta      5580
ccaatgctta atcagtgagg cacctatctc agcgatctgt ctatttcgtt catccatagt      5640
tgcctgactc cccgtcgtgt agataactac gatacgggag ggcttaccat ctggccccag      5700
tgctgcaatg ataccgcgag acccacgctc accggctcca gatttatcag caataaacca      5760
gccagccgga agggccgagc gcagaagtgg tcctgcaact ttatccgcct ccatccagtc      5820
tattaattgt tgccgggaag ctagagtaag tagttcgcca gttaatagtt tgcgcaacgt      5880
tgttgccatt gctacaggca tcgtggtgtc acgctcgtcg tttggtatgg cttcattcag      5940
ctccggttcc caacgatcaa ggcgagttac atgatccccc atgttgtgca aaaaagcggt      6000
tagctccttc ggtcctccga tcgttgtcag aagtaagttg gccgcagtgt tatcactcat      6060
ggttatggca gcactgcata attctcttac tgtcatgcca tccgtaagat gcttttctgt      6120
gactggtgag tactcaacca agtcattctg agaatagtgt atgcggcgac cgagttgctc      6180
ttgcccggcg tcaatacggg ataataccgc gccacatagc agaactttaa aagtgctcat      6240
cattggaaaa cgttcttcgg ggcgaaaact ctcaaggatc ttaccgctgt tgagatccag      6300
ttcgatgtaa cccactcgtg cacccaactg atcttcagca tcttttactt tcaccagcgt      6360
ttctgggtga gcaaaaacag gaaggcaaaa tgccgcaaaa aagggaataa gggcgacacg      6420
gaaatgttga atactcatac tcttcctttt tcaatattat tgaagcattt atcagggtta      6480
ttgtctcatg agcggataca tatttgaatg tatttagaaa aataaacaaa taggggttcc      6540
gcgcacattt ccccgaaaag tgccacctga cgtc                                  6574

<210> SEQ ID NO 213
<211> LENGTH: 6605
<212> TYPE: DNA
<213> ORGANISM: Homo sapiens

<400> SEQUENCE: 213
gacggatcgg gagatctccc gatccctat ggtgcactct cagtacaatc tgctctgatg        60
ccgcatagtt aagccagtat ctgctccctg cttgtgtgtt ggaggtcgct gagtagtgcg      120
cgagcaaaat ttaagctaca acaaggcaag gcttgaccga caattgcatg aagaatctgc      180
ttagggttag gcgttttgcg ctgcttcgcg atgtacgggc cagatatacg cgttgacatt      240
gattattgac tagttattaa tagtaatcaa ttacggggtc attagttcat agcccatata      300
tggagttccg cgttacataa cttacggtaa atggcccgcc tggctgaccg cccaacgacc      360
cccgcccatt gacgtcaata atgacgtatg ttcccatagt aacgccaata gggactttcc      420
attgacgtca atgggtggag tatttacggt aaactgccca cttggcagta catcaagtgt      480
atcatatgcc aagtacgccc cctattgacg tcaatgacgg taaatggccc gcctggcatt      540
atgcccagta catgacctta tgggactttc ctacttggca gtacatctac gtattagtca      600
tcgctattac catggtgatg cggttttggc agtacatcaa tgggcgtgga tagcggtttg      660
actcacgggg atttccaagt ctccacccca ttgacgtcaa tgggagtttg ttttggcacc      720
aaaatcaacg ggactttcca aaatgtcgta acaactccgc cccattgacg caaatgggcg      780
gtaggcgtgt acggtgggag gtctatataa gcagagctct ctggctaact agagaaccca      840
ctgcttactg gcttatcgaa attaatacga ctcactatag ggagacccaa gctggctagc      900
gtttaaactt aagcttgcca ccatggcctt ggccggcccc tgcgaccctg acctgctgct      960
cttcgccaca ccgcaggcgc cccggcccac acccagtgcg ccgcggcccg cgctcggccg     1020
cccgccggtg aagcggaggc tggacctgga aactgaccat cagtacctgg ccgagagcag     1080
```

```
tgggccagct cggggcagag gccgccatcc aggaaaaggt gtgaaatccc cgggggagaa    1140
gtcacgctat gagacctcac tgaatctgac caccaagcgc ttcctggagc tgctgagcca    1200
ctcggctgac ggtgtcgtcg acctgaactg ggctgccgag gtgctgaagg tgcagaagcg    1260
gcgcatctat gacatcacca acgtccttga gggcatccag ctcattgcca agaagtccaa    1320
gaaccacatc cagtggctgg gcagccacac cacagtgggc gtcggcggac ggcttgaggg    1380
gttgacccag gacctccgac agctgcagga gagcgagcag cagctggacc acctgatgaa    1440
tatctgtact acgcagctgc gcctgctctc cgaggacact gacagccagc gcctggccta    1500
cgtgacgtgt caggaccttc gtagcattgc agacctgca gagcagatgg ttatggtgat     1560
caaagcccct cctgagaccc agctccaagc cgtggactct tcggagaact ttcagatctc    1620
ccttaagagc aaacaaggcc cgatcgatgt tttcctgtgc cctgaggaga ccgtaggtgg    1680
gatcagccct gggaagaccc catcccagga ggtcacttct gaggaggaga cagggccac    1740 tgactctgcc accatagtgt caccaccacc atcatctccc ccctcatccc tcaccacaga   1800
tcccagccag tctctactca gcctggagca agaaccgctg ttgtcccgga tgggcagcct   1860
gcgggctccc gtggacgagg accgcctgtc ccgctggtg gcggccgact cgctcctgga    1920
gcatgtgcgg gaggacttct ccggcctcct ccctgaggag ttcatcagcc tttccccacc    1980
ccacgaggcc ctcgactacc acttcggcct cgaggagggc gagggcatca gagacctctt    2040
cgactgtgac tttggggacc tcaccccct ggatttcggg aattctggct cgagcggtgg     2100
tggcgggagc ggaggtggag ggtcgtcagg tgtgaccggc taccggctgt tcgaggagat    2160
tctgtaatct agagggcccg tttaaacccg ctgatcagcc tcgactgtgc cttctagttg    2220
ccagccatct gttgtttgcc cctccccgt gccttcctg accctggaag gtgccactcc      2280
cactgtcctt tcctaataaa atgaggaaat tgcatcgcat tgtctgagta ggtgtcattc    2340
tattctgggg ggtggggtgg ggcaggacag caaggggag gattgggaag acaatagcag    2400
gcatgctggg gatgcggtgg gctctatggc ttctgaggcg gaaagaacca gctggggctc    2460
tagggggtat ccccacgcgc cctgtagcgg cgcattaagc gcggcgggtg tggtggttac    2520
gcgcagcgtg accgctacac ttgccagcgc cctagcgccc gctcctttcg ctttcttccc    2580
ttcctttctc gccacgttcg ccggctttcc ccgtcaagct ctaaatcggg gctccctt     2640 agggttccga tttagtgctt tacggcacct cgaccccaaa aaacttgatt agggtgatgg    2700
ttcacgtagt gggccatcgc cctgatagac ggttttcgc cctttgacgt tggagtccac     2760
gttctttaat agtggactct tgttccaaac tggaacaaca ctcaacccta tctcggtcta    2820 ttctttgat ttataaggga ttttgccgat ttcggcctat tggttaaaaa atgagctgat     2880
ttaacaaaaa tttaacgcga attaattctg tggaatgtgt gtcagttagg gtgtggaaag    2940
tccccaggct ccccagcagg cagaagtatg caaagcatgc atctcaatta gtcagcaacc    3000
aggtgtggaa agtccccagg ctccccagca ggcagaagta tgcaaagcat gcatctcaat    3060
tagtcagcaa ccatagtccc gcccctaact ccgcccatcc cgcccctaac tccgcccagt    3120
tccgcccatt ctccgcccca tggctgacta atttttttta tttatgcaga ggccgaggcc    3180
gcctctgcct ctgagctatt ccagaagtag tgaggaggct tttttggagg cctaggcttt    3240
tgcaaaaagc tcccgggagc ttgtatatcc attttcggat ctgatcaaga gacaggatga    3300
ggatcgtttc gcatgattga acaagatgga ttgcacgcag ttctccggc cgcttgggtg    3360 gagaggctat tcggctatga ctgggcacaa cagacaatcg gctgctctga tgccgccgtg    3420
```

-continued

```
ttccggctgt cagcgcaggg gcgcccggtt ctttttgtca agaccgacct gtccggtgcc    3480
ctgaatgaac tgcaggacga ggcagcgcgg ctatcgtggc tggccacgac gggcgttcct    3540
tgcgcagctg tgctcgacgt tgtcactgaa gcgggaaggg actggctgct attgggcgaa    3600
gtgccgggga aggatctcct gtcatctcac cttgctcctg ccgagaaagt atccatcatg    3660
gctgatgcaa tgcggcggct gcatacgctt gatccggcta cctgcccatt cgaccaccaa    3720
gcgaaacatc gcatcgagcg agcacgtact cggatggaag ccggtcttgt cgatcaggat    3780
gatctggacg aagagcatca ggggctcgcg ccagccgaac tgttcgccag gctcaaggcg    3840
cgcatgcccg acggcgagga tctcgtcgtg acccatggcg atgcctgctt gccgaatatc    3900
atggtggaaa atggccgctt ttctggattc atcgactgtg gccggctggg tgtggcggac    3960
cgctatcagg acatagcgtt ggctacccgt gatattgctg aagagcttgg cggcgaatgg    4020
gctgaccgct tcctcgtgct ttacggtatc gccgctcccg attcgcagcg catcgccttc    4080
tatcgccttc ttgacgagtt cttctgagcg ggactctggg gttcgaaatg accgaccaag    4140
cgacgcccaa cctgccatca cgagatttcg attccaccgc cgccttctat gaaaggttgg    4200
gcttcggaat cgttttccgg gacgccggct ggatgatcct ccagcgcggg gatctcatgc    4260
tggagttctt cgcccacccc aacttgttta ttgcagctta taatggttac aaataaagca    4320
atagcatcac aaatttcaca aataaagcat ttttttcact gcattctagt tgtggttgt    4380 ccaaactcat caatgtatct tatcatgtct gtataccgtc gacctctagc tagagcttgg    4440
cgtaatcatg gtcatagctg tttcctgtgt gaaattgtta tccgctcaca attccacaca    4500
acatacgagc cggaagcata aagtgtaaag cctggggtgc ctaatgagtg agctaactca    4560
cattaattgc gttgcgctca ctgcccgctt tccagtcggg aaacctgtcg tgccagctgc    4620
attaatgaat cggccaacgc gcggggagag gcggtttgcg tattgggcgc tcttccgctt    4680
cctcgctcac tgactcgctg cgctcggtcg ttcggctgcg gcgagcggta tcagctcact    4740
caaaggcggt aatacggtta tccacagaat caggggataa cgcaggaaag aacatgtgag    4800
caaaaggcca gcaaaaggcc aggaaccgta aaaaggccgc gttgctggcg ttttttccata    4860 ggctccgccc ccctgacgag catcacaaaa atcgacgctc aagtcagagg tggcgaaacc    4920
cgacaggact ataaagatac caggcgtttc cccctggaag ctccctcgtg cgctctcctg    4980
ttccgaccct gccgcttacc ggatacctgt ccgcctttct cccttcggga agcgtggcgc    5040
tttctcatag ctcacgctgt aggtatctca gttcggtgta ggtcgttcgc tccaagctgg    5100
gctgtgtgca cgaacccccc gttcagcccg accgctgcgc cttatccggt aactatcgtc    5160
ttgagtccaa cccggtaaga cacgacttat cgccactggc agcagccact ggtaacagga    5220
ttagcagagc gaggtatgta ggcggtgcta cagagttctt gaagtggtgg cctaactacg    5280
gctacactag aagaacagta tttggtatct gcgctctgct gaagccagtt accttcggaa    5340
aaagagttgg tagctcttga tccggcaaac aaaccaccgc tggtagcggt ttttttgttt    5400
gcaagcagca gattacgcgc agaaaaaaag gatctcaaga agatcctttg atcttttcta    5460
cggggtctga cgctcagtgg aacgaaaact cacgttaagg attttggtc atgagattat    5520 caaaaaggat cttcacctag atcctttta attaaaaatg aagttttaaa tcaatctaaa    5580
gtatatatga gtaaacttgg tctgacagtt accaatgctt aatcagtgag gcacctatct    5640
cagcgatctg tctatttcgt tcatccatag ttgcctgact ccccgtcgtg tagataacta    5700
cgatacggga gggcttacca tctggcccca gtgctgcaat gataccgcga cccacgctc    5760 caccggctcc agatttatca gcaataaacc agccagccgg aagggccgag cgcagaagtg    5820
```

| | |
|---|---|
| gtcctgcaac tttatccgcc tccatccagt ctattaattg ttgccgggaa gctagagtaa | 5880 |
| gtagttcgcc agttaatagt ttgcgcaacg ttgttgccat tgctacaggc atcgtggtgt | 5940 |
| cacgctcgtc gtttggtatg gcttcattca gctccggttc ccaacgatca aggcgagtta | 6000 |
| catgatcccc catgttgtgc aaaaaagcgg ttagctcctt cggtcctccg atcgttgtca | 6060 |
| gaagtaagtt ggccgcagtg ttatcactca tggttatggc agcactgcat aattctctta | 6120 |
| ctgtcatgcc atccgtaaga tgcttttctg tgactggtga gtactcaacc aagtcattct | 6180 |
| gagaatagtg tatgcggcga ccgagttgct cttgcccggc gtcaatacgg gataataccg | 6240 |
| cgccacatag cagaacttta aaagtgctca tcattggaaa acgttcttcg ggcgaaaac | 6300 |
| tctcaaggat cttaccgctg ttgagatcca gttcgatgta acccactcgt gcacccaact | 6360 |
| gatcttcagc atcttttact ttcaccagcg tttctgggtg agcaaaaaca ggaaggcaaa | 6420 |
| atgccgcaaa aaagggaata agggcgacac ggaaatgttg aatactcata ctcttccttt | 6480 |
| ttcaatatta ttgaagcatt tatcagggtt attgtctcat gagcggatac atatttgaat | 6540 |
| gtatttagaa aaataaacaa ataggggttc cgcgcacatt tccccgaaaa gtgccacctg | 6600 |
| acgtc | 6605 |

<210> SEQ ID NO 214
<211> LENGTH: 7573
<212> TYPE: DNA
<213> ORGANISM: Homo sapiens

<400> SEQUENCE: 214

| | |
|---|---|
| gacggatcgg gagatctccc gatcccctat ggtgcactct cagtacaatc tgctctgatg | 60 |
| ccgcatagtt aagccagtat ctgctccctg cttgtgtgtt ggaggtcgct gagtagtgcg | 120 |
| cgagcaaaat ttaagctaca acaaggcaag gcttgaccga caattgcatg aagaatctgc | 180 |
| ttagggttag gcgttttgcg ctgcttcgcg atgtacgggc cagatatacg cgttgacatt | 240 |
| gattattgac tagttattaa tagtaatcaa ttacggggtc attagttcat agcccatata | 300 |
| tggagttccg cgttacataa cttacggtaa atggcccgcc tggctgaccg cccaacgacc | 360 |
| cccgcccatt gacgtcaata atgacgtatg ttcccatagt aacgccaata gggactttcc | 420 |
| attgacgtca atgggtggag tatttacggt aaactgccca cttggcagta catcaagtgt | 480 |
| atcatatgcc aagtacgccc cctattgacg tcaatgacgg taaatggccc gcctggcatt | 540 |
| atgcccagta catgacctta tgggactttc ctacttggca gtacatctac gtattagtca | 600 |
| tcgctattac catggtgatg cggttttggc agtacatcaa tgggcgtgga tagcggtttg | 660 |
| actcacgggg atttccaagt ctccacccca ttgacgtcaa tgggagtttg ttttggcacc | 720 |
| aaaatcaacg ggactttcca aaatgtcgta acaactccgc cccattgacg caaatgggcg | 780 |
| gtaggcgtgt acggtgggag gtctatataa gcagagctct ctggctaact agagaaccca | 840 |
| ctgcttactg gcttatcgaa attaatacga ctcactatag ggagacccaa gctggctagc | 900 |
| gtttaaactt aagcttggca atccggtact gttggtaaag ccaccatggt cttcacactc | 960 |
| gaagatttcg ttggggactg gaacagaca gccgcctaca acctggacca agtccttgaa | 1020 |
| cagggaggtg tgtccagttt gctgcagaat ctcgccgtgt ccgtaactcc gatccaaagg | 1080 |
| attgtccgga gcggtgaaaa tgccctgaag atcgacatcc atgtcatcat cccgtatgaa | 1140 |
| ggtctgagcg ccgaccaaat ggcccagatc gaagaggtgt taaggtggt gtaccctgtg | 1200 |
| gatgatcatc actttaaggt gatcctgccc tatggcacac tggtaatcga cggggttacg | 1260 |

```
ccgaacatgc tgaactattt cggacggccg tatgaaggca tcgccgtgtt cgacggcaaa      1320
aagatcactg taacagggac cctgtggaac ggcaacaaaa ttatcgacga gcgcctgatc      1380 accccccgacg gctccatgct gttccgagta accatcaaca gtgggagttc cggtggtggc      1440
gggagcggag gtggaggctc gagcggtgga gctcagggga attcaaacac tatccaacaa      1500
ttaatgatga ttttaaattc agcaagtgat caaccttcag aaaatctgat ttcctatttt      1560
aacaactgca cagtgaatcc aaaagaaagt atactgaaaa gagtgaagga taggatac        1620 atctttaaag agaaatttgc taaagctgtg gacagggtt gtgtcgaaat tggatcacag       1680
cgatacaaac ttggagttcg cttgtattac cgagtaatgg aatccatgct aaatcagaa       1740 gaagaacgat tatccattca aaattttagc aaacttctga tgacaacat ttttcatatg       1800 tctttattgg cgtgcgctct tgaggttgta atggccacat atagcagaag tacatctcag      1860
aatcttgatt ctggaacaga tttgtctttc ccatggattc tgaatgtgct taatttaaaa      1920
gcctttgatt tttacaaagt gatcgaaagt tttatcaaag cagaaggcaa cttgacaaga      1980
gaaatgataa acatttaga acgatgtgaa catcgaatca tggaatccct tgcatggctc       2040
tcagattcac cttatttga tcttattaaa caatcaaagg accgagaagg accaactgat       2100
caccttgaat ctgcttgtcc tcttaatctt cctctccaga taatcacac tgcagcagat       2160 atgtatcttt ctcctgtaag atctccaaag aaaaaaggtt caactacgcg tgtaaattct      2220
actgcaaatg cagagacaca agcaacctca gccttccaga cccagaagcc attgaaatct      2280
acctctcttt cactgtttta taaaaaagtg tatcggctag cctatctccg gctaaataca      2340
ctttgtgaac gccttctgtc tgagcaccca gaattagaac atatcatctg daccccttttc     2400 cagcacaccc tgcagaatga gtatgaactc atgagagaca ggcatttgga ccaaattatg      2460
atgtgttcca tgtatggcat atgcaaagtg aagaatatag accttaaatt caaaatcatt      2520
gtaacagcat acaaggatct tcctcatgct gttcaggaga cattcaaacg tgttttgatc      2580
aaagaagagg agtatgattc tattatagta ttctataact cggtcttcat gcagagactg      2640
aaaacaaata ttttgcagta tgcttccacc aggcccccta ccttgtcacc aatacctcac      2700
attcctcgaa gcccttacaa gtttcctagt tcacccttac ggattcctgg agggaacatc      2760
tatatttcac ccctgaagag tccatataaa atttcagaag gtctgccaac accaacaaaa      2820
atgactccaa gatcaagaat cttagtatca attggtgaat cattcgggac ttctgagaag      2880
ttccagaaaa taaatcagat ggtatgtaac agcgaccgtg tgctcaaaag aagtgctgaa      2940
ggaagcaacc ctcctaaacc actgaaaaaa ctacgctttg atattgaagg atcagatgaa      3000
gcagatggaa gtaaacatct cccaggagag tccaaatttc agcagaaact ggcagaaatg      3060
acttctactc gaacacgaat gcaaaagcag aaaatgaatg atagcatgga tacctcaaac      3120
aaggaagaga aatgatctag agggcccgtt taaacccgct gatcagcctc gactgtgcct      3180
tctagttgcc agccatctgt tgtttgcccc tcccccgtgc cttccttgac cctggaaggt      3240
gccactccca ctgtcctttc ctaataaaat gaggaaattg catcgcattg tctgagtagg      3300
tgtcattcta ttctgggggg tggggtgggg caggacagca agggggagga ttggaagac      3360 aatagcaggc atgctgggga tgcggtggc tctatggctt ctgaggcgga aagaaccagc       3420
tggggctcta gggggtatcc ccacgcgccc tgtagcggcg cattaagcgc ggcgggtgtg      3480
gtggttacgc gcagcgtgac cgctacactt gccagcgccc tagcgcccgc tcctttcgct      3540
ttcttccctt cctttctcgc cacgttcgcc ggctttcccc gtcaagctct aaatcggggg      3600
ctccctttag ggttccgatt tagtgcttta cggcacctcg accccaaaaa acttgattag      3660
```

```
ggtgatggtt cacgtagtgg gccatcgccc tgatagacgg ttttcgccc tttgacgttg    3720 gagtccacgt tctttaatag tggactcttg ttccaaactg aacaacact caaccctatc    3780 tcggtctatt cttttgattt ataagggatt ttgccgattt cggcctattg gttaaaaaat   3840
gagctgattt aacaaaaatt taacgcgaat taattctgtg aatgtgtgt cagttaggggt   3900 gtggaaagtc cccaggctcc ccagcaggca gaagtatgca aagcatgcat ctcaattagt   3960
cagcaaccag gtgtggaaag tccccaggct ccccagcagg cagaagtatg caaagcatgc   4020
atctcaatta gtcagcaacc atagtcccgc ccctaactcc gcccatcccg ccctaactc    4080 cgcccagttc cgcccattct ccgccccatg gctgactaat ttttttatt tatgcagagg    4140 ccgaggccgc ctctgcctct gagctattcc agaagtagtg aggaggcttt tttggaggcc   4200
taggcttttg caaaaagctc cgggagctt gtatatccat tttcggatct gatcaagaga    4260
caggatgagg atcgtttcgc atgattgaac aagatggatt gcacgcaggt tctccggccg   4320
cttgggtgga gaggctattc ggctatgact gggcacaaca gacaatcggc tgctctgatg   4380
ccgccgtgtt ccggctgtca gcgcaggggc gcccggttct ttttgtcaag accgacctgt   4440
ccggtgccct gaatgaactg caggacgagg cagcgcggct atcgtggctg gccacgacgg   4500
gcgttccttg cgcagctgtg ctcgacgttg tcactgaagc gggaagggac tggctgctat   4560
tgggcgaagt gccggggcag gatcctcctgt catctcacct tgctcctgcc gagaaagtat   4620
ccatcatggc tgatgcaatg cggcggctgc atacgcttga tccggctacc tgcccattcg   4680
accaccaagc gaaacatcgc atcgagcgag cacgtactcg gatggaagcc ggtcttgtcg   4740
atcaggatga tctggacgaa gagcatcagg ggctcgcgcc agccgaactg ttcgccaggc   4800
tcaaggcgcg catgcccgac ggcgaggatc tcgtcgtgac ccatggcgat gcctgcttgc   4860
cgaatatcat ggtggaaaat ggccgctttt ctggattcat cgactgtggc cggctgggtg   4920
tggcggaccg ctatcaggac atagcgttgg ctacccgtga tattgctgaa gagcttggcg   4980
gcgaatgggc tgaccgcttc ctcgtgcttt acggtatcgc cgctcccgat tcgcagcgca   5040
tcgccttcta tcgccttctt gacgagttct tctgagcggg actctggggt tcgaaatgac   5100
cgaccaagcg acgcccaacc tgccatcacg agatttcgat tccaccgccg ccttctatga   5160
aaggttgggc ttcggaatcg ttttccggga cgccggctgg atgatcctcc agcgcgggga   5220
tctcatgctg gagttcttcg cccacccca cttgtttatt gcagcttata atggttacaa   5280
ataaagcaat agcatcacaa atttcacaaa taaagcattt ttttcactgc attctagttg   5340
tggtttgtcc aaactcatca atgtatctta tcatgtctgt ataccgtcga cctctagcta   5400
gagcttggcg taatcatggt catagctgtt tcctgtgtga aattgttatc cgctcacaat   5460
tccacacaac atacgagccg gaagcataaa gtgtaaagcc tggggtgcct aatgagtgag   5520
ctaactcaca ttaattgcgt tgcgctcact gcccgctttc cagtcgggaa acctgtcgtg   5580
ccagctgcat taatgaatcg gccaacgcgc ggggagaggc ggtttgcgta ttgggcgctc   5640
ttccgcttcc tcgctcactg actcgctgcg ctcggtcgtt cggctgcggc gagcggtatc   5700
agctcactca aaggcggtaa tacggttatc cacagaatca ggggataacg caggaaagaa   5760
catgtgagca aaaggccagc aaaaggccag gaaccgtaaa aaggccgcgt tgctggcgtt   5820
tttccatagg ctccgccccc ctgacgagca tcacaaaaat cgacgctcaa gtcagaggtg   5880
gcgaaacccg acaggactat aaagatacca ggcgtttccc cctggaagct ccctcgtgcg   5940
ctctcctgtt ccgaccctgc cgcttaccgg atacctgtcc gcctttctcc cttcgggaag   6000
```

| | | | |
|---|---|---|---|
| cgtggcgctt | tctcatagct cacgctgtag gtatctcagt tcggtgtagg tcgttcgctc | 6060 |
| caagctgggc | tgtgtgcacg aaccccccgt tcagcccgac cgctgcgcct tatccggtaa | 6120 |
| ctatcgtctt | gagtccaacc cggtaagaca cgacttatcg ccactggcag cagccactgg | 6180 |
| taacaggatt | agcagagcga ggtatgtagg cggtgctaca gagttcttga agtggtggcc | 6240 |
| taactacggc | tacactagaa gaacagtatt tggtatctgc gctctgctga agccagttac | 6300 |
| cttcggaaaa | agagttggta gctcttgatc cggcaaacaa accaccgctg gtagcggttt | 6360 |
| ttttgtttgc | aagcagcaga ttacgcgcag aaaaaaagga tctcaagaag atcctttgat | 6420 |
| cttttctacg | gggtctgacg ctcagtggaa cgaaaactca cgttaaggga ttttggtcat | 6480 |
| gagattatca | aaaaggatct tcacctagat ccttttaaat taaaaatgaa gttttaaatc | 6540 |
| aatctaaagt | atatatgagt aaacttggtc tgacagttac caatgcttaa tcagtgaggc | 6600 |
| acctatctca | gcgatctgtc tatttcgttc atccatagtt gcctgactcc ccgtcgtgta | 6660 |
| gataactacg | atacgggagg gcttaccatc tggccccagt gctgcaatga taccgcgaga | 6720 |
| cccacgctca | ccggctccag atttatcagc aataaaccag ccagccggaa gggccgagcg | 6780 |
| cagaagtggt | cctgcaactt tatccgcctc catccagtct attaattgtt gccgggaagc | 6840 |
| tagagtaagt | agttcgccag ttaatagttt gcgcaacgtt gttgccattg ctacaggcat | 6900 |
| cgtggtgtca | cgctcgtcgt ttggtatggc ttcattcagc tccggttccc aacgatcaag | 6960 |
| gcgagttaca | tgatccccca tgttgtgcaa aaaagcggtt agctccttcg gtcctccgat | 7020 |
| cgttgtcaga | agtaagttgg ccgcagtgtt atcactcatg gttatggcag cactgcataa | 7080 |
| ttctcttact | gtcatgccat ccgtaagatg cttttctgtg actggtgagt actcaaccaa | 7140 |
| gtcattctga | gaatagtgta tgcggcgacc gagttgctct tgcccggcgt caatacggga | 7200 |
| taataccgcg | ccacatagca gaactttaaa agtgctcatc attggaaaac gttcttcggg | 7260 |
| gcgaaaactc | tcaaggatct taccgctgtt gagatccagt tcgatgtaac ccactcgtgc | 7320 |
| acccaactga | tcttcagcat cttttacttt caccagcgtt tctgggtgag caaaaacagg | 7380 |
| aaggcaaaat | gccgcaaaaa agggaataag ggcgacacgg aaatgttgaa tactcatact | 7440 |
| cttcctttt | caatattatt gaagcattta tcagggttat tgtctcatga gcggatacat | 7500 |
| atttgaatgt | atttagaaaa ataaacaaat aggggttccg cgcacatttc cccgaaaagt | 7560 |
| gccacctgac | gtc | 7573 |

<210> SEQ ID NO 215
<211> LENGTH: 6668
<212> TYPE: DNA
<213> ORGANISM: Homo sapiens

<400> SEQUENCE: 215

| | | | |
|---|---|---|---|
| gacggatcgg | gagatctccc gatcccctat ggtgcactct cagtacaatc tgctctgatg | 60 |
| ccgcatagtt | aagccagtat ctgctccctg cttgtgtgtt ggaggtcgct gagtagtgcg | 120 |
| cgagcaaaat | ttaagctaca acaaggcaag gcttgaccga caattgcatg aagaatctgc | 180 |
| ttagggttag | gcgttttgcg ctgcttcgcg atgtacgggc cagatatacg cgttgacatt | 240 |
| gattattgac | tagttattaa tagtaatcaa ttacggggtc attagttcat agcccatata | 300 |
| tggagttccg | cgttacataa cttacggtaa atggcccgcc tggctgaccg cccaacgacc | 360 |
| cccgcccatt | gacgtcaata atgacgtatg ttcccatagt aacgccaata gggactttcc | 420 |
| attgacgtca | atgggtggag tatttacggt aaactgccca cttggcagta catcaagtgt | 480 |
| atcatatgcc | aagtacgccc cctattgacg tcaatgacgg taaatggccc gcctggcatt | 540 |

```
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaactt aagcttgcca ccatggctca ggaatgtcag aacttagagg tggaaagaca    960
gaggagactt gaaagaataa aacagaaaca gtctcaactt caagaactta ttctacagca   1020
aattgccttc aagaacctgg tgcagagaaa ccggcatgcg gagcagcagg ccagccggcc   1080
accgccaccc aactcagtca tccacctgcc cttcatcatc gtcaacacca gcaagaagac   1140
ggtcatcgac tgcagcatct ccaatgacaa atttgagtat ctgtttaatt ttgacaacac   1200
atttgaaatc cacgatgaca tagaagtgct gaagcggatg gcatggctt gcgggctgga   1260
gtcggggagc tgctctgccg aagaccttaa aatggccaga agtctggtcc ccaaggctct   1320
ggagccatac gtgacagaaa tggctcaggg aactgttgga ggcgtgttca tcacgacggc   1380
aggtggctct ggaggcggac ggcttgacgg gttgacccag gacctccgac agctgcagga   1440
gagcgagcag cagctggacc acctgatgaa tatctgtact acgcagctgc gcctgctctc   1500
cgaggacact gacagccagc gcctggccta cgtgacgtgt caggaccttc gtagcattgc   1560
agaccctgca gagcagatgg ttatggtgat caaagcccct cctgagaccc agctccaagc   1620
cgtggactct tcggagaact ttcagatctc ccttaagagc aaacaaggcc cgatcgatgt   1680
tttcctgtgc cctgaggagg ggaattctgg ctcgagcgt ggtggcggga gcggaggtgg   1740
agggtcgtca ggtgtcttca cactcgaaga tttcgttggg gactgggaac agacagccgc   1800
ctacaacctg gaccaagtcc ttgaacaggg aggtgtgtcc agtttgctgc agaatctcgc   1860
cgtgtccgta actccgatcc aaaggattgt ccggagcggt gaaaatgccc tgaagatcga   1920
catccatgtc atcatcccgt atgaaggtct gagcgccgac caaatggccc agatcgaaga   1980
ggtgtttaag gtggtgtacc ctgtggatga tcatcacttt aaggtgatcc tgcccatgg   2040
cacactggta atcgacgggg ttacgccgaa catgctgaac tatttcggac ggccgtatga   2100
aggcatcgcc gtgttcgacg gcaaaaagat cactgtaaca gggaccctgt ggaacggcaa   2160
caaaattatc gacgagcgcc tgatcacccc cgacggctcc atgctgttcc gagtaaccat   2220
caacagctaa tctagagggc ccgtttaaac ccgctgatca gcctcgactg tgccttctag   2280
ttgccagcca tctgttgttt gcccctcccc cgtgccttcc ttgaccctgg aaggtgccac   2340
tcccactgtc ctttcctaat aaaatgagga aattgcatcg cattgtctga gtaggtgtca   2400
ttctattctg gggggtgggg tggggcagga cagcaagggg gaggattggg aagacaatag   2460
caggcatgct ggggatgcgg tgggctctat ggcttctgag gcggaaagaa ccagctgggg   2520
ctctaggggg tatccccacg cgccctgtag cggcgcatta agcgcggcgg gtgtggtggt   2580
tacgcgcagc gtgaccgcta cacttgccag cgccctagcg cccgctcctt tcgctttctt   2640
cccttccttt ctcgccacgt tcgccggctt tccccgtcaa gctctaaatc ggggctccc   2700
tttagggttc cgatttagtg ctttacggca cctcgacccc aaaaaacttg attagggtga   2760
tggttcacgt agtgggccat cgccctgata gacggttttt cgccctttga cgttggagtc   2820
cacgttcttt aatagtggac tcttgttcca aactggaaca acactcaacc ctatctcggt   2880
```

```
ctattcttttt gatttataag ggattttgcc gatttcggcc tattggttaa aaaatgagct    2940
gatttaacaa aaatttaacg cgaattaatt ctgtggaatg tgtgtcagtt agggtgtgga    3000
aagtccccag gctccccagc aggcagaagt atgcaaagca tgcatctcaa ttagtcagca    3060
accaggtgtg gaaagtcccc aggctcccca gcaggcagaa gtatgcaaag catgcatctc    3120
aattagtcag caaccatagt cccgcccta actccgccca tcccgcccct aactccgccc     3180
agttccgccc attctccgcc ccatggctga ctaattttt ttatttatgc agaggccgag    3240
gccgcctctg cctctgagct attccagaag tagtgaggag gcttttttgg aggcctaggc    3300
ttttgcaaaa agctcccggg agcttgtata tccattttcg gatctgatca agagacagga    3360
tgaggatcgt ttcgcatgat tgaacaagat ggattgcacg caggttctcc ggccgcttgg    3420
gtggagaggc tattcggcta tgactgggca caacagacaa tcggctgctc tgatgccgcc    3480
gtgttccggc tgtcagcgca ggggcgcccg gttcttttg tcaagaccga cctgtccggt    3540
gccctgaatg aactgcagga cgaggcagcg cggctatcgt ggctggccac gacgggcgtt    3600
ccttgcgcag ctgtgctcga cgttgtcact gaagcgggaa gggactggct gctattgggc    3660
gaagtgccgg ggcaggatct cctgtcatct caccttgctc ctgccgagaa agtatccatc    3720
atggctgatg caatgcggcg gctgcatacg cttgatccgg ctacctgccc attcgaccac    3780
caagcgaaac atcgcatcga gcgagcacgt actcggatgg aagccggtct tgtcgatcag    3840
gatgatctgg acgaagagca tcaggggctc gcgccagccg aactgttcgc caggctcaag    3900
gcgcgcatgc ccgacggcga ggatctcgtc gtgacccatg gcgatgcctg cttgccgaat    3960
atcatggtgg aaaatggccg cttttctgga ttcatcgact gtggccggct gggtgtggcg    4020
gaccgctatc aggacatagc gttggctacc cgtgatattg ctgaagagct tggcggcgaa    4080
tgggctgacc gcttcctcgt gctttacggt atcgccgctc ccgattcgca gcgcatcgcc    4140
ttctatcgcc ttcttgacga gttcttctga gcgggactct ggggttcgaa atgaccgacc    4200
aagcgacgcc caacctgcca tcacgagatt tcgattccac cgccgccttc tatgaaaggt    4260
tgggcttcgg aatcgttttc cgggacgccg gctggatgat cctccagcgc ggggatctca    4320
tgctggagtt cttcgcccac cccaacttgt ttattgcagc ttataatggt tacaaataaa    4380
gcaatagcat cacaaatttc acaaataaag catttttttc actgcattct agttgtggtt    4440
tgtccaaact catcaatgta tcttatcatg tctgtatacc gtcgacctct agctagagct    4500
tggcgtaatc atggtcatag ctgtttcctg tgtgaaattg ttatccgctc acaattccac    4560
acaacatacg agccggaagc ataaagtgta aagcctgggg tgcctaatga gtgagctaac    4620
tcacattaat tgcgttgcgc tcactgcccg ctttccagtc gggaaacctg tcgtgccagc    4680
tgcattaatg aatcggccaa cgcgcgggga gaggcggttt gcgtattggg cgctcttccg    4740
cttcctcgct cactgactcg ctgcgctcgg tcgttcggct gcggcgagcg gtatcagctc    4800
actcaaaggc ggtaatacgg ttatccacag aatcagggga taacgcagga aagaacatgt    4860
gagcaaaagg ccagcaaaag gccaggaacc gtaaaaaggc cgcgttgctg gcgttttttcc    4920 ataggctccg cccccctgac gagcatcaca aaaatcgacg ctcaagtcag aggtggcgaa    4980
acccgacagg actataaaga taccaggcgt ttccccctgg aagctccctc gtgcgctctc    5040
ctgttccgac cctgccgctt accggatacc tgtccgcctt tctcccttcg ggaagcgtgg    5100
cgctttctca tagctcacgc tgtaggtatc tcagttcggt gtaggtcgtt cgctccaagc    5160
tgggctgtgt gcacgaaccc cccgttcagc ccgaccgctg cgccttatcc ggtaactatc    5220
gtcttgagtc aacccggta agacacgact tatcgccact ggcagcagcc actggtaaca    5280
```

```
ggattagcag agcgaggtat gtaggcggtg ctacagagtt cttgaagtgg tggcctaact      5340
acggctacac tagaagaaca gtatttggta tctgcgctct gctgaagcca gttaccttcg      5400
gaaaaagagt tggtagctct tgatccggca acaaaccac cgctggtagc ggttttttg       5460
tttgcaagca gcagattacg cgcagaaaaa aaggatctca agaagatcct ttgatctttt     5520
ctacggggtc tgacgctcag tggaacgaaa actcacgtta agggattttg gtcatgagat     5580
tatcaaaaag gatcttcacc tagatccttt taaattaaaa atgaagtttt aaatcaatct     5640
aaagtatata tgagtaaact tggtctgaca gttaccaatg cttaatcagt gaggcaccta     5700
tctcagcgat ctgtctattt cgttcatcca tagttgcctg actccccgtc gtgtagataa     5760
ctacgatacg ggagggctta ccatctggcc ccagtgctgc aatgataccg cgagacccac     5820
gctcaccggc tccagattta tcagcaataa accagccagc cggaagggcc gagcgcagaa     5880
gtggtcctgc aactttatcc gcctccatcc agtctattaa ttgttgccgg gaagctagag     5940
taagtagttc gccagttaat agtttgcgca acgttgttgc cattgctaca ggcatcgtgg     6000
tgtcacgctc gtcgtttggt atggcttcat tcagctccgg ttcccaacga tcaaggcgag     6060
ttacatgatc ccccatgttg tgcaaaaaag cggttagctc cttcggtcct ccgatcgttg     6120
tcagaagtaa gttggccgca gtgttatcac tcatggttat ggcagcactg cataattctc     6180
ttactgtcat gccatccgta agatgctttt ctgtgactgg tgagtactca accaagtcat     6240
tctgagaata gtgtatgcgg cgaccgagtt gctcttgccc ggcgtcaata cgggataata     6300
ccgcgccaca tagcagaact ttaaaagtgc tcatcattgg aaaacgttct tcggggcgaa     6360
aactctcaag gatcttaccg ctgttgagat ccagttcgat gtaacccact cgtgcaccca     6420
actgatcttc agcatctttt actttcacca gcgtttctgg gtgagcaaaa acaggaaggc     6480
aaaatgccgc aaaaaaggga ataagggcga cacggaaatg ttgaatactc atactcttcc     6540
tttttcaata ttattgaagc atttatcagg gttattgtct catgagcgga tacatatttg     6600
aatgtattta gaaaaataaa caaataggggg ttccgcgcac atttccccga aaagtgccac     6660
ctgacgtc                                                              6668
```

<210> SEQ ID NO 216
<211> LENGTH: 5959
<212> TYPE: DNA
<213> ORGANISM: Homo sapiens

<400> SEQUENCE: 216

```
gacggatcgg gagatctccc gatccctat ggtgcactct cagtacaatc tgctctgatg       60
ccgcatagtt aagccagtat ctgctccctg cttgtgtgtt ggaggtcgct gagtagtgcg      120
cgagcaaaat ttaagctaca acaaggcaag gcttgaccga caattgcatg aagaatctgc      180
ttagggttag gcgttttgcg ctgcttcgcg atgtacgggc cagatatacg cgttgacatt      240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggag tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
tcgctattac catggtgatg cggttttggc agtacatcaa tgggcgtgga tagcggtttg     660
```

```
actcacgggg atttccaagt ctccacccca ttgacgtcaa tgggagtttg ttttggcacc    720
aaaatcaacg ggactttcca aaatgtcgta caactccgc cccattgacg caaatgggcg     780
gtaggcgtgt acggtgggag gtctatataa gcagagctct ctggctaact agagaaccca   840
ctgcttactg gcttatcgaa attaatacga ctcactatag ggagacccaa gctggctagc   900
gtttaaactt aagcttggca atccggtact gttggtaaag ccaccatggt gaccggctac   960
cggctgttcg aggagattct cgggagttcc ggtggtggcg ggagcggagg tggaggctcg   1020
agcggtggag ctcaggggaa ttcatatgct tccaccaggc cccctacctt gtcaccaata   1080
cctcacattc ctcgaagccc ttacaagttt cctagttcac ccttacggat tcctggaggg   1140
aacatctata tttcacccct gaagagtcca tataaatttt cagaaggtct gccaacacca   1200
acaaaaatga ctccaagatc aagaatctta gtatcaattg gtgaatcatt cgggacttct   1260
gagaagttcc agaaaataaa tcagatggta tgtaacagcg accgtgtgct caaaagaagt   1320
gctgaaggaa gcaaccctcc taaaccactg aaaaaactac gctttgatat tgaaggatca   1380
gatgaagcag atggaagtaa acatctccca ggagagtcca aatttcagca gaaactggca   1440
gaaatgactt ctactcgaac acgaatgcaa aagcagaaaa tgaatgatag catggatacc   1500
tcaaacaagg aagagaaata atctagaggg cccgtttaaa cccgctgatc agcctcgact   1560
gtgccttcta gttgccagcc atctgttgtt tgccctcccc ccgtgccttc cttgaccctg   1620
gaaggtgcca ctcccactgt cctttcctaa taaaatgagg aaattgcatc gcattgtctg   1680
agtaggtgtc attctattct ggggggtggg gtggggcagg acagcaaggg ggaggattgg   1740
gaagacaata gcaggcatgc tggggatgcg gtgggctcta tggcttctga gcggaaaga   1800 accagctggg gctctagggg gtatccccac gcgccctgta gcggcgcatt aagcgcggcg   1860 ggtgtgtgg ttacgcgcag cgtgaccgct acacttgcca gcgccctagc gcccgctcct   1920
ttcgctttct tcccttcctt tctcgccacg ttcgccggct ttccccgtca agctctaaat   1980
cgggggctcc ctttagggtt ccgatttagt gctttacggc acctcgaccc caaaaaactt   2040
gattagggtg atggttcacg tagtgggcca tcgccctgat agacggtttt tcgccctttg   2100
acgttggagt ccacgttctt taatagtgga ctcttgttcc aaactggaac aacactcaac   2160
cctatctcgg tctattcttt tgatttataa gggattttgc cgatttcggc ctattggtta   2220
aaaaatgagc tgatttaaca aaaatttaac gcgaattaat tctgtggaat gtgtgtcagt   2280
tagggtgtgg aaagtcccca ggctccccag caggcagaag tatgcaaagc atgcatctca   2340
attagtcagc aaccaggtgt ggaaagtccc caggctcccc agcaggcaga agtatgcaaa   2400
gcatgcatct caattagtca gcaaccatag tcccgcccct aactccgccc atcccgcccc   2460
taactccgcc cagttccgcc cattctccgc cccatggctg actaattttt tttatttatg   2520
cagaggccga ggccgcctct gcctctgagc tattccagaa gtagtgagga ggcttttttg   2580
gaggcctagg cttttgcaaa aagctcccgg gagcttgtat atccattttc ggatctgatc   2640
aagagacagg atgaggatcg tttcgcatga ttgaacaaga tggattgcac gcaggttctc   2700
cggccgcttg ggtggagagg ctattcggct atgactgggc acaacagaca atcggctgct   2760
ctgatgccgc cgtgttccgg ctgtcagcgc aggggcgccc ggttcttttt gtcaagaccg   2820
acctgtccgg tgccctgaat gaactgcagg acgaggcagc gcggctatcg tggctggcca   2880
cgacgggcgt tccttgcgca gctgtgctcg acgttgtcac tgaagcggga agggactggc   2940
tgctattggg cgaagtgccg gggcaggatc tcctgtcatc tcaccttgct cctgccgaga   3000
aagtatccat catggctgat gcaatgcggc ggctgcatac gcttgatccg gctacctgcc   3060
```

```
cattcgacca ccaagcgaaa catcgcatcg agcgagcacg tactcggatg gaagccggtc   3120
ttgtcgatca ggatgatctg gacgaagagc atcaggggct cgcgccagcc gaactgttcg   3180
ccaggctcaa ggcgcgcatg cccgacggcg aggatctcgt cgtgacccat ggcgatgcct   3240
gcttgccgaa tatcatggtg gaaaatggcc gcttttctgg attcatcgac gtggccggc    3300 tgggtgtggc ggaccgctat caggacatag cgttggctac ccgtgatatt gctgaagagc   3360
ttggcggcga atgggctgac cgcttcctcg tgctttacgg tatcgccgct cccgattcgc   3420
agcgcatcgc cttctatcgc cttcttgacg agttcttctg agcgggactc tggggttcga   3480
aatgaccgac caagcgacgc ccaacctgcc atcacgagat ttcgattcca ccgccgcctt   3540
ctatgaaagg ttgggcttcg gaatcgtttt ccgggacgcc ggctggatga tcctccagcg   3600
cggggatctc atgctggagt tcttcgccca ccccaacttg tttattgcag cttataatgg   3660
ttacaaataa agcaatagca tcacaaattt cacaaataaa gcatttttt cactgcattc    3720 tagttgtggt ttgtccaaac tcatcaatgt atcttatcat gtctgtatac cgtcgacctc   3780
tagctagagc ttggcgtaat catggtcata gctgtttcct gtgtgaaatt gttatccgct   3840
cacaattcca cacaacatac gagccggaag cataaagtgt aaagcctggg gtgcctaatg   3900
agtgagctaa ctcacattaa ttgcgttgcg ctcactgccc gctttccagt cgggaaacct   3960
gtcgtgccag ctgcattaat gaatcggcca acgcgcgggg agaggcggtt tgcgtattgg   4020
gcgctcttcc gcttcctcgc tcactgactc gctgcgctcg gtcgttcggc tgcggcgagc   4080
ggtatcagct cactcaaagg cggtaatacg gttatccaca gaatcagggg ataacgcagg   4140
aaagaacatg tgagcaaaag gccagcaaaa ggccaggaac cgtaaaaagg ccgcgttgct   4200
ggcgtttttc cataggctcc gcccccctga cgagcatcac aaaaatcgac gctcaagtca   4260
gaggtggcga aacccgacag gactataaag ataccaggcg tttccccctg gaagctccct   4320
cgtgcgctct cctgttccga ccctgccgct taccggatac ctgtccgcct ttctcccttc   4380
gggaagcgtg gcgctttctc atagctcacg ctgtaggtat ctcagttcgg tgtaggtcgt   4440
tcgctccaag ctgggctgtg tgcacgaacc ccccgttcag cccgaccgct gcgccttatc   4500
cggtaactat cgtcttgagt ccaacccggt aagacacgac ttatcgccac tggcagcagc   4560
cactggtaac aggattagca gagcgaggta tgtaggcggt gctacagagt tcttgaagtg   4620
gtggcctaac tacggctaca ctagaagaac agtatttggt atctgcgctc tgctgaagcc   4680
agttaccttc ggaaaaagag ttggtagctc ttgatccggc aaacaaacca ccgctggtag   4740 cggtttttt gtttgcaagc agcagattac gcgcagaaaa aaggatctc aagaagatcc    4800 tttgatcttt tctacggggt ctgacgctca gtggaacgaa aactcacgtt aagggatttt   4860
ggtcatgaga ttatcaaaaa ggatcttcac ctagatcctt ttaaattaaa aatgaagttt   4920
taaatcaatc taaagtatat atgagtaaac ttggtctgac agttaccaat gcttaatcag   4980
tgaggcacct atctcagcga tctgtctatt tcgttcatcc atagttgcct gactccccgt   5040
cgtgtagata actacgatac gggagggctt accatctggc cccagtgctg caatgatacc   5100
gcgagaccca cgctcaccgg ctccagattt atcagcaata aaccagccag ccggaagggc   5160
cgagcgcaga agtggtcctg caactttatc cgcctccatc cagtctatta attgttgccg   5220
ggaagctaga gtaagtagtt cgccagttaa tagtttgcgc aacgttgttg ccattgctac   5280
aggcatcgtg gtgtcacgct cgtcgtttgg tatggcttca ttcagctccg gttcccaacg   5340
atcaaggcga gttacatgat cccccatgtt gtgcaaaaaa gcggttagct ccttcggtcc   5400
```

```
tccgatcgtt gtcagaagta agttggccgc agtgttatca ctcatggtta tggcagcact    5460
gcataattct cttactgtca tgccatccgt aagatgcttt tctgtgactg gtgagtactc    5520
aaccaagtca ttctgagaat agtgtatgcg gcgaccgagt tgctcttgcc cggcgtcaat    5580
acgggataat accgcgccac atagcagaac tttaaaagtg ctcatcattg gaaaacgttc    5640 ttcgggcga aaactctcaa ggatcttacc gctgttgaga tccagttcga tgtaacccac    5700
tcgtgcaccc aactgatctt cagcatcttt tactttcacc agcgtttctg ggtgagcaaa    5760
aacaggaagg caaaatgccg caaaaaaggg aataagggcg acacggaaat gttgaatact    5820
catactcttc ctttttcaat attattgaag catttatcag ggttattgtc tcatgagcgg    5880
atacatattt gaatgtattt agaaaaataa acaaataggg gttccgcgca catttccccg    5940
aaaagtgcca cctgacgtc                                                 5959
```

<210> SEQ ID NO 217
<211> LENGTH: 8664
<212> TYPE: DNA
<213> ORGANISM: Homo sapiens

<400> SEQUENCE: 217

```
gacggatcgg gagatctccc gatccctat ggtgcactct cagtacaatc tgctctgatg      60
ccgcatagtt aagccagtat ctgctccctg cttgtgtgtt ggaggtcgct gagtagtgcg    120
cgagcaaaat ttaagctaca acaaggcaag cttgaccga caattgcatg aagaatctgc     180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta caactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaactt aagcttgcca ccatgccgcc caaaaccccc gaaaaacgg ccgccaccgc    960 cgccgctgcc gccgcggaac ccccggcacc gccgccgccg cccctcctg aggaggaccc    1020 agagcaggac agcggcccgg aggacctgcc tctcgtcagg cttgagtttg aagaaacaga    1080
agaacctgat tttactgcat tatgtcagaa attaaagata ccagatcatg tcagagagag    1140
agcttggtta acttgggaga aagtttcatc tgtggatgga gtattgggag ttatattca     1200 aaagaaaaag gaactgtggg gaatctgtat ctttattgca gcagttgacc tagatgagat    1260
gtcgttcact tttactgagc tacagaaaaa catagaaatc agtgtccata aattctttaa    1320
cttactaaaa gaaattgata ccagtaccaa agttgataat gctatgtcaa gactgttgaa    1380
gaagtatgat gtattgtttg cactcttcag caaattggaa aggacatgtg aacttatata    1440
tttgacacaa cccagcagtt cgatatctac tgaaataaat tctgcattgg tgctaaaagt    1500
ttcttggatc acatttttat tagctaaagg ggaagtatta caaatggaag atgatctggt    1560
```

```
gatttcattt cagttaatgc tatgtgtcct tgactatttt attaaactct cacctcccat    1620
gttgctcaaa gaaccatata aaacagctgt tatacccatt aatggttcac ctcgaacacc    1680
caggcgaggt cagaacagga gtgcacggat agcaaaacaa ctagaaaatg atacaagaat    1740
tattgaagtt ctctgtaaag aacatgaatg taatatagat gaggtgaaaa atgtttattt    1800
caaaaatttt atacctttta tgaattctct tggacttgta acatctaatg acttccaga    1860 ggttgaaaat ctttctaaac gatacgaaga aatttatctt aaaaataaag atctagatgc    1920
aagattattt ttggatcatg ataaaactct tcagactgat tctatagaca gttttgaaac    1980
acagagaaca ccacgaaaaa gtaaccttga tgaagaggtg aatgtaattc ctccacacac    2040
tccagttagg actgttatga acactatcca acaattaatg atgattttaa attcagcaag    2100
tgatcaacct tcagaaaatc tgatttccta ttttaacaac tgcacagtga atccaaaaga    2160
aagtatactg aaaagagtga aggatatagg atacatcttt aaagagaaat tgctaaagc    2220 tgtgggacag ggttgtgtcg aaattggatc acagcgatac aaacttggag ttcgcttgta    2280
ttaccgagta atggaatcca tgcttaaatc agaagaagaa cgattatcca ttcaaaattt    2340
tagcaaactt ctgaatgaca acatttttca tatgtcttta ttggcgtgcg ctcttgaggt    2400
tgtaatggcc acatatagca gaagtacatc tcagaatctt gattctggaa cagatttgtc    2460
tttcccatgg attctgaatg tgcttaattt aaaagccttt gattttaca aagtgatcga    2520 aagttttatc aaagcagaag gcaacttgac aagagaaatg ataaaacatt tagaacgatg    2580
tgaacatcga atcatggaat cccttgcatg gctctcagat tcacctttat ttgatcttat    2640
taaacaatca aaggaccgag aaggaccaac tgatcacctt gaatctgctt gtcctcttaa    2700
tcttcctctc cagaataatc acactgcagc agatatgtat ctttctcctg taagatctcc    2760
aaagaaaaaa ggttcaacta cgcgtgtaaa ttctactgca aatgcagaga cacaagcaac    2820
ctcagccttc cagacccaga agccattgaa atctacctct ctttcactgt tttataaaaa    2880
agtgtatcgg ctagcctatc tccggctaaa tacactttgt gaacgccttc tgtctgagca    2940
cccagaatta gaacatatca tctgaccct tttccagcac accctgcaga atgagtatga    3000
actcatgaga gacaggcatt tggaccaaat tatgatgtgt ccatgtatg gcatatgcaa    3060 agtgaagaat atagacccta aattcaaaat cattgtaaca gcatacaagg atcttcctca    3120
tgctgttcag gagacattca aacgtgtttt gatcaaagaa gaggagtatg attctattat    3180
agtattctat aactcggtct tcatgcagag actgaaaaca aatattttgc agtatgcttc    3240
caccaggccc cctaccttgt caccaatacc tcacattcct cgaagccctt acaagtttcc    3300 tagttcacccc ttacggattc ctggagggaa catctatatt tcacccctga agagtccata    3360
taaaatttca gaaggtctgc caacaccaac aaaaatgact ccaagatcaa gaatcttagt    3420
atcaattggt gaatcattcg ggacttctga aagttccag aaaataaatc agatggtatg    3480
taacagcgac cgtgtgctca aaagaagtgc tgaaggaagc aaccctccta aaccactgaa    3540
aaaactacgc tttgatattg aaggatcaga tgaagcagat ggaagtaaac atctcccagg    3600
agagtccaaa tttcagcaga aactggcaga atgacttct actcgaacac gaatgcaaaa    3660
gcagaaaatg aatgatagca tggataccct aaacaaggaa gagaaactcg agcggtggtg    3720
gcgggagcgg aggtggaggg tcgtcaggtg tcttcacact cgaagatttc gttggggact    3780
gggaacagac agccgcctac aacctggacc aagtccttga acagggaggt gtgtccagtt    3840
tgctgcagaa tctcgccgtg tccgtaactc cgatccaaag gattgtccgg agcggtgaaa    3900
```

```
atgccctgaa gatcgacatc catgtcatca tcccgtatga aggtctgagc gccgaccaaa    3960
tggcccagat cgaagaggtg tttaaggtgg tgtaccctgt ggatgatcat cactttaagg    4020
tgatcctgcc ctatggcaca ctggtaatcg acggggttac gccgaacatg ctgaactatt    4080
tcggacggcc gtatgaaggc atcgccgtgt tcgacggcaa aaagatcact gtaacaggga    4140
ccctgtggaa cggcaacaaa attatcgacg agcgcctgat caccccgac ggctccatgc     4200
tgttccgagt aaccatcaac agctaatcta gagggcccgt ttaaacccgc tgatcagcct    4260
cgactgtgcc ttctagttgc cagccatctg ttgtttgccc ctcccccgtg ccttccttga    4320
ccctggaagg tgccactccc actgtccttt cctaataaaa tgaggaaatt gcatcgcatt    4380
gtctgagtag gtgtcattct attctggggg gtggggtggg gcaggacagc aaggggagg     4440
attgggaaga caatagcagg catgctgggg atgcggtggg ctctatggct tctgaggcgg    4500
aaagaaccag ctgggctct aggggtatc cccacgcgcc ctgtagcggc gcattaagcg      4560
cggcgggtgt ggtggttacg cgcagcgtga ccgctacact tgccagcgcc ctagcgcccg    4620
ctcctttcgc tttcttccct tcctttctcg ccacgttcgc cggctttccc cgtcaagctc    4680
taaatcgggg gctcccttta gggttccgat ttagtgcttt acggcacctc gaccccaaaa    4740
aacttgatta gggtgatggt tcacgtagtg gccatcgcc ctgatagacg ttttttcgcc     4800
ctttgacgtt ggagtccacg ttctttaata gtggactctt gttccaaact ggaacaacac    4860
tcaaccctat ctcggtctat tcttttgatt tataagggat tttgccgatt tcggcctatt    4920
ggttaaaaaa tgagctgatt taacaaaaat ttaacgcgaa ttaattctgt ggaatgtgtg    4980
tcagttaggg tgtggaaagt ccccaggctc cccagcaggc agaagtatgc aaagcatgca    5040
tctcaattag tcagcaacca ggtgtggaaa gtccccaggc tccccagcag cagaagtat    5100
gcaaagcatg catctcaatt agtcagcaac catagtcccg cccctaactc cgcccatccc    5160
gcccctaact ccgcccagtt ccgcccattc tccgccccat ggctgactaa ttttttttat    5220
ttatgcagag gccgaggccg cctctgcctc tgagctattc cagaagtagt gaggaggctt    5280
ttttggaggc ctaggctttt gcaaaaagct cccgggagct tgtatatcca ttttcggatc    5340
tgatcaagag acaggatgag gatcgtttcg catgattgaa caagatggat tgcacgcagg    5400
ttctccggcc gcttgggtgg agaggctatt cggctatgac tgggcacaac agacaatcgg    5460
ctgctctgat gccgccgtgt tccggctgtc agcgcagggg cgcccggttc ttttgtcaa    5520
gaccgacctg tccggtgccc tgaatgaact gcaggacgag gcagcgcggc tatcgtggct    5580
ggccacgacg ggcgttcctt gcgcagctgt gctcgacgtt gtcactgaag cgggaaggga    5640
ctggctgcta ttgggcgaag tgccggggca ggatctcctg tcatctcacc ttgctcctgc    5700
cgagaaagta tccatcatgg ctgatgcaat gcggcggctg catacgcttg atccggctac    5760
ctgcccattc gaccaccaag cgaaacatcg catcgagcga gcacgtactc ggatggaagc    5820
cggtcttgtc gatcaggatg atctggacga agagcatcag gggctcgcgc cagccgaact    5880
gttcgccagg ctcaaggcgc gcatgcccga cggcgaggat ctcgtcgtga cccatggcga    5940
tgcctgcttg ccgaatatca tggtggaaaa tggccgcttt tctggattca tcgactgtgg    6000
ccggctgggt gtggcggacc gctatcagga catagcgttg ctacccgtg atattgctga     6060
agagcttggc ggcgaatggg ctgaccgctt cctcgtgctt tacggtatcg ccgctcccga    6120
ttcgcagcgc atcgccttct atcgccttct tgacgagttc ttctgagcgg gactctgggg    6180
ttcgaaatga ccgaccaagc gacgcccaac ctgccatcac gagatttcga ttccaccgcc    6240
gccttctatg aaaggttggg cttcggaatc gttttccggg acgccggctg gatgatcctc    6300
```

| | |
|---|---|
| cagcgcgggg atctcatgct ggagttcttc gcccacccca acttgtttat tgcagcttat | 6360 |
| aatggttaca aataaagcaa tagcatcaca aatttcacaa ataaagcatt tttttcactg | 6420 |
| cattctagtt gtggtttgtc caaactcatc aatgtatctt atcatgtctg tataccgtcg | 6480 |
| acctctagct agagcttggc gtaatcatgg tcatagctgt ttcctgtgtg aaattgttat | 6540 |
| ccgctcacaa ttccacacaa catacgagcc ggaagcataa agtgtaaagc ctggggtgcc | 6600 |
| taatgagtga gctaactcac attaattgcg ttgcgctcac tgcccgcttt ccagtcggga | 6660 |
| aacctgtcgt gccagctgca ttaatgaatc ggccaacgcg ggggagagg cggtttgcgt | 6720 |
| attgggcgct cttccgcttc ctcgctcact gactcgctgc gctcggtcgt tcggctgcgg | 6780 |
| cgagcggtat cagctcactc aaaggcggta atacggttat ccacagaatc aggggataac | 6840 |
| gcaggaaaga acatgtgagc aaaaggccag caaaaggcca ggaaccgtaa aaaggccgcg | 6900 |
| ttgctggcgt ttttccatag gctccgcccc cctgacgagc atcacaaaaa tcgacgctca | 6960 |
| agtcagaggt ggcgaaaccc gacaggacta taaagatacc aggcgtttcc ccctggaagc | 7020 |
| tccctcgtgc gctctcctgt tccgaccctg ccgcttaccg gatacctgtc cgcctttctc | 7080 |
| ccttcgggaa gcgtggcgct ttctcatagc tcacgctgta ggtatctcag ttcggtgtag | 7140 |
| gtcgttcgct ccaagctggg ctgtgtgcac gaaccccccg ttcagcccga ccgctgcgcc | 7200 |
| ttatccggta actatcgtct tgagtccaac ccggtaagac acgacttatc gccactggca | 7260 |
| gcagccactg gtaacaggat tagcagagcg aggtatgtag gcggtgctac agagttcttg | 7320 |
| aagtggtggc ctaactacgg ctacactaga agaacagtat ttggtatctg cgctctgctg | 7380 |
| aagccagtta ccttcggaaa aagagttggt agctcttgat ccggcaaaca aaccaccgct | 7440 |
| ggtagcggtt ttttgtttg caagcagcag attacgcgca gaaaaaaagg atctcaagaa | 7500 |
| gatcctttga tcttttctac ggggtctgac gctcagtgga acgaaaactc acgttaaggg | 7560 |
| attttggtca tgagattatc aaaaaggatc ttcacctaga tccttttaaa ttaaaaatga | 7620 |
| agttttaaat caatctaaag tatatatgag taaacttggt ctgacagtta ccaatgctta | 7680 |
| atcagtgagg cacctatctc agcgatctgt ctatttcgtt catccatagt tgcctgactc | 7740 |
| cccgtcgtgt agataactac gatacgggag ggcttaccat ctggccccag tgctgcaatg | 7800 |
| ataccgcgag acccacgctc accggctcca gatttatcag caataaacca gccagcggaa | 7860 |
| agggccgagc gcagaagtgg tcctgcaact ttatccgcct ccatccagtc tattaattgt | 7920 |
| tgccgggaag ctagagtaag tagttcgcca gttaatagtt tgcgcaacgt tgttgccatt | 7980 |
| gctacaggca tcgtggtgtc acgctcgtcg tttggtatgg cttcattcag ctccggttcc | 8040 |
| caacgatcaa ggcgagttac atgatccccc atgttgtgca aaaaagcggt tagctccttc | 8100 |
| ggtcctccga tcgttgtcag aagtaagttg gccgcagtgt tatcactcat ggttatggca | 8160 |
| gcactgcata attctcttac tgtcatgcca tccgtaagat gcttttctgt gactggtgag | 8220 |
| tactcaacca agtcattctg agaatagtgt atgcggcgac cgagttgctc ttgcccggcg | 8280 |
| tcaatacggg ataataccgc gccacatagc agaactttaa aagtgctcat cattggaaaa | 8340 |
| cgttcttcgg ggcgaaaact ctcaaggatc ttaccgctgt tgagatccag ttcgatgtaa | 8400 |
| cccactcgtg cacccaactg atcttcagca tcttttactt tcaccagcgt ttctgggtga | 8460 |
| gcaaaaacag gaaggcaaaa tgccgcaaaa aagggaataa gggcgacacg gaaatgttga | 8520 |
| atactcatac tcttcctttt tcaatattat tgaagcattt atcagggtta ttgtctcatg | 8580 |

```
agcggataca tatttgaatg tatttagaaa aataaacaaa taggggttcc gcgcacattt    8640
ccccgaaaag tgccacctga cgtc                                          8664
```

CELL-BASED ASSAY FOR DETERMINING ACTIVITY IN THE RETINOBLASTOMA PATHWAY

CROSS REFERENCE TO RELATED APPLICATION

This application is a continuation of co-pending U.S. application Ser. No. 16/192,993 filed on Nov. 11, 2018. U.S. Ser. No. 16/192,993 claimed the benefit of Provisional Application No. 62/587,107 filed on Nov. 16, 2017 and Provisional Application No. 62/756,750 filed on Nov. 7, 2018. The entirety of each application is incorporated herein by reference.

FIELD OF THE INVENTION

The present invention generally relates to a cell-based assay useful for determining the activity of CDK4, CDK6, Rb, and p16, and their respective variants. The novel cell-based assay is useful in screening CDK4 and CDK6 inhibitors and predicting patient response to treatment with CDK targeted inhibitors.

BACKGROUND OF THE INVENTION

The cyclin-dependent kinases are serine/threonine protein kinases which are the driving force behind the cell cycle and cell proliferation. Specifically, CDK4 and CDK6 (CDK4/6) is a catalytic subunit of the protein kinase complex that is important for cell cycle G1 phase progression. The activity of this kinase is restricted to the G1-S phase, which is controlled by the regulatory subunits D-type cyclins and CDK inhibitor p16. An additional protein in the cell cycle is the retinoblastoma (Rb) protein (a negative regulator and tumor suppressor). Rb protein also leads to transcriptional activation in the cell and the eventual progression into S phase. (Phadke and Thomas, OncLive, October 2014). In general, activated CDKs mediate regulatory functions by phosphorylating cellular proteins, usually on serine or threonine residues. Uncontrolled proliferation is a hallmark of cancer cells, and misregulation of CDK function occurs in a variety of solid tumors. CDK4/6 are of particular interest because the associated activities are frequently misregulated in a wide variety of cancers.

CDK4/6 act as a serine/threonine kinase that phosphorylates Rb. Naturally occurring Rb mutants lack the ability to bind to and regulate E2F (Qian et al., 1992). Binding of Rb to E2F1 inhibits eukaryotic E2F mediated transcription that is promoted through E2F activity. However, CDK-mediated phosphorylation of Rb dissociates Rb from E2F1, thereby allowing transcription to occur. When cells are lacking functional Rb they have tendency to be resistant to natural inhibitor p16 (Medema et al., 1995) and to CDK4 and/or CDK6 inhibitors (Sherr et al., 2016). When cells are treated with Palbociclib (Ribociclib or Abemaciclib) and CDK4/6 is inhibited, Rb phosphorylation is prevented and allows for the Rb/E2F1 complex that inhibits transcription and decreases the growth and replication of the cell, thereby inhibiting cancer cells. p16 is a natural inhibitor of CDK4 and CDK6 and as a result plays very important role in the CDK4/CDK6 pathway. When cells lack functional p16 they tend to be susceptible to cancer. CDKN2A (the gene which encodes p16 protein) somatic alterations occur in more than 50% of human tumors (including inherited mutations in melanoma and pancreatic carcinoma) and the majority of these mutations have only been observed in a single family. Since many somatic gene mutations in the Rb pathway will result in a "loss of function" protein, it is important to have a functional assay to determine where in the pathway the mutation is and how that specific mutant protein responds to treatment.

To treat complex diseases effectively, a systems-level approach is needed to understand the interplay of intracellular signals and cellular behaviors that underlie disease states. This approach requires high-throughput, multiplex techniques that measure quantitative temporal variations of multiple protein activities in the intracellular signaling network. Accordingly, there remains a need for a personalized medicine approach utilizing cell-based assays and methods to screen the efficacy of CDK4/6 inhibitors on individual patients to determine the best treatment for that individual patient.

SUMMARY OF THE INVENTION

In one aspect, the present invention concerns a method of determining the effect of a CDK inhibitor on a CDK variant, comprising the steps of:
  a. preparing a first cDNA of a CDK variant, wherein said CDK variant contains at least one mutation as compared to wild-type CDK;
  b. providing a mammalian cell, said cell comprising a knockout of endogenous CDK, and a first construct stably integrated into said mammalian cell, wherein said first construct comprises a second cDNA encoding E2F1 protein which is linked to Dp-1 protein and a first portion of a luciferase gene at its C-terminus;
  c. transfecting into said mammalian cell said first cDNA from step a);
  d. transfecting into said mammalian cell a third cDNA encoding Cyclin D1 and a second construct, comprising a fourth cDNA of encoding Rb protein which is linked to a second portion of a luciferase gene at its N-terminus, wherein when said first construct is in close proximity with said second construct a complex is formed that emits light;
  e. exposing said transfected cell with a CDK inhibitor; and
  f. measuring any generated light emission, wherein an increase in light emission relative to said CDK inhibitor is indicative of said CDK variant being susceptible to treatment with said CDK inhibitor.

In another aspect, the present invention concerns a method of determining the activity of a Rb variant in a cell, comprising the steps of:
  a. providing a mammalian cell, said cell comprising a stably integrated first construct, wherein said first construct comprises a first cDNA encoding E2F1 protein which is linked to a first portion of a luciferase gene, and a second cDNA encoding Dp-1 protein;
  b. preparing a linear third cDNA of a Rb variant, wherein said Rb variant contains at least one mutation as compared to wild-type Rb, and said third cDNA is linked to a second portion of a luciferase gene to form a second construct, wherein when said first construct is in close proximity with said second construct a complex is formed that emits light;
  c. transfecting said second construct into said mammalian cell; and
  d. determining the activity of said Rb variant by measuring any generated light emission, wherein an increase in light emission relative to a control mammalian cell is indicative of said Rb variant activity.

In another aspect, the present invention concerns a method of determining the activity of a p16 variant in a cell comprising the steps of:
a. providing a mammalian cell, said cell having a knockout of endogenous CDK4 and endogenous CDK6, and a first construct stably integrated into said mammalian cell comprising a first cDNA encoding E2F1 protein linked to Dp-1 protein and a first portion of a luciferase gene at its C-terminus;
b. preparing a second construct comprising a second cDNA encoding Rb protein which is linked to a second portion of a luciferase gene at its N-terminus, wherein when said first construct is in close proximity with said second construct a complex is formed that emits light;
c. preparing a third cDNA encoding Cyclin D1 protein and a fourth cDNA encoding CDK4 protein or CDK6 protein;
d. preparing a fifth cDNA of a CDKN2A variant, said CDKN2A variant having at least one mutation as compared to wild-type CDKN2A;
e. preparing a transfection complex, said transfection complex comprising said second construct, said third cDNA, said fourth cDNA, and said fifth cDNA;
f. transfecting said transfection complex into said mammalian cell, wherein said transfection is transient; and
g. determining the activity of said p16 variant by measuring any generated light emission, wherein an increase in light emission relative to a mammalian cell control is indicative of said p16 variant activity.

In another aspect, the present invention concerns a method of determining the sensitivity of a CDK4 variant or a CDK6 variant to p16 in a cell, comprising the steps of:
a. providing a mammalian cell, said cell having a knockout of endogenous CDK4 and endogenous CDK6, and a first construct stably integrated into said cell, said first construct comprising a first cDNA encoding E2F1 protein linked to Dp-1 protein, wherein said Dp1 protein is linked to a first portion of a luciferase gene at its C-terminus;
b. preparing a second cDNA of a CDK4 or CDK6 variant from a patient, said CDK4 variant or CDK6 variant containing at least one mutation as compared to wild-type CDK4 or wild-type CDK6;
c. preparing a second construct comprising a third cDNA encoding Rb protein which is linked to a second portion of a luciferase gene at its N-terminus, wherein when said first construct is in close proximity with said second construct a complex is formed that emits light;
d. preparing a fourth cDNA encoding Cyclin D1 protein;
e. preparing a fifth cDNA of wild-type CDKN2A;
f. preparing a transfection complex comprising said second construct, said third cDNA, said fourth cDNA, and said fifth cDNA;
g. transfecting said transfection complex into said mammalian cell, wherein said transfection is transient; and
h. determining whether said CDK4 or CDK6 variant is sensitive to p16 by measuring any generated light emission, wherein an increase in light emission relative to a mammalian cell control is indicative of said CDK4 or CDK6 variant being sensitive to p16.

In another aspect, the present invention concerns a cell line comprising:
a. a first construct comprising a first cDNA encoding E2F1 protein which is linked to Dp-1 protein and a first portion of a luciferase gene at its C-terminus; and
b. a knockout of endogenous CDK4 and endogenous CDK6.

In another aspect, the present invention concerns a cell line comprising:
a. a first construct comprising a first cDNA encoding Dp-1 protein and a second cDNA encoding E2F1 protein which is linked to a first portion of a luciferase gene at its C-terminus; and
b. a knockout of endogenous CDK4 and endogenous CDK6.

BRIEF DESCRIPTION OF THE DRAWINGS

FIG. 3A, FIG. 3B and FIG. 3C show the nucleotide sequences of RB1, E2F1, and DP1 fragments used in the NanoBit assay. FIG. 3D, FIG. 3E and FIG. 3F show amino acid sequences of corresponding Rb, E2F1 and Dp-1 fragments used in the NanoBit assay.

DETAILED DESCRIPTION OF THE INVENTION

Figure 1:
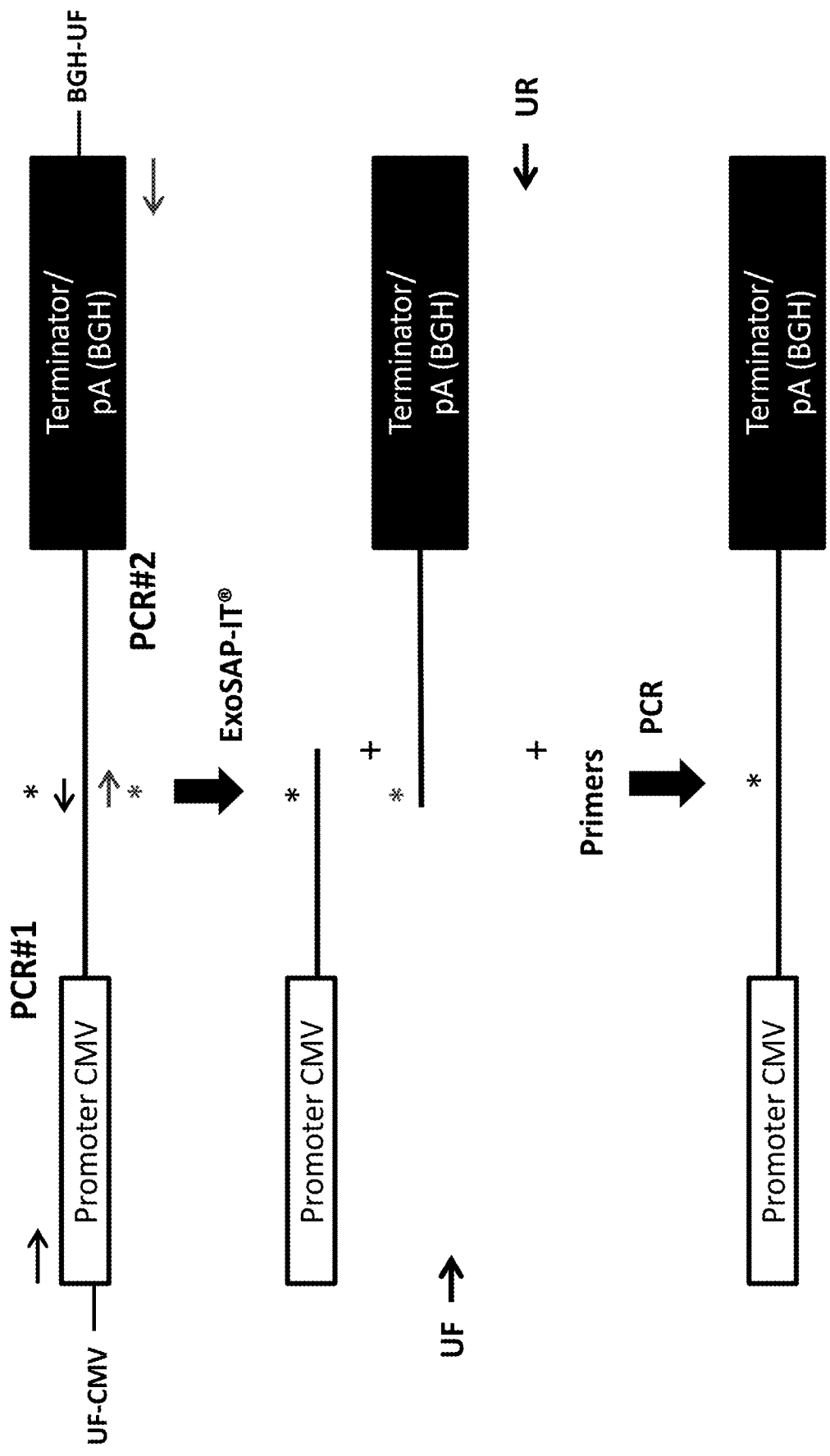
FIG. 1 shows a schematic representation of PCR-mediated overlapping extension method that has been used for all of the linear DNA constructs.

The present invention can be better understood from the following description of preferred embodiments, taken in conjunction with the accompanying drawings. It should be apparent to those skilled in the art that the described embodiments of the present invention provided herein are merely exemplary and illustrative and not limiting.

Definitions

Various terms used in this specification shall have the definitions set out herein.

As used herein, the term "A," "T," "C," and "G" refer to adenine, thymine, cytosine, and guanine as a nucleotide base, respectively.

As used herein, the terms "complement" or "complementation" refer to two halves of a protein coming into structural complex by binding to each other and producing a functional protein. "Complement" may also be used in reference to nucleic acids as in "reverse complement" to indicate an opposing strand of nucleic acids that resides in a particular sequence to bind to a polynucleotide.

As used herein, the term "CDK4" refers to the gene (SEQ. ID. NO: 1) which transcribes RNA that translates into the CDK4 protein.

As used herein, the term "CDK4" refers to cyclin-dependent kinase 4, also known as cell division protein kinase 4, which is an enzyme encoded by the CDK4 gene that phosphorylates Rb to advance cell cycle from G0 or G1 to S phase. CDK4 is a family member of the cyclin dependent kinase family.

As used herein, the term "CDK6" refers to the gene (SEQ. ID. NO: 2) which transcribes RNA that translates into the CDK6 protein.

As used herein, the term "CDK6" refers to cyclin-dependent kinase 6, also known as cell division protein kinase 6, which is an enzyme encoded by the CDK6 gene that phosphorylates Rb to advance cell cycle from G1 to S phase. CDK6 is a family member of the cyclin dependent kinase family.

As used herein, the term "p16" refers to cyclin-dependent kinase inhibitor 2A, which is a tumor suppressor protein that is encoded by the CDKN2A gene that decelerates cell progression from the G1 phase to the S phase.

As used herein, the term "CDKN2A" refers to the gene (SEQ. ID. NO: 3) which transcribes RNA that translates into the p16 protein.

As used herein, the term "Rb" refers to retinoblastoma protein which is a tumor suppressor protein, one function of which is to prevent cell growth by inhibiting cell cycle progression.

As used herein, the term "RB1" refers to the gene (SEQ. ID. NO: 4) which transcribes RNA that translates into the Rb protein.

As used herein, the term "E2F" refers to the family of transcription factors that form a complex with pRb. For purposes of this application, the term E2F includes E2F1, E2F2 and E2F3a, more specifically, E2F1.

As used herein, the term "E2F1" refers to the gene (SEQ. ID. NO: 5) which transcribes RNA that translates into the E2F1 protein.

As used herein, the term "DP1" refers to transcription factor DP-1 which is a protein that dimerizes with E2F factors to bind DNA as homodimers or heterodimers.

As used herein, the term "TFDP1" refers to the gene (SEQ. ID. NO: 6) which transcribes RNA that translates into the Dp-1 protein.

As used herein, the term "Cyclin D1" refers to the protein that complex with CDK4 to promote the passage of the cell through G1 phase by inhibiting pRb, allowing E2F transcription factors to transcribe genes required for S phase to begin.

As used herein, the term "CCND1" refers to the gene (SEQ. ID. NO: 7) which transcribes RNA that translates into the Cyclin D1 protein.

As used herein the term "wild-type" or "WT" is a term of the art understood by skilled persons and means the typical form of an organism, strain, gene or characteristic as it occurs in nature as distinguished from mutant, variant, or modified forms.

As used herein the term "variant" means the exhibition of qualities that have a pattern that deviates from what occurs in nature or is distinct from the predominant form that occurs in nature. For the purposes of this application, the term "variant" can refer to non-dominant gene sequences, mutations or changes in resulting amino acid sequence. For purposes of this application, when the gene name is used in reference to a variant, it refers to a variant found within the DNA. When a protein name is used in reference to a variant, it refers to a DNA change that result in a "variant" amino acid change that may alter protein characteristics.

As used herein, the term "functional variant" refers to variants in a protein's amino acid sequence that acts functionally like WT protein.

As used herein, the term "vehicle" refers to a solvent of a compound. For purposes of this application the term "vehicle" is used as a negative control in the absence of a compound.

As used herein, the term "reverse transfection" refers to the process by which cells are seeded at the same time DNA is transfected into the cell. In the reverse transfection process nucleic acid and transfection reagent complex is assembled in the tissue culture plate and the cells are then seeded into the walls of the plate.

As used herein, the term "transiently transfected" refers to biological cells within which an expression vector encoding a foreign gene has been introduced into the cell in order to express the gene. Transiently transfected genes do not integrate the foreign gene into their genome and accordingly the foreign gene will not be replicated. Transiently transfected cells express the foreign gene for a finite period of time.

As used herein, the term "fold change" refers to a measure describing how much a quantity changes going from an initial value corresponding to WT protein activity compared to the mutant activity.

As used herein, the term "CRISPR" refers to Clustered regularly interspaced short palindromic repeats, which are sequences used by CRISPR associated proteins (Cas9) for the purpose of recognizing and cutting genetic elements of polynucleotides. CRISPR/Cas9 uses sgRNA as a recognition sequence for identifying where the Cas9 will bind and cut the genetic element. For the purposes of the examples of this specification, CRISPR/Cas9 and sgRNA were used for genomic modifications of CDK4 and CDK6 genes.

As used herein, the term "sgRNA" refers to single-guide RNA used as a recognition sequence for the CRISPR/Cas9 binding.

As used herein, the term "CDK inhibitor" means any compound or agent that inhibits the activity of one or more CDK proteins or CDK/cyclin kinase complexes. The compound or agent may inhibit CDK4/6 activity by direct or indirect interaction with a CDK protein or it may act to prevent expression of one or more CDK genes.

As used herein, the term "HEK293" refers to an immortalized cell line derived from human embryonic kidney cells.

As used herein, the term "cancer" refers to a malignant neoplastic disease. Most cancers are characterized by hyperproliferation of a cell population.

As used herein, the term "luciferase activity" refers to the use of a luciferase protein or reporter to assess the amount of luciferase complementation resulting from two-parts or halves of a luciferase protein coming into complex or luciferase protein generated by transcriptional activity in a cell under the control of a promoter of interest. The activity is measured by addition of a substrate that binds to the luciferase protein and emits a light signal that can be measured using a luminometer.

As used herein, the term "promoter" refers to a region of the DNA that facilitates the transcription of a particular gene.

As used herein, the terms "NanoBiT," "Small BiT" and "Large BiT" refer to a split-luciferase complementation assay system consisting of two parts of a luciferase-based protein, where the Small BiT consists of 11 amino acids and the Large BiT consists of a 17.6 kDa protein. When the Small BiT and the Large BiT come into complex, the full luciferase is formed and can emit a light signal with the addition of a substrate.

As used herein, the terms "relative light units" or "RLU" refer to as the emitted light from a sample in a non-standardized scale as determined by a luminometer. The term "relative" indicates the units observed during the particular experiment and cannot be compared directly across experiments without standardization.

As used herein, the term "construct" refers to a plasmid or polynucleotide containing cDNA to encode for a given protein. As defined in the current application, the terms "first construct" and "second construct" refer to the complete plasmid and cDNA for encoding the expression of the protein linked to a portion of the luciferase gene. For the purposes of the current application, plasmids containing CRISPR/Cas9 and designed sgRNAs are also referred to as "constructs." "Constructs" can also refer to polynucleotides having the necessary components to express a desired protein.

The present invention relates to methods for determining the effect of a CDK inhibitor on CDK variants, determining activity of Rb variants, determining activity of p16 variants, and the effect of p16 on CDK variants. In one aspect, the present invention provides highly sensitive methods for determining whether a CDK variant is sensitive to treatment with a CDK inhibitor (e.g. Palbociclib, Ribociclib, Abemaciclib, etc.).

Methods include providing a stable cell system containing cDNA constructs with signaling capability to measure the functional interaction between CDK variants and treatment with a CDK inhibitor, the functional interaction between CDK variants and p16, the activity of Rb variants, and the activity of p16 variants. The variants (CDK, p16 or Rb) may include one or more mutations in the CDK4, CDK6, RB1, and CDKN2A genes.

In one aspect of the invention, variants in the CDK4 and CDK6 genes are identified, by next generation sequencing (NGS), as potentially hyperactive and/or Palbociclib (Ribociclib, Abemaciclib) resistant.

In one aspect, the present invention provides a method to determine the effect of a CDK inhibitor on a CDK variant using a cell based assay. The present cell based assay involves the use of a first cDNA that encodes the protein of a CDK variant. The first cDNA can encode a protein of a CDK4 variant or a CDK6 variant. The first cDNA is transfected into a cell. The cell having been prepared to contain a knockout of endogenous CDK. The cell can have a knockout of endogenous CDK4, endogenous CDK6, or both. In certain embodiments, the cell contains a stably integrated first construct. The first construct can contain a second cDNA encoding E2F1 protein which is linked to a Dp-1 protein and a first portion of a luciferase gene, preferably at the C-terminus. A third cDNA encoding the protein for Cyclin D1 is transfected into the cell. A second construct containing a fourth cDNA encoding the Rb protein linked to a second portion of a luciferase gene, preferably at its N-terminus, is transfected into the cell. Upon transfection, the first cDNA construct produces a protein of E2F1 linked to a protein of Dp-1 which has a first portion of a luciferase protein in the cell. Similarly, the second cDNA construct produces a protein encoding the protein for Rb which has a second portion of a luciferase protein in the cell. Upon exposure of the cell to a CDK inhibitor, the interaction between the two protein products promote generation of light emission and therefore the CDK variant susceptibility to treatment with the CDK inhibitor.

In another aspect, the present invention provides a method to determine the activity of the RB gene variants. In certain embodiments, the present cell based assay involves the use of a cell which has a stably integrated first construct that contains a first cDNA encoding E2F1 protein which is linked to a first portion of a luciferase gene. When the mutation in the RB gene, identified by NGS, is in the N-terminal part, from 1-378 aa, the full length Rb activity assay will be used. In this embodiment, the first construct is linked to the first portion of a luciferase gene preferably at its C-terminus. In certain embodiments, when the mutation in the RB gene occurs between 379-928 aa, the $Rb_{379-928}$ activity assay is implemented and the first construct is linked to the first portion of a luciferase gene preferably at its N-terminus. In certain embodiments, the first construct also contains a second cDNA encoding Dp-1 protein. In certain embodiments, a linear third cDNA encoding a Rb variant from a patient is prepared. Combinations of genetic modifications are also within the scope of the invention. In another embodiment, the third cDNA is linked to a second portion of a luciferase gene, preferably at its C-terminus to form a second construct. In another embodiment, the second construct transfected into the cell containing the stably integrated first construct. When the first construct and the second construct are in close proximity, a complex is formed that emits light. The protein product generated from the first construct interacts with the protein product generated from the second construct to produce a light emission upon the addition of a luciferase substrate. The present assay takes advantage of the interaction between E2F1-Dp-1 protein and the Rb variant protein. When the Rb and E2F1-Dp-1 proteins interact, a negative feedback system is created wherein light emission indicates a functional Rb variant. When Rb does not interact with E2F1-Dp-1 in the present cell assay, no light is produced, indicating a mutation in the Rb variant preventing phosphorylation of Rb by Cyclin D-CDK4/6. Accordingly, the Rb variant is determined as active when there is an increase in light emission relative to a control cell assay.

In another aspect, the present invention provides a method for determining the activity of p16 variant in a cell based assay. In certain embodiments, the assay cells have a knockout of endogenous CDK4, endogenous CDK6, or both endogenous CDK4 and endogenous CDK6. In certain embodiments, the cells have a first construct containing a first cDNA encoding E2F1 protein linked to Dp-1 protein and a portion of a luciferase gene, preferably at its C-terminus, (e.g. SEQ. ID. NO: 215) stably integrated into the cell. In another embodiment, a second construct comprising a second cDNA encoding Rb protein linked to a second portion of a luciferase gene, preferably at its N-terminus, (e.g., SEQ. ID. NO: 214) is prepared as part of a transfection complex. In another embodiment, a third cDNA encoding Cyclin D1 (e.g., SEQ. ID. NO: 7) and a forth cDNA encoding a CDK protein is prepared as part of the transfection complex. In certain embodiments, the forth cDNA can encode CDK4 protein or CDK6 protein. In another embodiment, a fifth cDNA of a p16 variant is prepared as part of the transfection complex. In some embodiments, cDNA can be plasmid. In other embodiments, cDNA can be linear. In some embodiments, the cDNA of a p16 variant is obtained from a mammalian patient. In certain embodiments, the transfection complex is transfected into the cell. In some embodiments, the transfection of the transfection complex is transient. The present assay takes advantage of the known interaction between p16 and CDK4/6. When the p16 variant is active, inhibition of CDK4/6 prevents phosphorylation of Rb. The interaction between the two protein products of the first construct and the second construct promote the generation of light emission and therefore allows the indirect measurement of p16 activity.

In another aspect, the present invention provides a method for determining the sensitivity of a CDK4 variant or a CDK6 variant to p16 in a cell. In certain embodiments, the cells have a knockout of endogenous CDK4 and endogenous CDK6. In certain embodiments, the cells have a first construct containing a first cDNA encoding E2F1 protein linked to Dp-1 protein. In a preferred embodiment E2F1 protein is linked to a first portion of a luciferase gene at its C-terminus. In another preferred embodiment, the first construct is stably integrated into the cells. In another embodiment, a second cDNA of a CDK4 variant or a CDK6 variant from a patient is prepared. In another embodiment, a third cDNA encoding Rb protein linked to a second portion of a luciferase gene, preferably at its N-terminus, is prepared. In another embodiment, a fourth cDNA encoding Cyclin D1 protein is prepared. In another embodiment a fifth cDNA of wild-type p16 is prepared. In another embodiment, a transfection complex containing the second construct, the third cDNA, the fourth cDNA and the fifth cDNA is prepared. In a preferred embodiment, the transfection complex is transiently transfected into the cell. The present assay takes advantage of the role of p16 as a natural inhibitor of CDK4/6. When p16 inhibits CDK4/6, Rb interacts with the E2F1 and Dp-1 proteins. In the present assay, the interaction between the two protein products of the first construct and the second construct promote the generation of light emission and therefore allows the indirect measurement of the CDK4 or CDK6 variant sensitivity to wild-type p16. After transfection, the protein products generated from the first and second construct interact to produce a light emission upon addition of a luciferase substrate. The constructs may include other components desirable for adequate expression of the desired protein(s).

In certain embodiments the cDNA encoding for CDK4/6 contains variants that distinguish CDK4/6 from wild-type CDK4/6. In certain embodiments the cDNA encoding for Rb contains variants that distinguish Rb from wild-type Rb. In certain embodiments the cDNA encoding for p16 contains variants that distinguish p16 from wild-type p16.

The exact sequence and size of the first and second portions of the luciferase gene in the first and second constructs may vary provided that when the two portions of the luciferase gene are expressed in an assay cell, the protein products interact to generate a measurable light emission or light signal upon addition of a luciferase substrate. An example of a suitable two-subunit system for detection of protein interaction utilizing luminescent enzymes is Nano-Luc® Binary Technology (NanoBiT).

The present assay can be used in personalized medicine. When genome information is obtained relating to CDK4 or CDK6 gene sequences, one skilled in the art can prepare a cDNA based on the CDK4 or CDK6 gene sequence information. The generated cDNA may be a unique cDNA equivalent to a variant or wild-type sequence of the CDK4 or CDK6 gene of an individual. When genome information is obtained relating to RB sequences, one skilled in the art can prepare a cDNA based on the RB gene sequence information. The generated cDNA may be a unique cDNA equivalent to a variant or wild-type sequence of the RB gene of an individual. When genome information is obtained relating to CDKN2A sequences, one skilled in the art can prepare a cDNA based on the CDKN2A gene sequence information. The generated cDNA may be a unique cDNA equivalent to a variant or wild-type sequence of the CDKN2A gene of an individual. In one aspect, the present invention provides an assay to test patient variants in the CDK4 or CDK6 gene, as identified by next generation sequencing (NGS), thus determining potentially hyperactive and/or inhibitor resistant mutations. In another aspect, the present invention provides an assay to test patient variants in the RB gene, as identified by NGS, thus determining potentially functional or loss of function mutations. In yet another aspect, the present invention provides an assay to test patient variants in the CDKN2A gene, as identified by NGS, thus determining potentially active or loss of function mutations. One advantage of the present assay is to transfect the generated cDNA into an assay cell containing a cDNA encoding E2F1 protein linked to Dp-1 protein and having a knockout of endogenous CDK. A second construct containing another cDNA encoding Rb protein is transfected into the cell. The first cDNA and the second cDNA each link at its C-terminus and N-terminus, respectively, to a separate portion of a luciferase gene. When two portions of the luciferase gene linked to different proteins interact, a signal is created which serves as an indirect measurement of the activity of CDK protein encoded by the mutant or wild-type CDK4 or CDK6.

In certain embodiments, the cDNA may be transiently transfected into the cell. In certain embodiments the cDNA may be stably transfected into the cell. In certain embodiments, cDNAs may be added to the cell by a combination of transient transfection and stable transfection. In one embodiment the cDNA of CDK4/6 or the CDK4/6 variant is transiently transfected. In one embodiment the cDNA of RB or the RB variant is transiently transfected. In another embodiment the cDNA of CDKN2A or the CDKN2A variant is transiently transfected.

In another aspect, the present invention provides a cell line having a double knockout of endogenous CDK4 and endogenous CDK6. In certain embodiments, the cells contain a first construct having a cDNA encoding E2F1 protein linked to Dp-1 protein and a first portion of a luciferase gene, preferably at its C-terminus. In another embodiment, the first construct contains a cDNA encoding E2F1 protein and a first portion of a luciferase gene at its C-terminus.

In certain embodiments, the cell can be a mammalian cell. Preferably, the cell can be a human cell. Examples of cells include, but are not limited to, a breast cell, a kidney cell, a liver cell, a leukocyte cell, a brain cell, an endometrial cell, a colorectal cell, a renal cell, and the like. In certain embodiments the cell is a tumor cell. In certain embodiments, the cell has already been transfected to contain a first cDNA. In certain embodiments, the cell has already been transfected to contain a first cDNA and a second cDNA. In certain embodiments of the invention, the cells have genomic modifications of CDK4, CDK6, or CDK4 and CDK6, which may result in a knock down or a knockout of endogenous CDK4 and/or CDK6 protein. Combinations of genetic modifications are also within the scope of the invention. In certain embodiments, the transfected cells contain a first cDNA construct encoding E2F1 linked to a Dp-1 and a first portion of a luciferase gene (e.g., SEQ. ID. NO: 215) and a second cDNA encoding Rb linked to a second portion of a luciferase gene (e.g., SEQ. ID. NO: 216). In another embodiment, the transfected cDNA is linear or plasmid.

The parent cells of the cell lines of the invention are mammalian cells, such as rat, mouse, hamster, monkey, and human cells. Specific examples of parent cell lines of the invention include HEK293 (human embryo kidney), MCF-7 (human breast cancer), HeLa (human cervix epithelial carcinoma), HT29 (human colon adenocarcinoma grade II), A431 (human squamous carcinoma), IMR 32 (human neuroblastoma), K562 (human chronic myelogenous leukemia), U937 (human histiocytic lymphoma), MDA-MB-231 (Human breast adenocarcinoma), SK-N-BE(2) (human neuroblastoma), SH-SY5Y (human neuroblastoma), HL60 (human promyelocytic leukemia), CHO (Chinese hamster ovary), COS-7 (African green monkey kidney, SV40 transformed), S49 (mouse lymphoma), Ltk (mouse C34/connective tissue), NG108-15 (mouse neuroblastoma and Rat glioma hybrid), B35 (rat neuroblastoma), B50 (rat nervous tissue), B104 (rat nervous tissue), C6 (rat glial tumor), Jurkat (human leukemic T cell lymphoblast), BEM (baby Syrian hamster kidney), Neuro-2a (mouse albino neuroblastoma), NIH/3T3 (mouse embryo fibroblast), A549 (human adenocarcinoma alveolar epithelial), Be2C (human neuroblastoma), SW480 (human colon adenocarcinoma), Caco2 (human epithelial colorectal adenocarcinoma), THP1 (human acute monocyte leukemia), IMR90 (human fetal lung fibroblast), HT1080 (human fibrosarcoma), LnCap (human prostate adenocarcinoma), HepG2 (human liver carcinoma) PC12 (rat adrenal gland phaeochromocytoma), or SK-BR-3 (human breast cancer) cells. In another embodiment, the parent cells are U2OS (human osteosarcoma) cells. In another embodiment, the parent cells are NCI-60 (human tumor) cell lines, such as, A549, EKVX, T47D, or HT29.

In certain embodiments, the CDK4/6 variant contains one mutation. In certain embodiments, the CDK4/6 variant may contain two mutations. In certain embodiments, the CDK4/6 variant may contain three mutations. In certain embodiments the CDK4/6 variant may contain four or more mutations. Similarly, the RB or CDKN2A variant can contain at least one mutation. For example, the RB variant can contain one, two, three, four or more mutations. The CDKN2A variant can contain one, two, three, four or more mutations. Functional variants of CDK4/6, Rb and p16 are those variants that are effective in performing the methods of the invention. These variants can be mutations or polymorphisms. Functional variants can be truncations, such as truncations of 30 amino acid residues or less, or 25 amino acid residues or less, or 20 amino acid residues or less. Examples of functional variants are shown in Table 11 and FIG. 19B.

In certain embodiments, the luminescence or light signal is produced by a structural complementation reporter designed for protein to protein interactions such as NanoLuc® Binary Technology (NanoBiT). In certain embodiments, the luminescence signal is produced by Firefly or Renilla Luciferase. In certain embodiments, the protein to protein interactions are measured by fluorescence signaling systems such as Fluorescence Resonance Energy Transfer (FRET) or by a combination luminescence signal such as Bioluminescence Resonance Energy Transfer (BRET).

In another aspect, the present invention provides a method to determine whether a particular CDK4/6 variant is sensitive to treatment with CDK inhibitors. The method involves preparing a first cDNA encoding a CDK variant of interest followed by transfecting the first cDNA into a cell. The cell is also transfected with first construct containing a second cDNA encoding E2F1 protein linked to Dp-1 protein. A third cDNA encoding Cyclin D1 is also transfected into the cell with the second construct which contains a fourth cDNA encoding Rb protein. The second cDNA is linked at its C-terminus to a first portion of a luciferase gene and the fourth cDNA is linked at its N-terminus to a second portion of a luciferase gene. When the cell is exposed to a CDK inhibitor, CDK4/6 is inactivated, which allows the E2F1 protein linked to the Dp-1 protein to interact with the Rb protein to form the complex which results in a light signal.

In certain embodiments, the transfected cells (i.e., the cells having the cDNA encoding a CDK4/6 variant, a first construct containing cDNA encoding E2F1 linked to Dp-1 protein and a first portion of a luciferase gene, and a second construct containing cDNA encoding Rb linked to a second portion of a luciferase gene) are then exposed to Palbociclib, Ribociclib, or Abemaciclib. A convenient approach to measure the cells response to Palbociclib is to obtain concentration dependent curves. By way of example, Palbociclib can be used from 10 nM to 50 nM to 500 nM. The sensitivity of the CDK4/6 variant toward Palbociclib, Ribociclib, or Abemaciclib can be conveniently measured by an increase in light emission as compared to a negative control (i.e., a vehicle without CDK inhibitor).

In certain embodiments, the cell is transfected with a cDNA encoding CDK4/6. The cDNA can be conveniently prepared using standard methodologies known to one skilled in the art. In certain embodiments, the cDNA can be CDK4/6 wild-type. In certain embodiments the cDNA can be a CDK4/6 variant. In further embodiments, the CDK4/6 variants can contain one or more mutations different from the CDK4/6 wild-type.

In certain embodiments, the present assay can also be used to test if a particular compound has an inhibitory effect toward CDK4/6 protein. The cell system containing the CDK4/6 variant, a construct containing a cDNA encoding E2F1 linked to Dp-1 and a first portion of a luciferase gene, and a construct containing a cDNA encoding Rb linked to a second portion of a luciferase gene, are exposed to a CDK4/6 inhibitor. The sensitivity of the CDK4/6 variant to treatment with the CDK4/6 inhibitor can be measured by an increase in light emission as compared to a negative control.

In certain embodiments, the cells have a knockout or knock down of endogenous CDK4/6. In certain embodiments, the knock down is a genomic modification of at least a portion of the CDK genes that results in a loss of protein expression of CDK4/6, respectively. In certain embodiments, the genomic modification is performed using CRISPR/Cas9 technology. In certain embodiments, the genomic modification is performed using TALENs or recombination technology.

In certain embodiments, the cells have a knock down or knockout of endogenous CDK4/6. In certain embodiments, the knock down or knockout of CDK4/6 is completed in cells that have a genomic modification of at least a portion of the CDKN1A gene. In certain embodiments, the knock down or knockout of CDK4/6 is completed by genomic modification of CDK4/6 using CRISPR/Cas9 technology. In certain embodiments, the genomic modification of CDK4/6 is performed using TALENs or recombination technology. In certain embodiments, the knock down or knockout of CDK4/6 protein may be accomplished through siRNA treatment.

In certain embodiments, the present assay may be used to determine whether variants in a patient CDK4/6 gene would create a variant CDK4/6 that will respond to a specific CDK4/6 inhibitor. The method involves preparing a cDNA equivalent to a CDK4/6 variant from a patient followed by transfecting the cDNA into a cell. The cell has undergone a genomic modification to the CDK4/6 gene, resulting in CDK4/6 knock down or preferably knockout. The cell has been transfected with a first construct containing a cDNA encoding E2F1 protein linked to Dp-1 protein as well as a second construct containing a cDNA encoding Rb protein. The first cDNA is linked at its C-terminus to a first portion of a luciferase gene and the second cDNA is linked at its N-terminus to a second portion of a luciferase gene. When CDK4/6 is inactivated, the protein products of the two cDNAs interact to form a complex and produce a light signal.

In certain embodiments, the present assay may be used to screen new CDK4/6 inhibitor compounds to determine efficacy in the treatment of cancer. CDK4/6 inhibitors that are currently part of cancer treatment studies include Palbociclib, Ribociclib, and Abemaciclib. Depending on the compound to be utilized in the assay, suitable vehicles include DMSO, DMF, water, aliphatic alcohols, and mixtures thereof. In certain embodiments, the present assay may be used to identify new chemical compounds to assess their abilities to inhibit CDK4/6.

The assays of the invention are carried out under culture conditions effective for protein expression from cells. The assays are performed in a vessel capable of holding the cells and reagents and not interfering with assay results. In some embodiments the plates are surface treated to facilitate adherence of the assay cells to the wells of the plate, such treatment is commonly referred to as "tissue culture treated". The surface treatment is typically an oxygen plasma discharge that renders the surface of the wells more hydrophilic. In some embodiments the assays are miniaturized and use multi-well plates known in the art. In certain embodiments, the present assay can be conveniently performed in a 96 well plate, but can also be adopted for high-throughput 384 well plates or 1536 well plates. In some embodiments dispensing the cells and/or reagents for the assays into the wells of the plates is automated. In some embodiments the cells and/or reagents are dispensed continuously at a high speed. In one embodiment an acoustic liquid dispenser is used to dispense the reagents.

The following examples are provided to further illustrate various preferred embodiments and techniques of the invention. It should be understood, however, that these examples do not limit the scope of the invention described in the claims. Many variations and modifications are intended to be encompassed within the spirit and scope of the invention.

EXAMPLES

Example 1 Next-Generation Sequencing to Interrogate Mutation of Tumor

Since genetic alterations are very common cause in different types of cancer, knowing the gene mutations and drug resistance would be beneficial in cancer therapy. To survey the mutation status of CDK4 and CDK6 genes, whole exome sequencing was performed. Genomic DNA was extracted and used to prepare library for next-generation sequencing. The identified mutations, which caused change in amino acid sequence, were picked to examine its functional effect on the genes in our proprietary cell-based assay described below. The patient gene carrying the identified mutation is constructed using polymerase chain reaction (PCR) mediated overlapping extension in a format of linear expression cassette.

Example 2 Construction of Linear Expression Cassette of Human CDK4/6

In order to study the effect of unknown mutations in human CDK4 and CKD6 genes, we decided to generate linear expression cassette, containing CMV promoter that controls CDK4/6 expression, coding sequence of CDK4/6 followed by terminator and polyadenylation signal. To do so, overlapping extension PCR was employed to construct the linear expression cassette using expression plasmids of human CDK4/6 as PCR template. Employing this method, the construction of linear expression cassette takes around 4-8 hours. However, the traditional cloning method to generate expression plasmid takes around 2-4 days. Therefore, making patient gene in linear expression cassette format is crucial for a clinical diagnostic test because of its quick turn-around time.

Example 3 Construction of Expression Plasmids of Human CDK4, CDK6 and CCND1 cDNA plasmids encoding human CDK4, CDK6, and CCND1 genes were purchased (Dharmacon). The coding sequences of the previously mentioned genes were amplified by PCR. NheI and NotI/XhoI restriction enzyme sites were inserted into forward and reverse primers respectively for purpose of cloning (Table 1). PCR products containing the coding sequences of human CDK4, CDK6 and CCND1 were sub-cloned into the pcDNA3.1 (+) using NheI and (NotI)/XhoI restriction enzymes. The nucleotide sequences of all genes were verified by DNA sequencing. These human CDK4 and CDK6 expression plasmids were used as PCR templates to construct linear expression cassettes of wild-type ("WT") or mutated forms of CDK4 and CDK6.

TABLE 1

Primers used for expression plasmids

| | | |
|---|---|---|
| CDK4 NheI F | TG GCT AGC C GCC ACC ATG GCT ACC TCT CGA TAT GAG [SEQ. ID. NO: 8] | |
| CDK4 NotI R | CGA GC GGCCGC TCA CTC CGG ATT ACC TTC ATC [SEQ. ID. NO: 9] | |
| CDK6 NheI F | TG GCT AGC C GCC ACC ATG GAG AAG GAC GGC CTG TGC [SEQ. ID. NO: 10] | |
| CDK6 XhoI R | GA CTC GAG TCA GGC TGT ATT CAG CTC CGA [SEQ. ID. NO: 11] | |
| CCND1 NheI F | ATTAGCTAGCGCCGCCACCATGGAACACCAGCTCCT [SEQ. ID. NO: 12] | |
| CCND1 XhoI R | ATACTCGAGTCAGATGTCCACGTCCCGCAC [SEQ. ID. NO: 13] | |

Generation of Linear Expression Cassette of WT and Mutated CDK4 and CDK6

A linear expression cassette of human WT CDK4 and CDK6 was generated by UF-CMV forward and BGH-UR reverse primers. The amplified products were gel-purified. The DNA concentration was quantitated by the optical density at 260 nm using Nanodrop.

A linear expression cassette of mutated CDK4 or CDK6 was generated by PCR mediated overlapping extension method. A pair of forward and reverse primers containing the targeted mutations was designed. The mutated codon was located in the middle of a primer flanked by 18-21 nucleotides on each side. Two PCRs (named as PCR #1 and PCR #2 in FIG. 1) were performed using UF-CMV forward and mutated reverse primers, or mutated forward and BGH-UR primers. The PCR products were cleaned up by ExoSAP-IT® (Affymetrix) to remove unconsumed dNTPs and primers. The treated PCR products were mixed together followed by dilution with water. A second round of PCR was performed using the diluted PCR mixture, and the UF and UR primers (FIG. 1). The amplified products were gel-purified. The DNA concentration was quantitated by the optical density at 260 nm using Nanodrop. The targeted mutations were incorporated in the CDK4 or CDK6 genes during the PCR mediated overlapping extension method. The introduced mutations were confirmed by the DNA sequencing.

Example 4 Transfection Method

HEK293 cells are specific cell line originally derived from human embryonic kidney cells grown in tissue culture. HEK293 cells have been widely used in cell biology research for many years because of their reliable growth and propensity for transfection. In general, there are two major types of transfection, forward and reverse.

A reverse transfection protocol was performed whereby freshly passaged cells were added to transfection complexes to reduce hands-on time for the end user. During this process, cells were not adhered to the plate surface by the time they interacted with the transfection complexes.

Example 5 Interacting Partners for Our NanoBit Assay

An assay that could measure the interaction between Rb, E2F1 and Dp-1 was developed, since Dp-1 forms a heterodimer with E2F1 and this interaction is important for Rb/E2F1 binding. When two proteins (Rb and E2F1) are in close proximity or in complex, a light signal was generated. For the purposes of the current assay, split-luciferase complementation was used to measure the interaction between Rb and E2F1, which was used as a surrogate measure of CDK4/6 activity and the ability of CDK4/6 to respond to a CDK4 or CDK6 inhibitor (for example, Palbociclib, Ribociclib, or Abemaciclib). The NanoBiT assay system by Promega (Madison, Wis.; Dixon et al., 2015, ACS ChemBiol) was used in the split luciferase complementation design.

Figure 2:
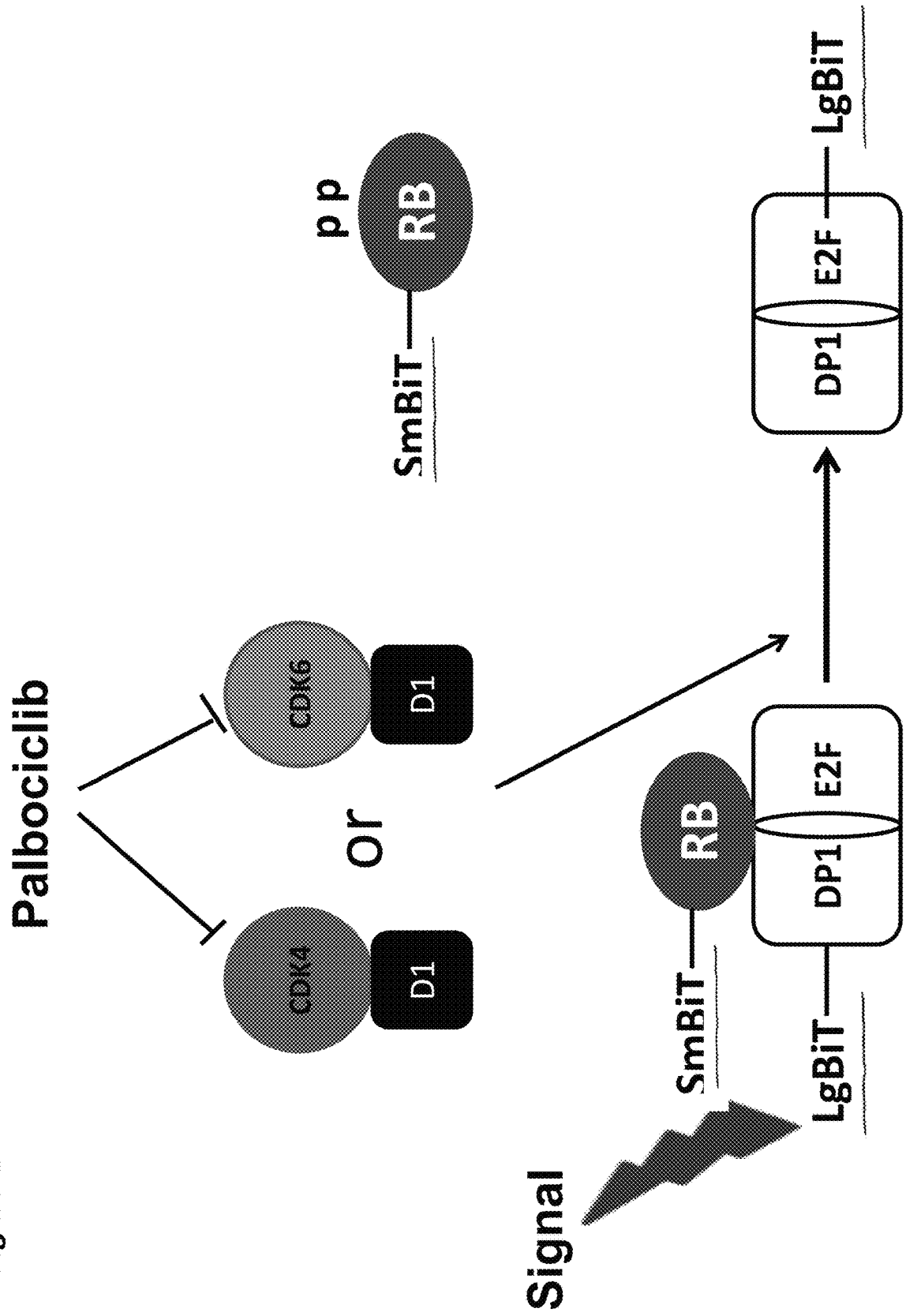
FIG. 2 shows a schematic representation of CDK4/CDK6 pathway and NanoBit design.

FIG. 2 depicts a design of a signal system to measure CDK4/6 activity. Under basal conditions inside the cell, Rb was active and interacted with an E2F1/Dp-1 heterodimer. However, in the presence of the CDK4 or CDK6, Rb is phosphorylated and released from the interacting complex. In the presence of a CDK4 or CDK6 inhibitor (for example, Palbociclib, Ribociclib, or Abemaciclib), CDK4/6 was no longer available, thus promoting Rb/E2F1-Dp-1 complex formation (FIG. 2). For this assay design, cDNAs of Rb linked to different parts of the luciferase protein were created, either termed as the "Small BiT" (SB), or "Large BiT" (LB) and E2F1-Dp-1 was linked to the different portion of the luciferase protein. When Rb and E2F1/Dp-1 bind, the NanoBiT parts of the luciferase complement each other, and they emitted a light signal when the luciferase (NanoGlo) substrate was added.

PCR was performed and the ligated cDNAs fragments of RB, E2F1, and DP1 were generated, according to methods known in the art, into NanoBiT designed vectors MCS-1, MCS-2, MCS-3, and MCS-4, respectively (available from Promega). Oligonucleotide primers designed for subcloning are indicated in Table 2 and Rb, E2F1, and Dp-1 DNA and amino acids' fragments used in NanoBit assay are shown in FIG. 3.

Example 6 Finding the Best Combination of Partners for NanoBit Assay

Figure 4A:
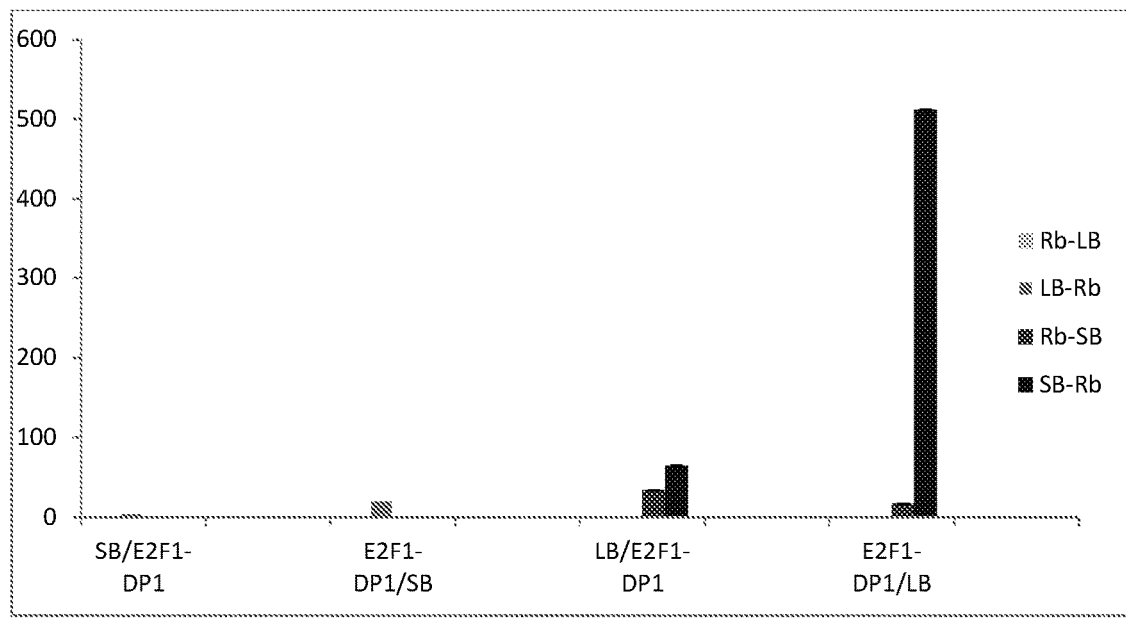
FIG. 4A shows combinations of Rb linked to NanoBit constructs and observed activity.
Figure 4B:
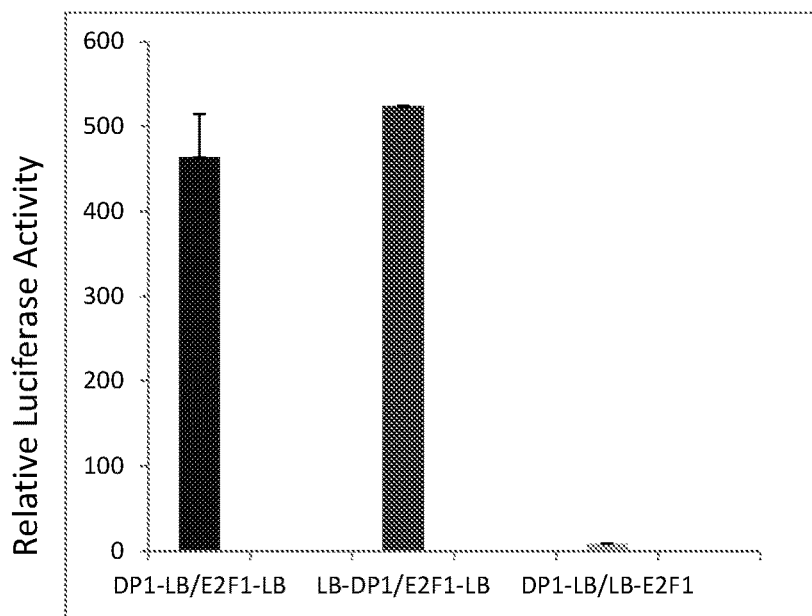
FIG. 4B shows different combinations of E2F1 and Dp-1 linked to NanoBit and interaction activity with SB-Rb.

Using the above-described assay, HEK293 cells were transiently transfected with different combinations of SB-Rb or LB-Rb and E2F1-Dp-1/LB or E2F1-Dp-1/SB components containing C-terminal and N-terminal constructs (FIG. 4A). The generated constructs were tested for the high luciferase signal and the SB-Rb with E2F1 and Dp-1-LB at C-terminus or N-terminus (FIG. 4B) were selected for further use. Relative intensities are represented as relative luminescence units (RLU) (FIG. 3). Data represents a sample experiment where each condition was performed in triplicate and represent mean+SD. According to the data the higher luciferase activity is observed for SB-Rb and E2F1-LB, Dp-1 constructs.

Figure 4C:
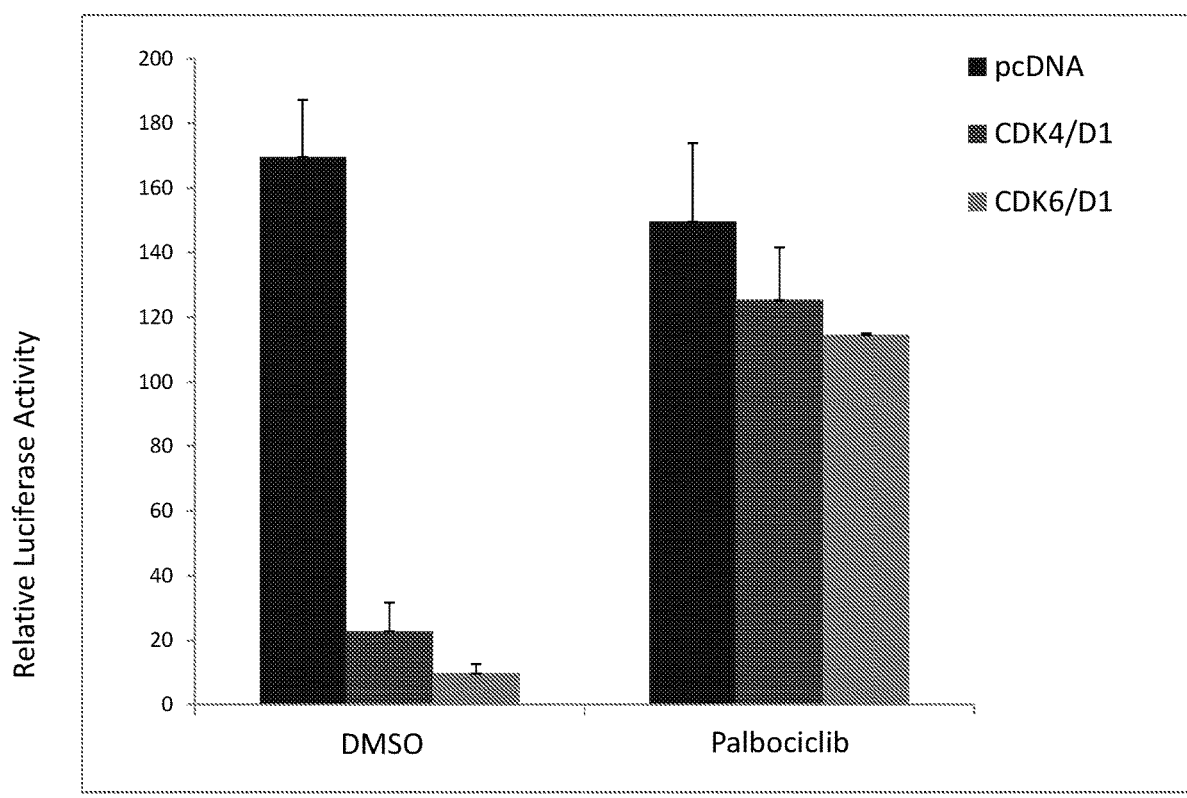
FIG. 4C shows initial relative luciferase activity of CDK4 and CDK6 with and without specific CDK4/6 Inhibitor-Palbociclib.

Example 7 Overexpression of CDK4/6 Treated with Palbociclib in NanoBit Approach The selected SB-Rb, E2F1-LB, and Dp-1-LB complex was tested for specific CDK4 or CDK6 activity using the inhibitor Palbociclib (FIG. 4C). When CDK4 or CDK6 was added, decreased activity was observed as Rb is phosphorylated and there is no Rb/E2F1-Dp-1 interaction. With treatment of an inhibitor (for example, Palbociclib, Ribociclib, or Abemaciclib), an increased luminescence was observed, which was consistent with a decrease in CDK activity resulting in an increased interaction between SB-Rb and E2F1-Dp1-LB.

The "fold change" based on the fraction of luminescence activity observed in cells treated with Palbociclib was compared to that of the vehicle treated. To examine the ability of the split luciferase to properly assay CDK4/6 activity, HEK293 cells were transfected with CDK4 (CDK6) and CyclinD1 and then tested for the dependence of CDK activity with a 2 hour ("h" or "hr") treatment with Palbociclib (500 nM). An increase in signal with Palbociclib was interpreted to coincide with the ability to evaluate CDK4/6 activity by the designed assay.

Structural biology data of co-crystallizing RbC, E2F1, and Dp-1 suggested relatively close proximity of the N-terminus of RbC with C-terminus of E2F1 and Dp-1 (Rubin et. al, Cell, 2005).

Optimized cDNAs for the assay with the SB to be N-terminally linked to RB (A) and the LB to be C-terminally linked to E2F1 (B), or the LB to be N-terminally linked to Dp-1 (C) are indicated in FIG. 3. The underlined portion is the SB or LB of the sequence. The remainder of the cDNA sequence is the cDNA provided by Origene for the expression of the designed protein. All sequences were confirmed by Sanger Sequencing. Based on the cDNA sequences, the SB-RB (D), E2F1-LB (E), and LB-DP1 (F) were created with the indicated nucleic acid sequences, when the cDNAs were expressed in mammalian cells.

TABLE 2

Primers designed for subcloning RB, E2F1 and DP1 cDNA constructs into NanoBiT vectors.

| Target/Purpose | Forward Primer | Reverse Primer |
| --- | --- | --- |
| E2F1-LB, E2F1-SB into MCS-1, MCS-2 using Hind III and EcoRI | CT AAGCTT GCC ACC ATG CTC GAC TAC CAC TTC GGC CT [SEQ. ID. NO: 14] | C AGA ATT CCC CTC CTC AGG GCA CAG GAA AAC [SEQ. ID. NO: 15] |
| RB-LB, RB-SB into MCS-1 MCS-2 using Hind III and EcoRI | CT AAGCTT GCC ACC ATG TAT GCT TCC ACC AGG CCC CCT [SEQ. ID. NO: 16] | C AGA ATT CCC TTT CTC TTC CTT GTT TGA GGT ATC CAT [SEQ. ID. NO: 17] |
| DP1-LB, DP1-SB into MCS-1, MCS-2 using Hind III and EcoRI | CT AAGCTT GCC ACC ATG GCT CAG GAA TGT CAG AAC TTA GAG [SEQ. ID. NO: 18] | C AGA ATT CCC TGC CGT CGT GAT GAA CAC GCC [SEQ. ID. NO: 19] |
| LB-E2F1, SB-E2F1 into MCS-3, MCS-4 using EcoRI and XbaI | AGG AAT TCA CTC GAC TAC CAC TTC GGC CT [SEQ. ID. NO: 20] | AC TCT AGA TTA CTC CTC AGG GCA CAG GAA AAC [SEQ. ID. NO: 21] |
| LB-RB, SB-RB into MCS-3, MCS-4 using EcoRI and XbaI | AGG AAT TCA TAT GCT TCC ACC AGG CCC CCT [SEQ. ID. NO: 22] | AC TCT AGA TTA TTT CTC TTC CTT GTT TGA GGT ATC CAT [SEQ. ID. NO: 23] |
| LB-DP1, SB-DP1 into MCS-3, MCS-4 using EcoRI and XbaI | AGG AAT TCA GCT CAG GAA TGT CAG AAC TTA GAG [SEQ. ID. NO: 24] | AC TCT AGA TTA TGC CGT CGT GAT GAA CAC GCC [SEQ. ID. NO: 25] |

Example 8 CRISPR Method to Eliminate Endogenous CDK4 and CDK6

Figure 5A:
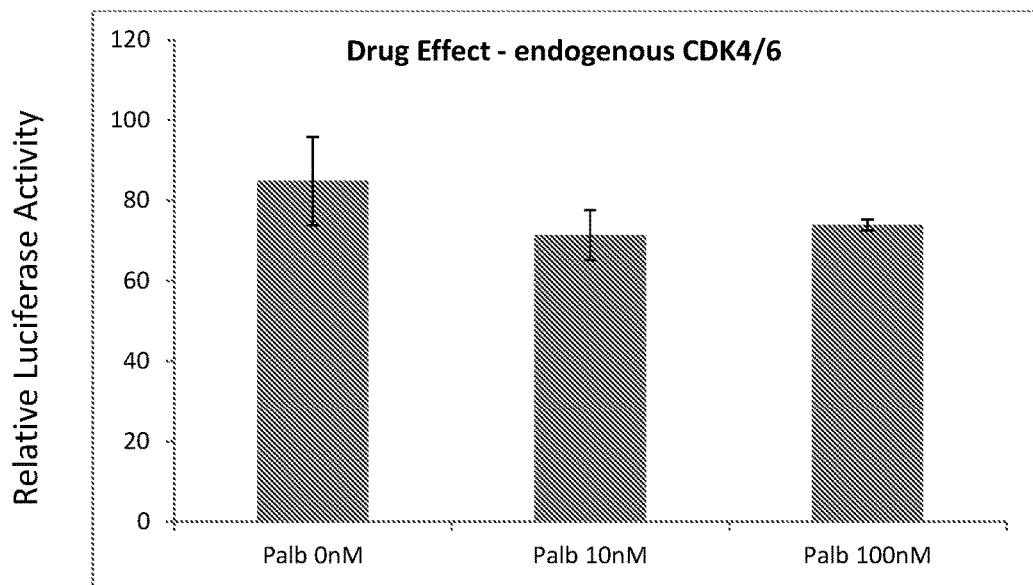
FIG. 5A shows no endogenous contribution of CDK4 and CDK6 exposed to the CDK4/6 inhibitor Palbociclib.
Figure 5B:
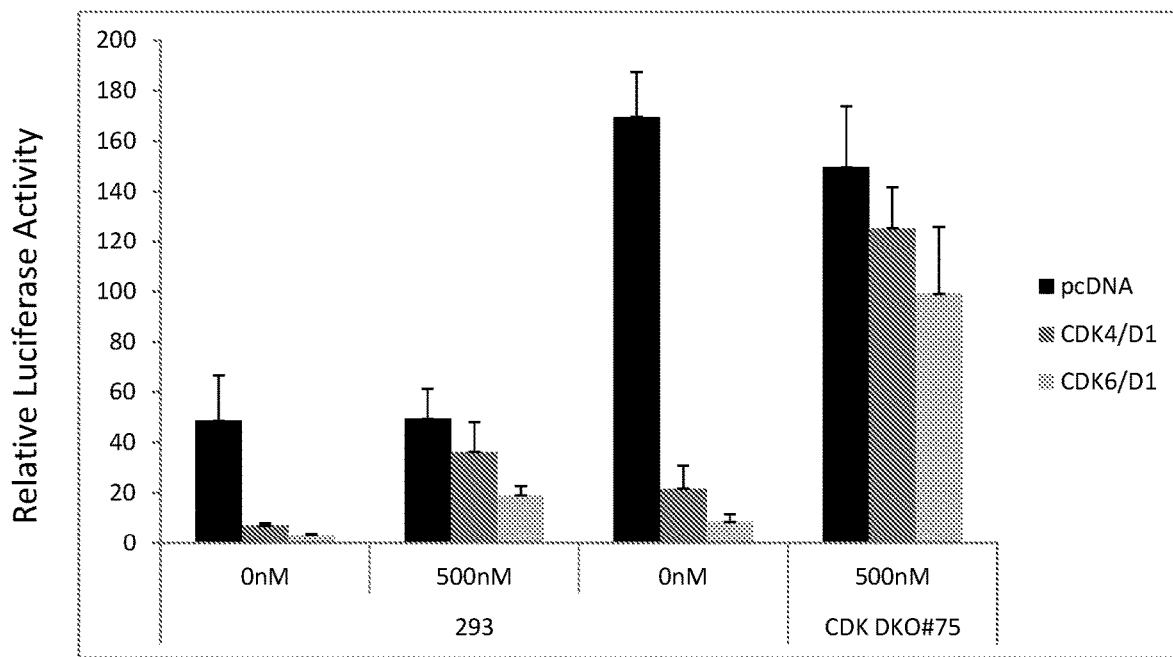
FIG. 5B shows relative luciferase activity of CDK4 and CDK6 for the stable CDK DKO cell line (CDK DKO #75) treated with CDK4/6 Inhibitor-Palbociclib.

CRISPR technology was used to genomically modify the CDK4 and CDK6 genes and remove their expression even though there is no endogenous contribution of CDK4 and CDK6 in our assay. Primers that were used for screening CDK DKO clones are presented in Table 3. Data is shown in FIG. 5.

TABLE 3

CRISPR screening primers

| Target | Forward Primer | Reverse Primer |
|---|---|---|
| CDK4 | 5'-ATGCAAGGCATGTGTCATGT [SEQ. ID. NO: 26] | GCAAGAGTTCAAGACCA GCC [SEQ. ID. NO: 28] |
|  | 5'-TTGTTGCTGCAGGCTCATAC [SEQ. ID. NO: 27] |  |
| CDK6 | 5'-TATGGGAAGGTGTTCAAGGC [SEQ. ID. NO: 29] | CTGTGCCTGGATTACCC ACT [SEQ. ID. NO: 31] |
|  | 5'-TGCACAGTGTCACGAACAGA [[SEQ. ID. NO: 30] |  |

Example 9 NanoBit Assay and Different Time Treatment with CDK4/6 Inhibitor

Figure 6:
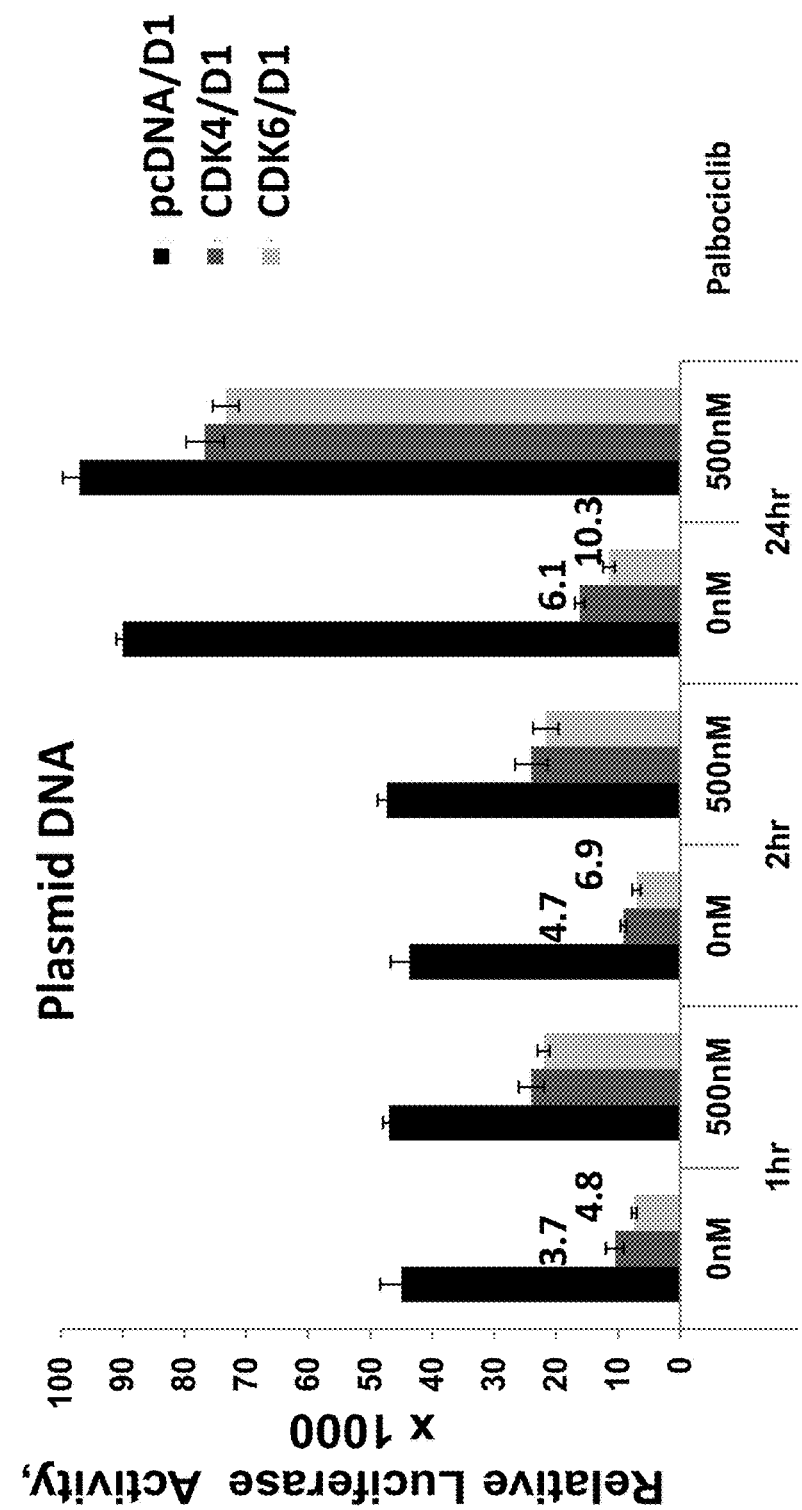
FIG. 6 shows relative luciferase activity of CDK4 and CDK6 when treated with Palbociclib for 1, 2 and 24 hours.

The assay was further optimized by examining the time of treatment required to see the effect indicated by treating SB-Rb/LB-Dp-1/E2F1-LB transfected HEK293/CDK DKO cells with Palbociclib from 1-24 hours (FIG. 6). The increase in fold-change, indicated by the numbers above the bars, was the highest at 24 hr of treatment, and less for 1 or 2 hr of treatment. Therefore, the SB-Rb/LB-Dp-1/E2F1-LB assay performs best within 24 hr of treatment.

Example 10 Selection of Stable Cell Clones Carrying E2F1-Dp-1-LB

Figure 7A:
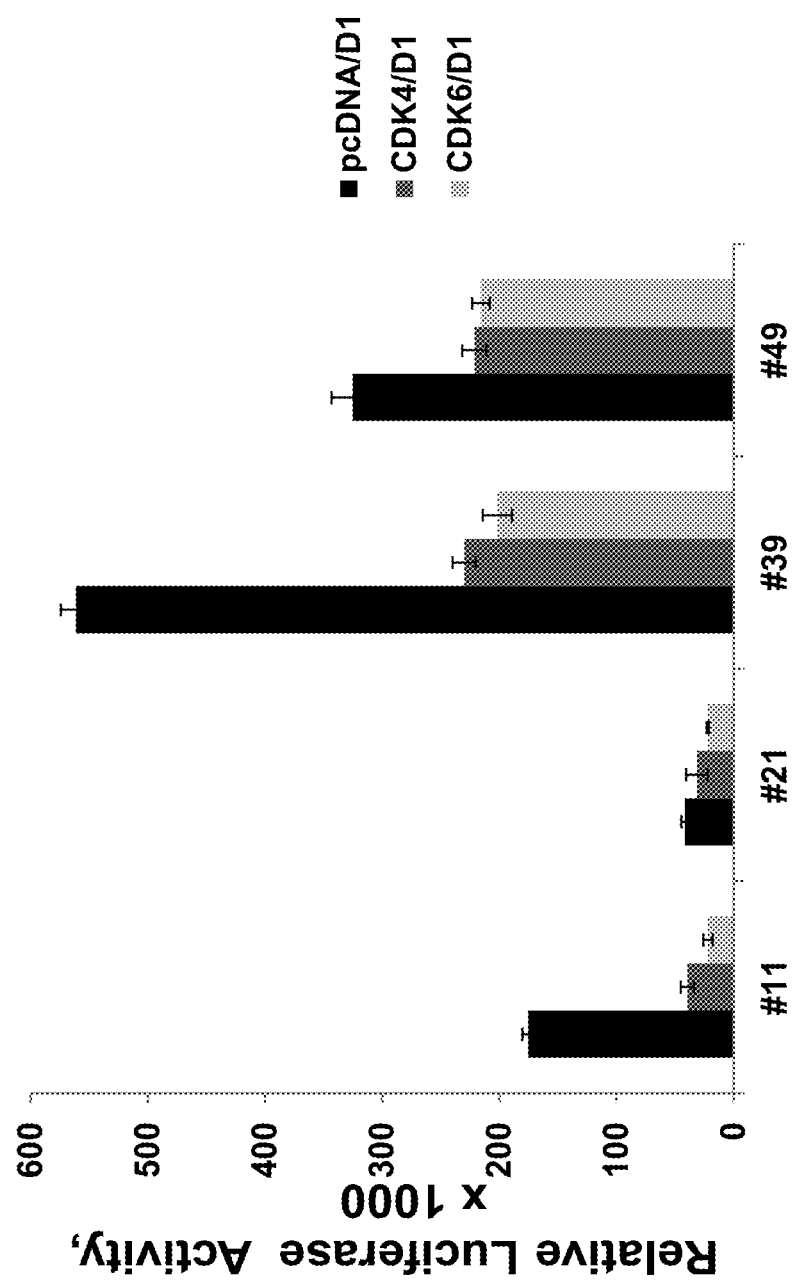
FIG. 7A shows relative luciferase activity of CDK4 and CDK6 for stable single cell clones (E2F1-DP1-NanoBit construct integrated into genome) in clone numbers 11, 21, 39, and 49.
Figure 7B:
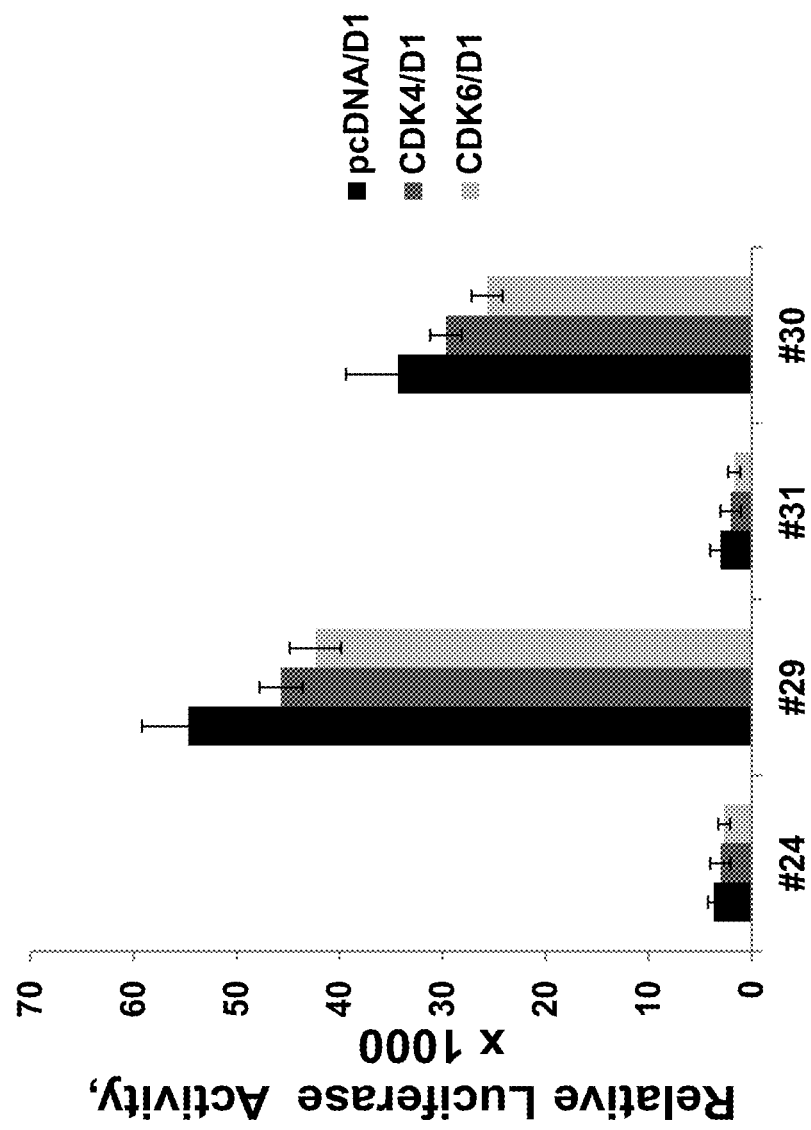
FIG. 7B shows relative luciferase activity of CDK4 and CDK6 for stable single cell clones in clone numbers 24, 29, 31, and 30.
Figure 8:
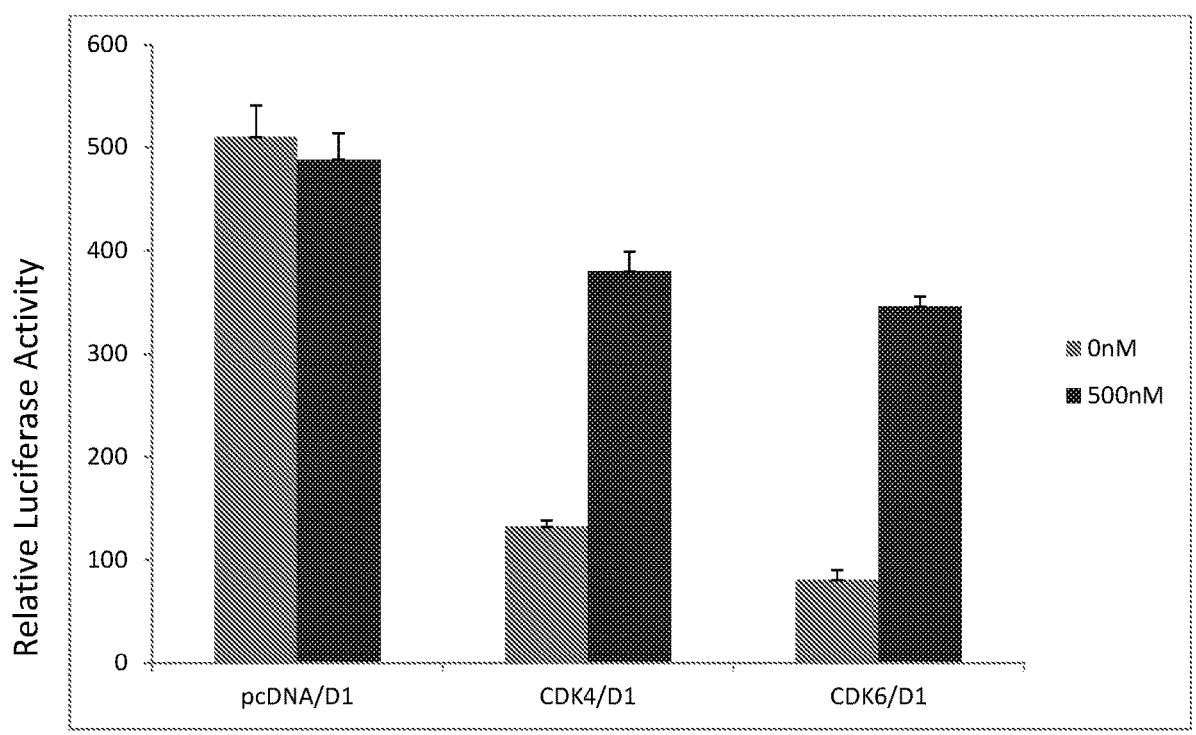
FIG. 8 shows relative luciferase activity of CDK4 and CDK6 untreated and treated with Palbociclib for stable clone cell line #11

Within the provided assay design, stable cell lines were produced using the HEK293 CDK DKO cell parent line expressing E2F1-Dp-1/LB linked together (there is GGSG between them). After selection and screening for positive clones using a SB-Rb-mediated increase in signal, WT CDK4 or WT CDK6 was transfected into independent stable single-cell clones. All of the single-cell clones generated containing the E2F1-Dp-1/LB responded to Palbociclib, Ribociclib, or Abemaciclib with an increase in signal, as previously observed with over-expression of WT CDK4 or WT CDK6 (FIG. 7). Cell line #11 had the best response and was chosen for all future use in assay development (FIG. 8).

Example 11 Using Stable Cell Line #11 and Assay Optimization

Figure 9A:
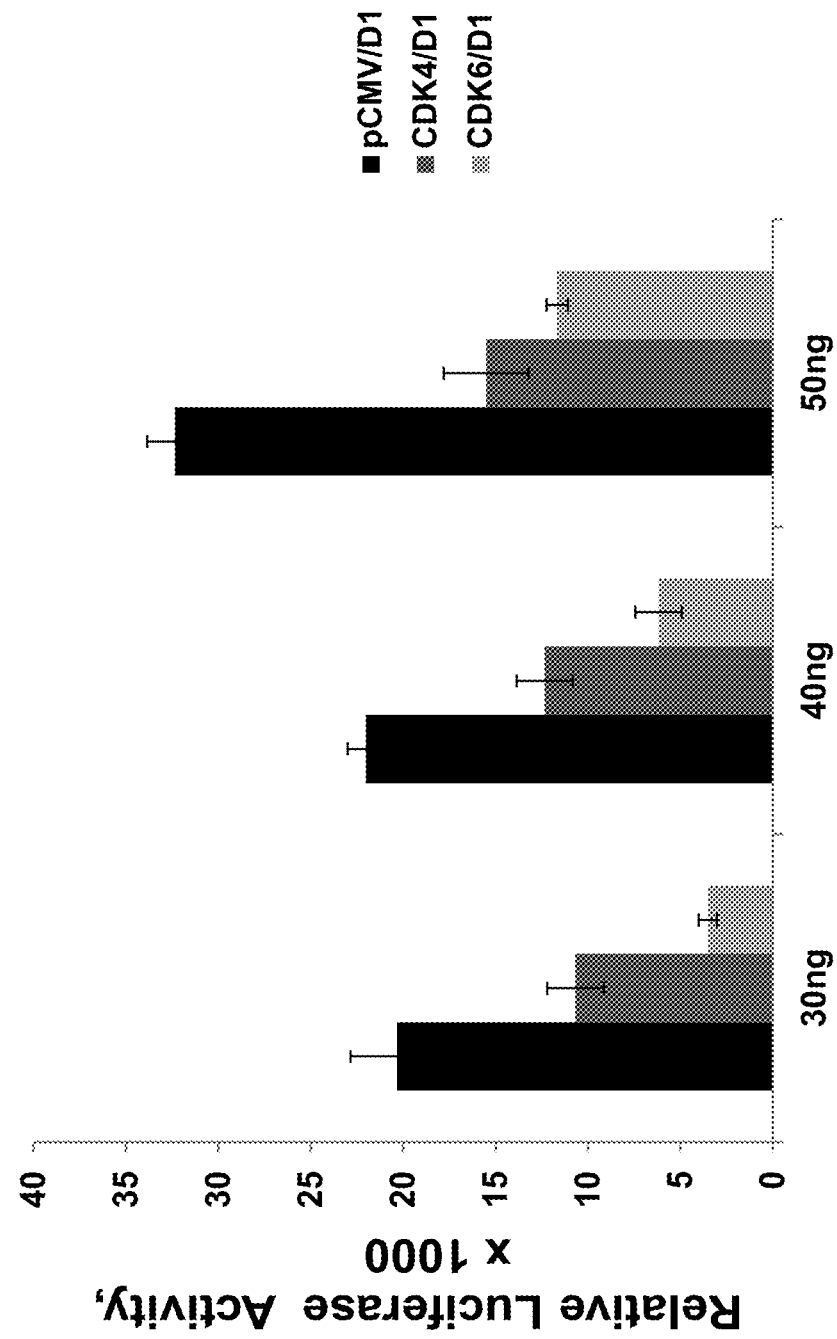
FIG. 9A and FIG. 9B show optimization of the CDK4 and CDK6 assay by varying the amounts of Rb and CDK4/D1, respectively.
Figure 9B:
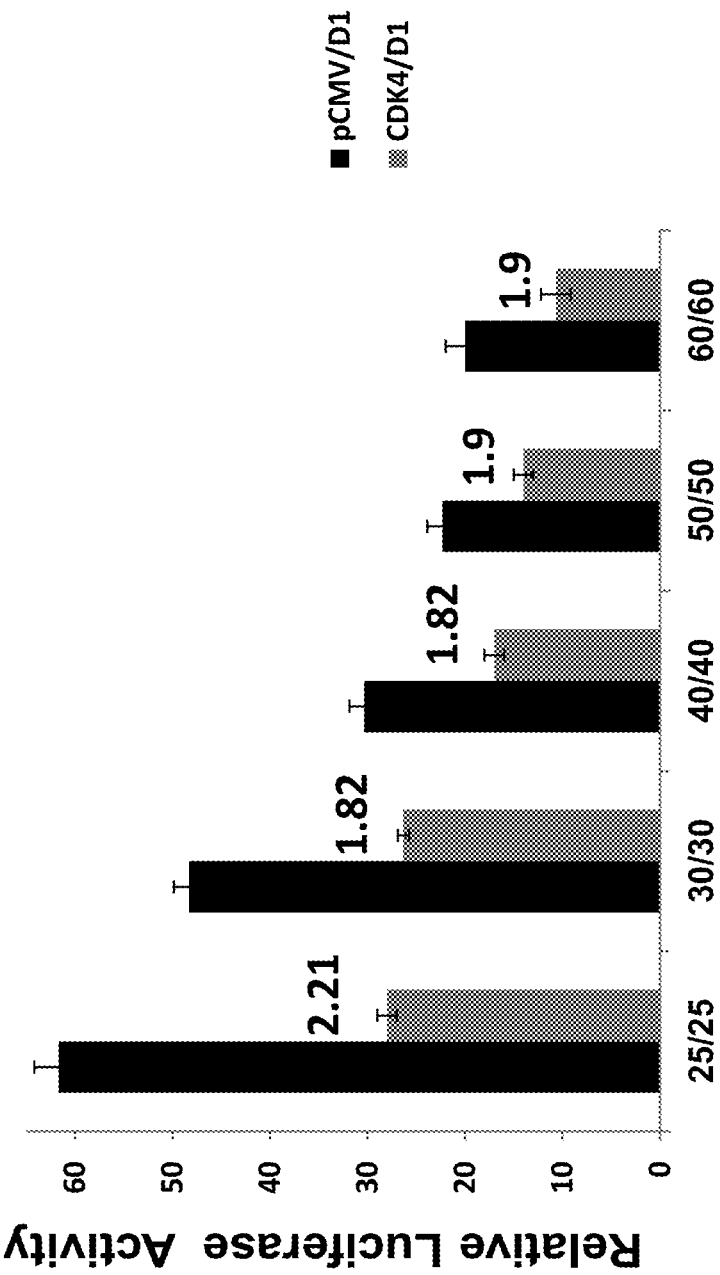
Figure 9C:
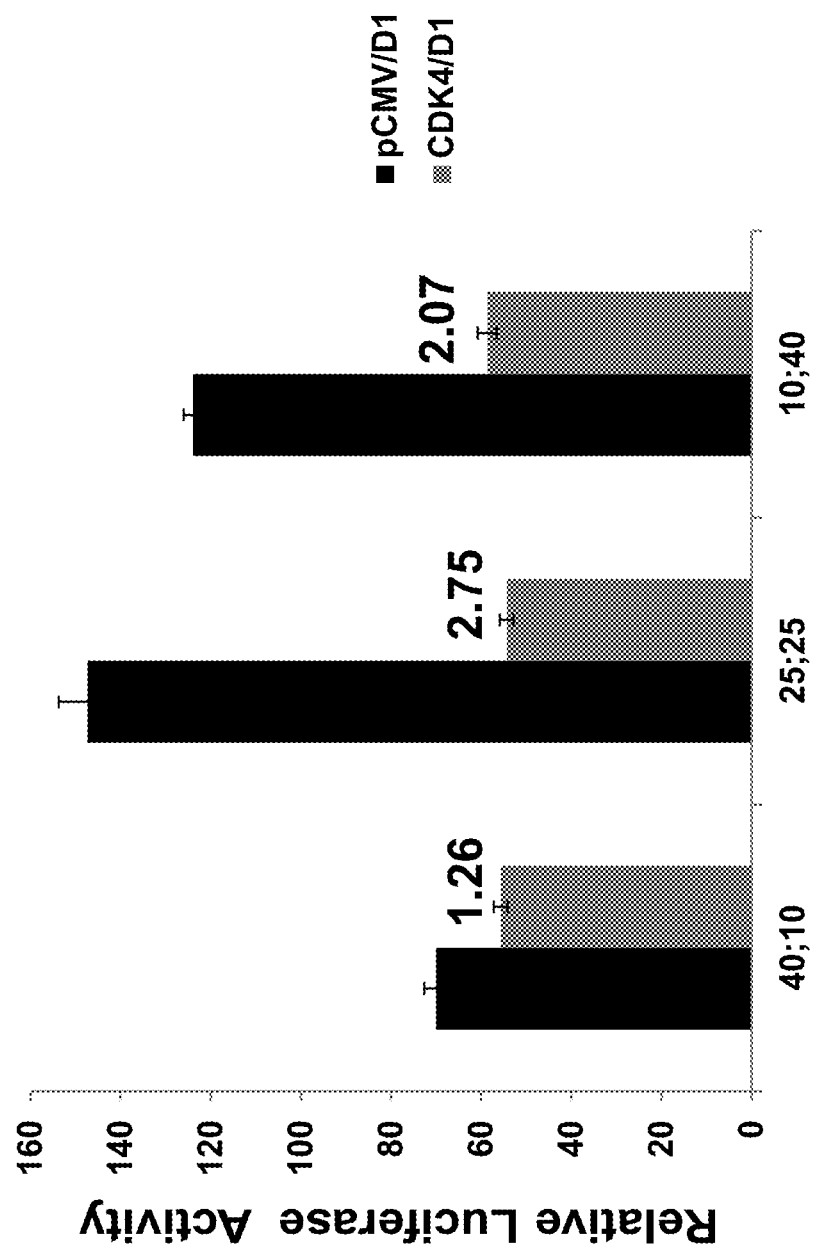
FIG. 9C shows optimization by varying the ratio of CDK4/D1.
Figure 9D:
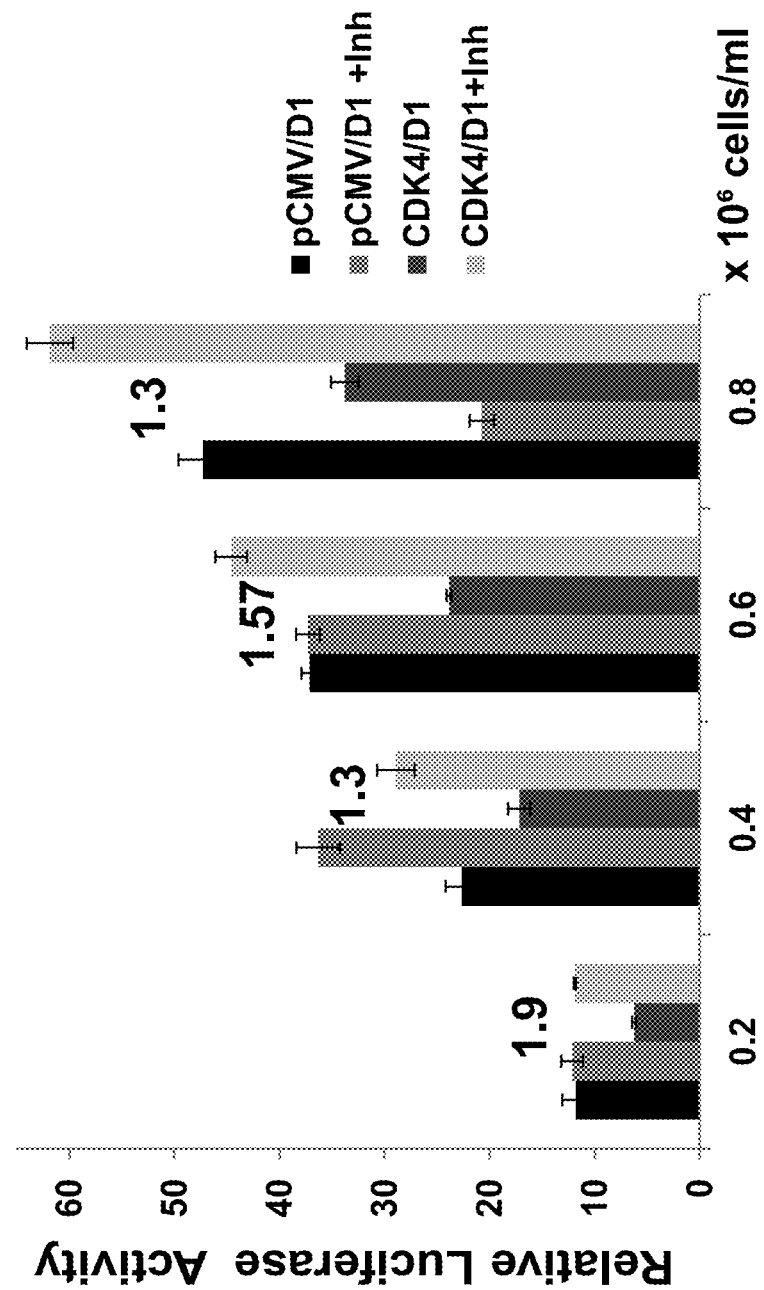
FIG. 9D shows optimization by varying the amount of cells in the assay for CDK4 treated with Palbociclib.

Using stable cell line #11 the assay was optimized for 384 well format plate by examining different Rb amounts (FIG. 9A), CDK4/D1 amounts (FIG. 9B), CDK4/D1 ratios (FIG. 9C), and cell amounts (FIG. 9D). The increase in fold-change, indicated by the numbers above the bars, was the highest at the following conditions: using 30 ng of Rb, 25 ng of CDK4 and CyclinD1 for CDK4 assay, and 35 ng of CDK6 and CyclinD1 for CDK6 assay, and $0.2 \times 10^6$ cells/ml and $0.3 \times 10^6$ cells/ml respectively.

Example 12 Dose Response Curves for WT CDK4 and CDK6

Figure 10A:
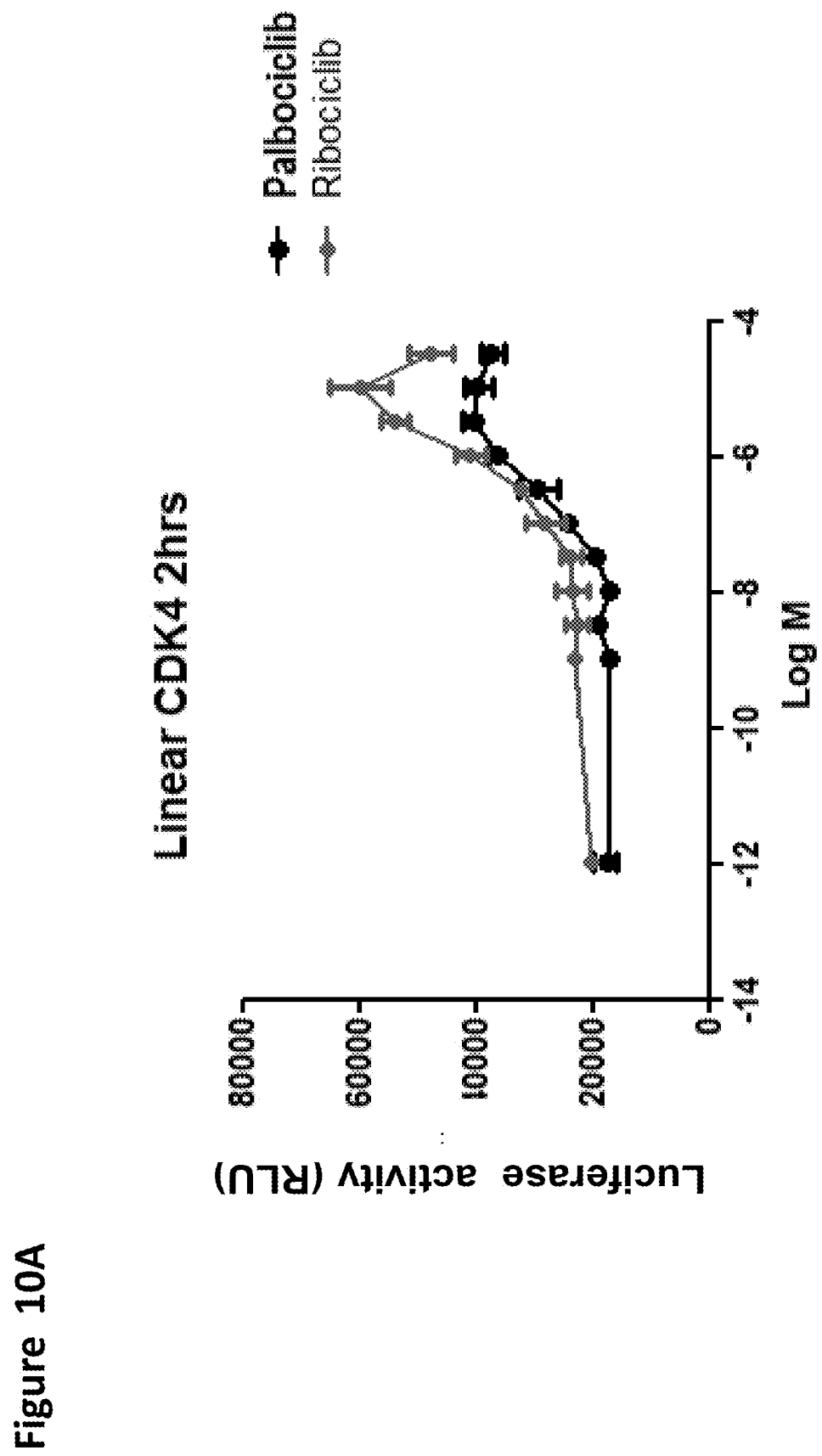
FIG. 10A and FIG. 10B show the dose response curves for CDK4 and CDK6, respectively, with exposure to Palbociclib and Ribociclib over 2 hours.
Figure 10B:
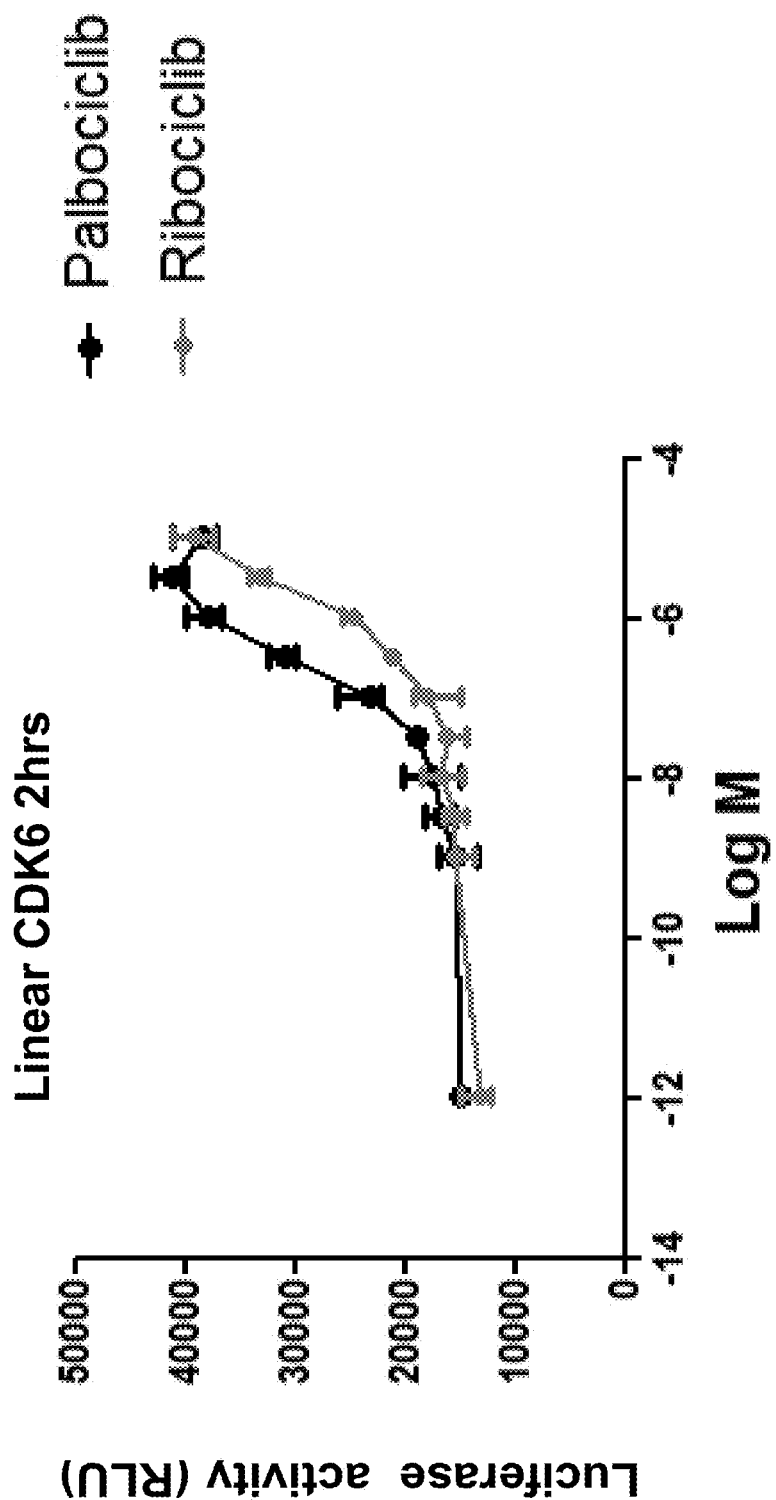
Figure 11A:
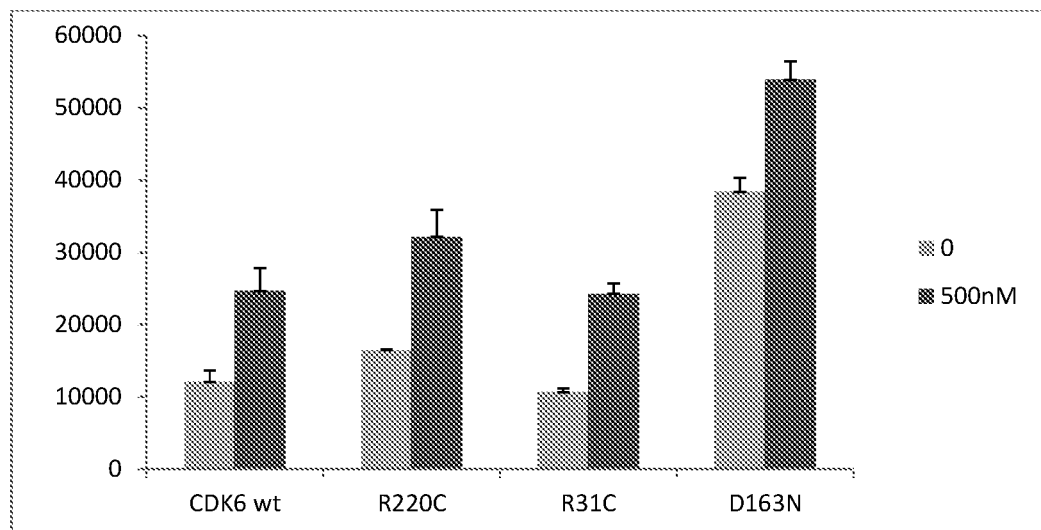
FIG. 11A and FIG. 11B show relative luciferase activity of different CDK6 mutants exposed to Palbociclib.
Figure 11B:
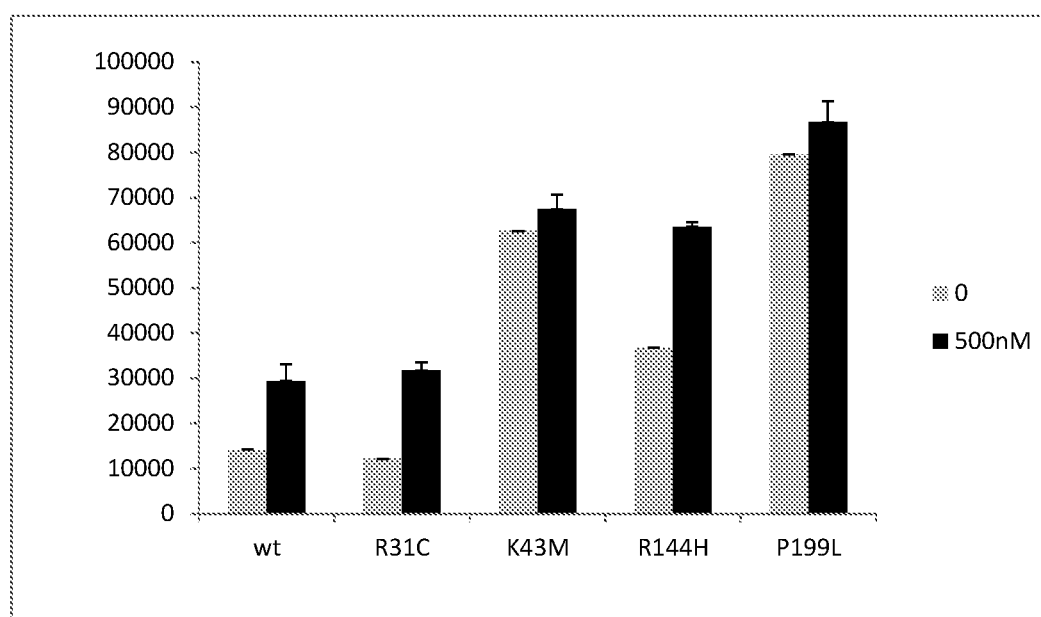
Figure 11C:
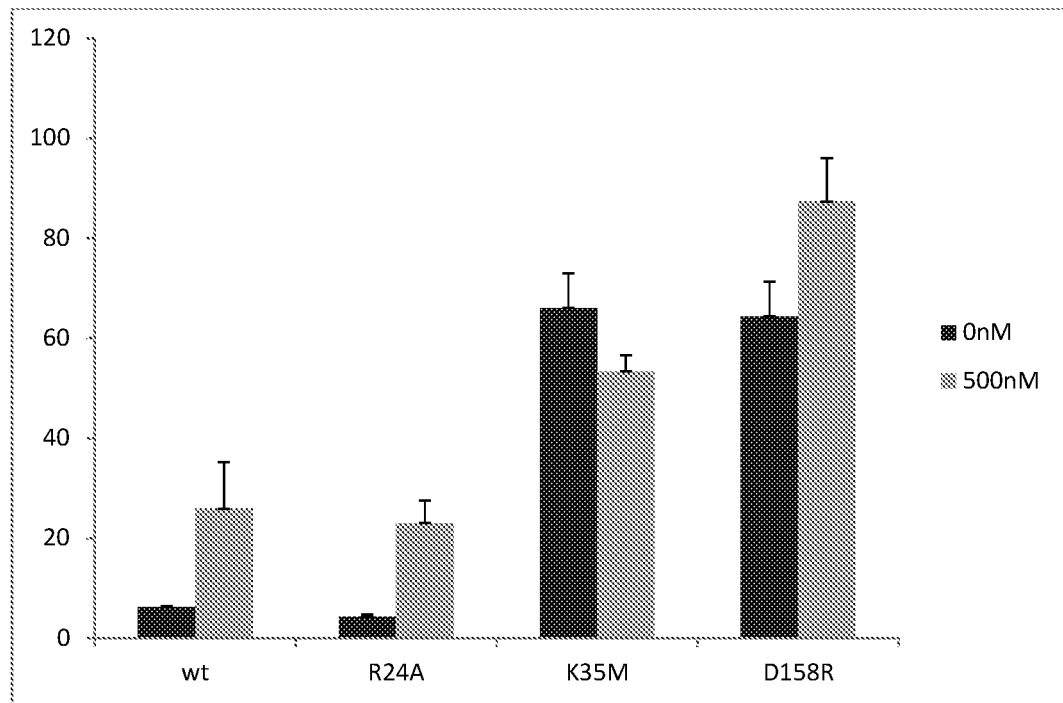
FIG. 11C and FIG. 11D show relative luciferase activity of different CDK4 mutants exposed to Palbociclib.
Figure 11D:
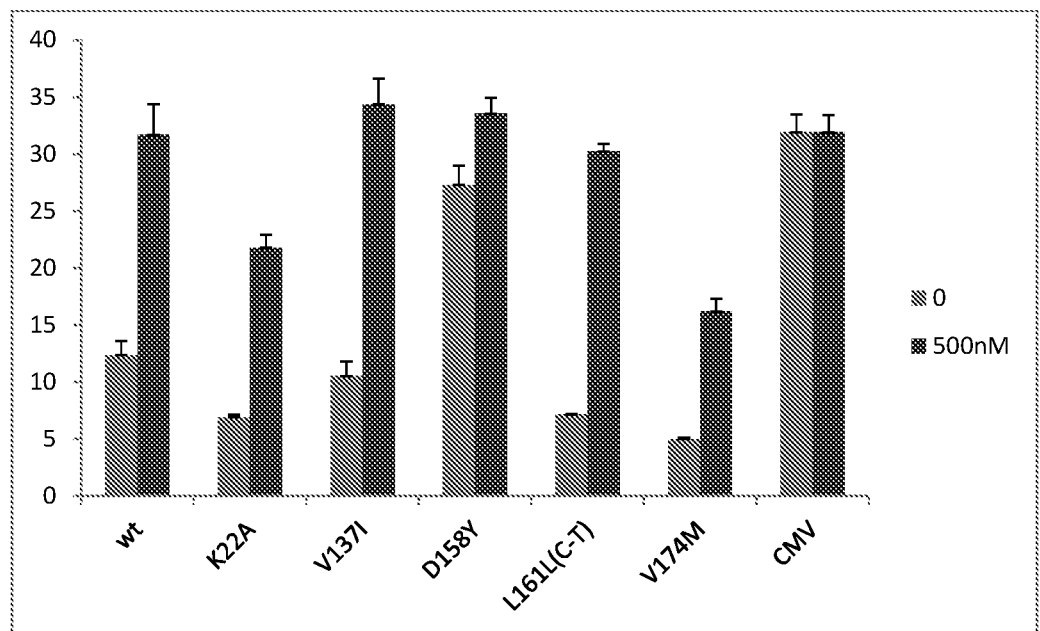

Based on the effectiveness of the assay created, complete concentration curves for Palbociclib and Ribociclib were measured. HEK293/CDK DKO expressing E2F1-Dp-1-LB cells were transiently transfected with SB-Rb, CyclinD1, and CDK4 or CDK6, as previously indicated, and then treated for 24h with Palbociclib (FIG. 10A) or Ribociclib (FIG. 10B) at a range of concentrations covering 8 logs. Based on the results, EC50s were obtained for Palbociclib at ~22.8 nM and for Ribociclib at ~62.5 M for CDK4 and at ~17.3 nM and at ~90.5 nM for CDK6 respectively, using GraphPad Prism software (FIG. 10).

These values are comparable to a literature reported IC50 for Palbociclib in inhibiting phosphorylation of Rb (see Aleshin&Finn, 2016, BCR).

Example 13 Assay Validation by Using Known Kinase Dead and Unknown COSMIC Mutations To examine the ability of the assay to detect variants in CDK4 or CDK6 that affect function, kinase dead mutants and COSMIC (Catalogue Of Somatic Mutations in cancer) unknown mutants were created. For comparison, hyperactive CDK4 or CDK6 mutants known to be hyperactive due to less binding to natural inhibitor p16 were also created. The mutations in CDK4 or CDK6 were created by site-directed mutagenesis. The primers are indicated in Table 4. WT or mutated CDK4 or CDK6 along with the CyclinD1 and SB-Rb were co-transfected, under similar conditions as previously indicated (see FIG. 9). Over-expression of WT CDK4 or CDK6 exhibited the previously observed increase in Palbociclib-induced signal (FIG. 11). In addition, the hyperactive mutants R31C and R24C for CDK6 and CDK4, respectively, presented with a little bit lower basal signal than WT but not as close to zero as expected for the hyperactive mutant in the absence of drug treatment, which was indicative of greater phosphorylation of Rb, reducing the interaction with E2F1. However, these hyperactive mutants were considered hyperactive due to less binding to natural inhibitor p16, and yielding a greater fold-change in response to Palbociclib (as expected; see Tsao et al., 1998). Therefore the CDK4/CDK6 assay is capable of determining both CDK4 and CDK6 mutants' responsiveness to Palbociclib, Ribociclib, or Abemaciclib and the relative activity level of CDK4/CDK6 mutants.

Figure 12:
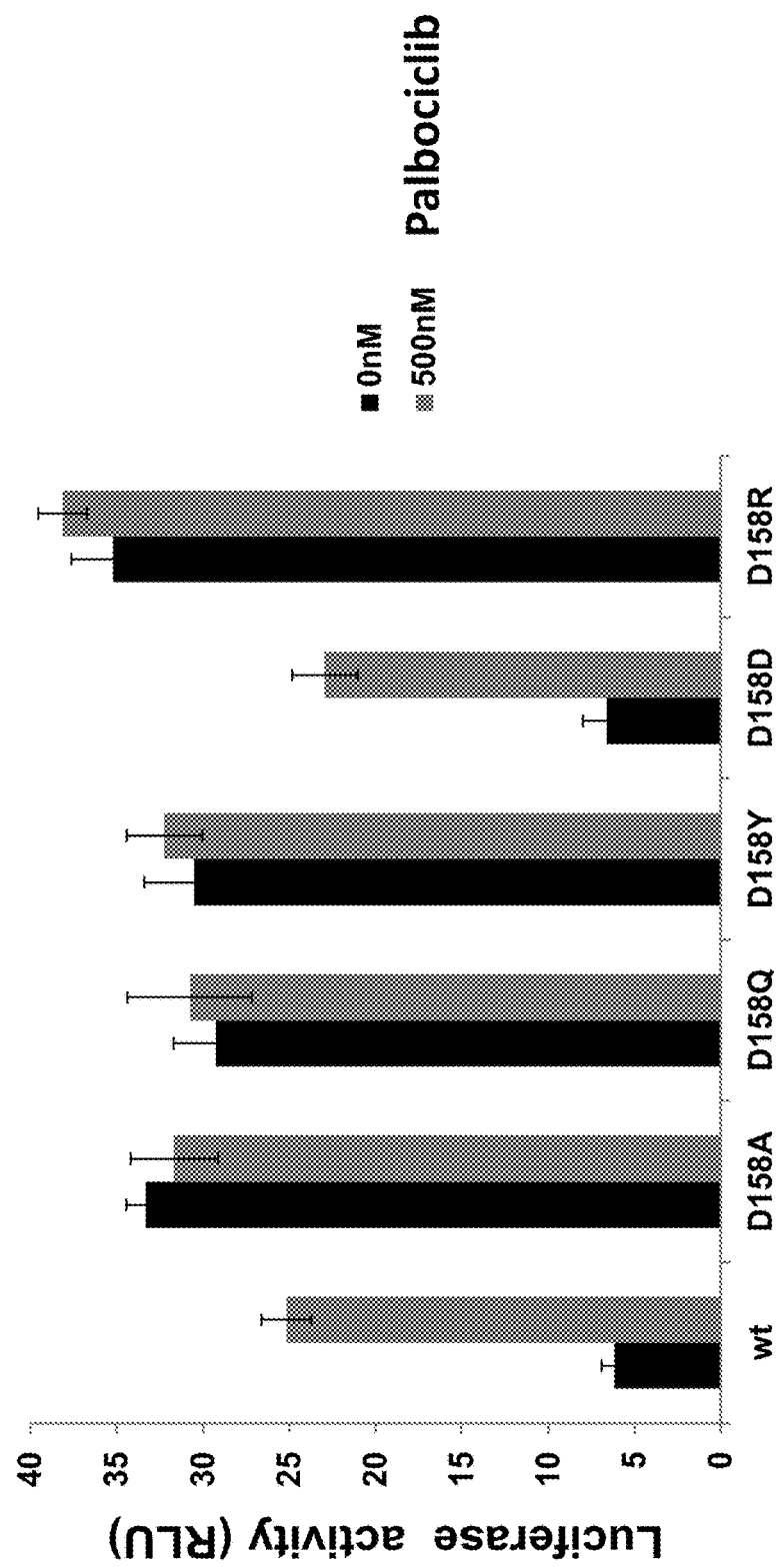
FIG. 12 shows relative luciferase activity of kinase dead CDK4 mutant with different amino acid substitutions at the same position exposed to Palbociclib.

Example 14 Assay Validation by Using Different Amino Acid Substitutions of the Kinase Dead Mutant at the D158 Residue To examine the specificity of the assay, particular CDK4 kinase dead mutants were created. Modifications to D158 were made by changing aspartate to nonpolar alanine (D158A) or positively charged arginine (D158R). D158D, with one nucleotide substitution that did not change the amino acid, was used as a control. The mutations in CDK4 were created by site-directed mutagenesis. The primers are indicated in Table 4. WT or mutated CDK4 along with the CyclinD1 and SB-Rb was co-transfected into the #11 cell line, under the same conditions as previously indicated. Over-expression of WT CDK4 exhibited a decrease in signal (FIG. 12). Kinase dead mutants have the high signal due to inability to phosphorylate Rb. The D158D mutant with one nucleotide substitution showed the same activity as a WT.

TABLE 4A

Primers for site-directed mutagenesis of CDK4

| CDK4 mutant | Forward primer | Reverse primer |
|---|---|---|
| K22M | TATGGGACAGTGTACATGGCCCGTGATCCCCAC [SEQ. ID. NO: 32] | GTGGGGATCACGGGCCATGTACACTGTCCCATA [SEQ. ID. NO: 33] |
| K22A | GCCTATGGGACAGTGTACGCGGCCCGTGATCCCCACAGT [SEQ. ID. NO: 34] | ACTGTGGGGATCACGGGCCGCGTACACTGTCCCATAGGC [SEQ. ID. NO: 35] |
| R24C | ACAGTGTACAAGGCCTGTGATCCCCACAGTGGC [SEQ. ID. NO: 36] | GCCACTGTGGGGATCACAGGCCTTGTACACTGT [SEQ. ID. NO: 37] |
| R24A | GCCTATGGGACAGTGTACAAGGCCGCGGATCCCCACAGT [SEQ. ID. NO: 38] | TATGGGACAGTGTACATGGCCCGTGATCCCCAC [SEQ. ID. NO: 39] |
| K35M | GGCCACTTTGTGGCCCTCATGAGTGTGAGAGTCCCCAAT [SEQ. ID. NO: 40] | ATTGGGGACTCTCACACTCATGAGGGCCACAAAGTGGCC [SEQ. ID. NO: 41] |
| K35R | GGCCACTTTGTGGCCCTCAGGAGTGTGAGAGTCCCCAAT [SEQ. ID. NO: 42] | ATTGGGGACTCTCACACTCCTGAGGGCCACAAAGTGGCC [SEQ. ID. NO: 43] |
| K155Q | ACAAGTGGTGGAACAGTCCAGCTGGCTGACTTTGGCCTG [SEQ. ID. NO: 44] | CAGGCCAAAGTCAGCCAGCTGGACTGTTCCACCACTTGT [SEQ. ID. NO: 45] |
| D158R | GTAGATTCTGGCCAGGCCAAACCGAGCCAGCTTGACTGTTCCACC [SEQ. ID. NO: 46] | GGTGGAACAGTCAAGCTGGCTCGGTTTGGCCTGGCCAGAATCTAC [SEQ. ID. NO: 47] |
| D158Q | GGAACAGTCAAGCTGGCTCAGTTTGGCCTGGCCAGAATC [SEQ. ID. NO: 48] | GATTCTGGCCAGGCCAAACTGAGCCAGCTTGACTGTTCC [SEQ. ID. NO: 49] |
| D158A | GGAACAGTCAAGCTGGCTGCCTTTGGCCTGGCCAGAATC [SEQ. ID. NO: 50] | GATTCTGGCCAGGCCAAAGGCAGCCAGCTTGACTGTTCC [SEQ. ID. NO: 51] |
| D158D | GGAACAGTCAAGCTGGCTGATTTTGGCCTGGCCAGAATC [SEQ. ID. NO: 52] | GATTCTGGCCAGGCCAAAATCAGCCAGCTTGACTGTTCC [SEQ. ID. NO: 53] |
| D158Y | GGAACAGTCAAGCTGGCTTACTTTGGCCTGGCCAGAATC [SEQ. ID. NO: 54] | GATTCTGGCCAGGCCAAAGTAAGCCAGCTTGACTGTTCC [SEQ. ID. NO: 55] |
| D158N | GGAACAGTCAAGCTGGCTTACTTTGGCCTGGCCAGAATC [SEQ. ID. NO: 56] | GATTCTGGCCAGGCCAAAGTAAGCCAGCTTGACTGTTCC [SEQ. ID. NO: 57] |
| S285C | CCACACAAGCGAATCTGTGCCTTTCGAGCTCTG [SEQ. ID. NO: 58] | CAGAGCTCGAAAGGCACAGATTCGCTTGTGTGG [SEQ. ID. NO: 59] |
| L161L | AAGCTGGCTGACTTTGGCTTGGCCAGAATCTACAGCTAC [SEQ. ID. NO: 60] | GTAGCTGTAGATTCTGGCCAAGCCAAAGTCAGCCAGCTT [SEQ. ID. NO: 61] |
| V137I | CTTCATGCCAATTGCATCATTCACCGAGATCTGAAGCCA [SEQ. ID. NO: 62] | TGGCTTCAGATCTCGGTGAATGATGCAATTGGCATGAAG [SEQ. ID. NO: 63] |
| V174M | CAGATGGCACTTACACCCATGGTTGTTACACTCTGGTAC [SEQ. ID. NO: 64] | GTACCAGAGTGTAACAACCATGGGTGTAAGTGCCATCTG [SEQ. ID. NO: 65] |
| V174G | CAGATGGCACTTACACCCGGGGTTGTTACACTCTGGTAC [SEQ. ID. NO: 66] | GTACCAGAGTGTAACAACCCCGGGTGTAAGTGCCATCTG [SEQ. ID. NO: 67] |

TABLE 4B

Primers for site-directed mutagenesis of CDK6

| CDK6 mutant | Forward Primer | Reverse Primer |
|---|---|---|
| R31C | GGGAAGGTGTTCAAGGCCTGCGA CTTGAAGAACGGAGGC [SEQ. ID. NO: 68] | GCCTCCGTTCTTCAAGTCGCAGGC CTTGAACACCTTCCC [SEQ. ID. NO: 69] |
| K43M | GGCCGTTTCGTGGCGTTGATGCGC GTGCGGGTGCAGACC [SEQ. ID. NO: 70] | GGTCTGCACCCGCACGCGCATCA ACGCCACGAAACGGCC [SEQ. ID. NO: 71] |
| R144H | CACCGAGTAGTGCATCACGATCT AAAACCACAG [SEQ. ID. NO: 72] | CTGTGGTTTTAGATCGTGATGCAC TACTCGGTG [SEQ. ID. NO: 73] |
| D163N | GGACAAATAAAACTCGCTAACTT CGGCCTTGCCCGCATC [SEQ. ID. NO: 74] | GATGCGGGCAAGGCCGAAGTTAG CGAGTTTTATTTGTCC [SEQ. ID. NO: 75] |
| P199L | TCCAGCTACGCCACCCTCGTGGAT CTCTGGAGT [SEQ. ID. NO: 76] | ACTCCAGAGATCCACGAGGGTGG CGTAGCTGGA [SEQ. ID. NO: 77] |
| R220C | CGTAGAAAGCCTCTTTTTTGTGGA AGTTCAGATGTTGAT [SEQ. ID. NO: 78] | ATCAACATCTGAACTTCCACAAAA AAGAGGCTTTCTACG [SEQ. ID. NO: 79] |
| R220S | CGTAGAAAGCCTCTTTTTAGTGGA AGTTCAGATGTTGAT [SEQ. ID. NO: 80] | ATCAACATCTGAACTTCCACTAAA AAGAGGCTTTCTACG [SEQ. ID. NO: 81] |

Example 15 Using Potential Resistant CDK4/6 Mutants to Check the Assay

Figure 13A:
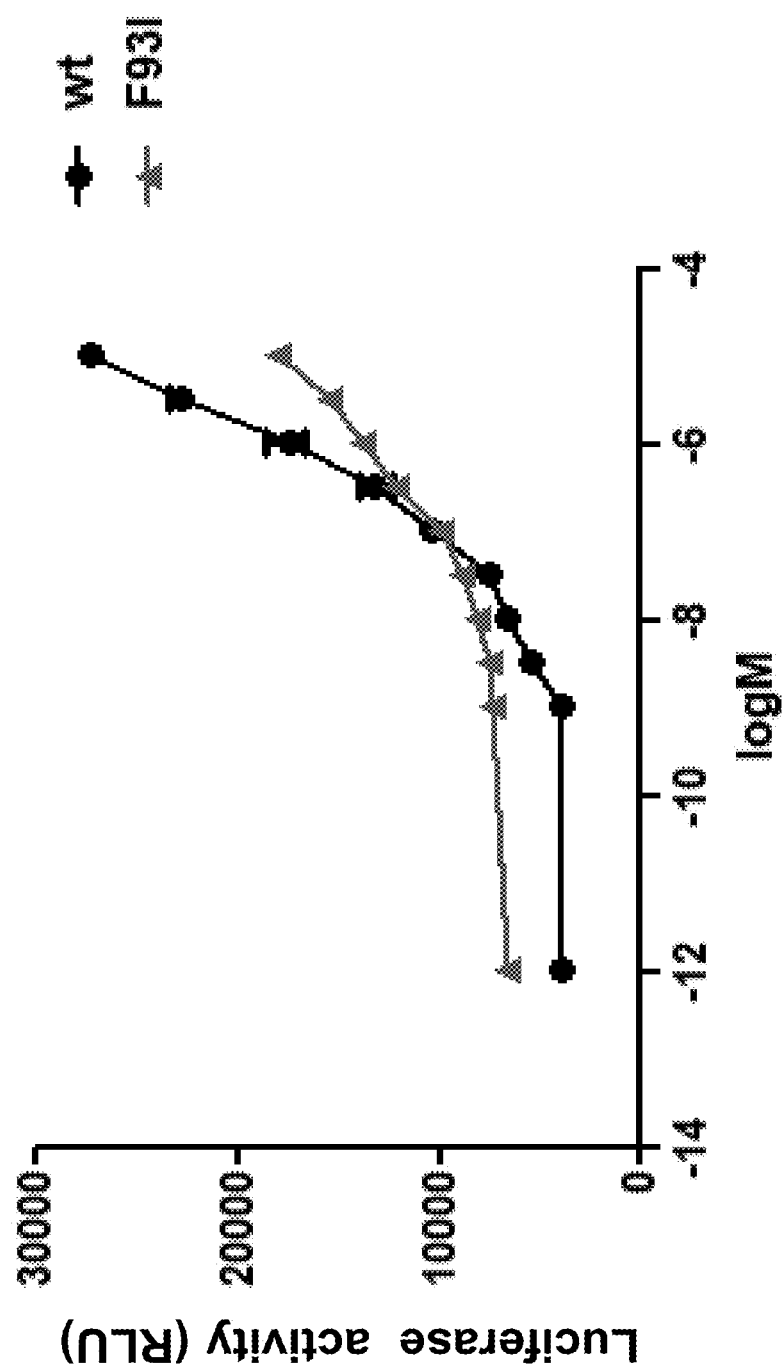
FIG. 13A shows a dose response curve for potential drug resistant CDK4 mutant F93I.
Figure 13B:
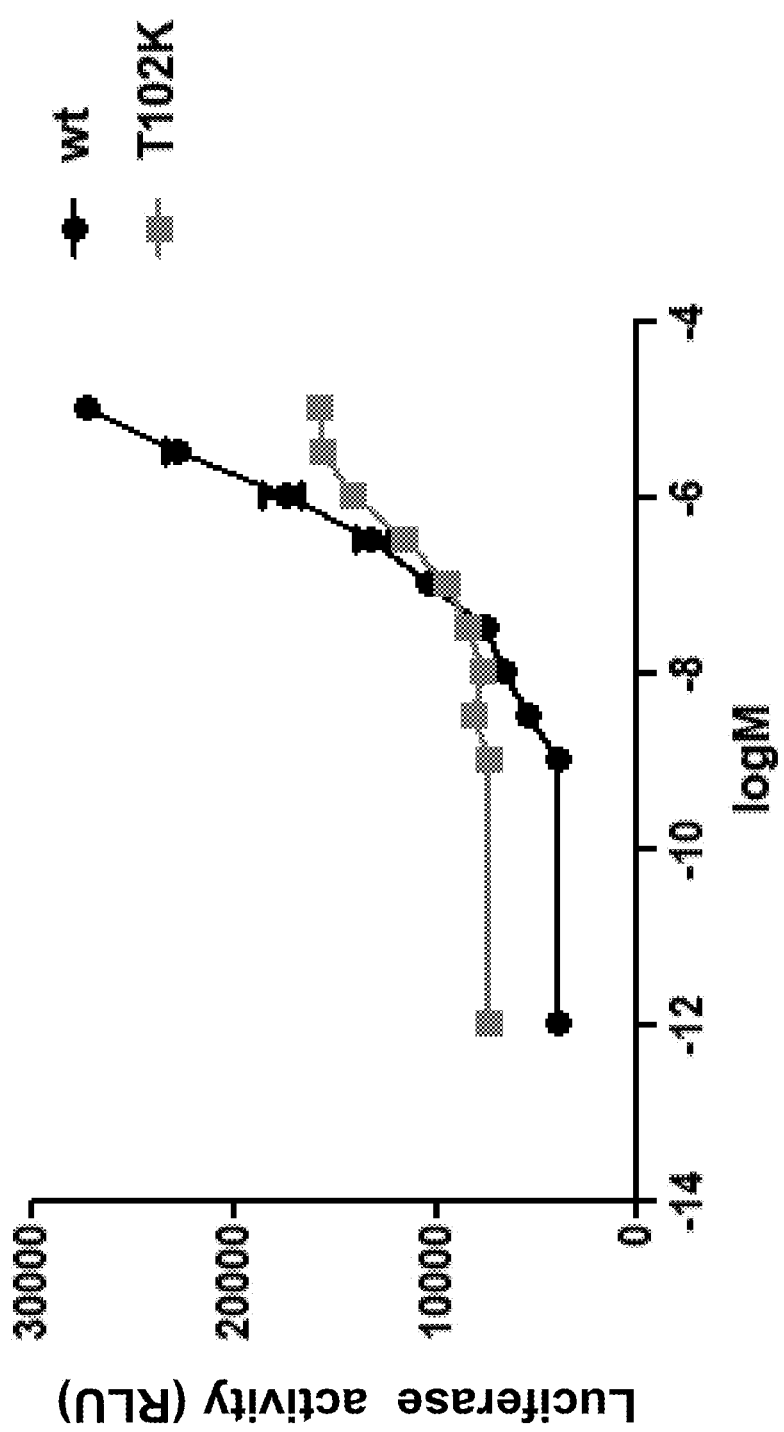
FIG. 13B shows dose response curve for another potential drug resistant CDK4 mutant T102K.
Figure 13C:
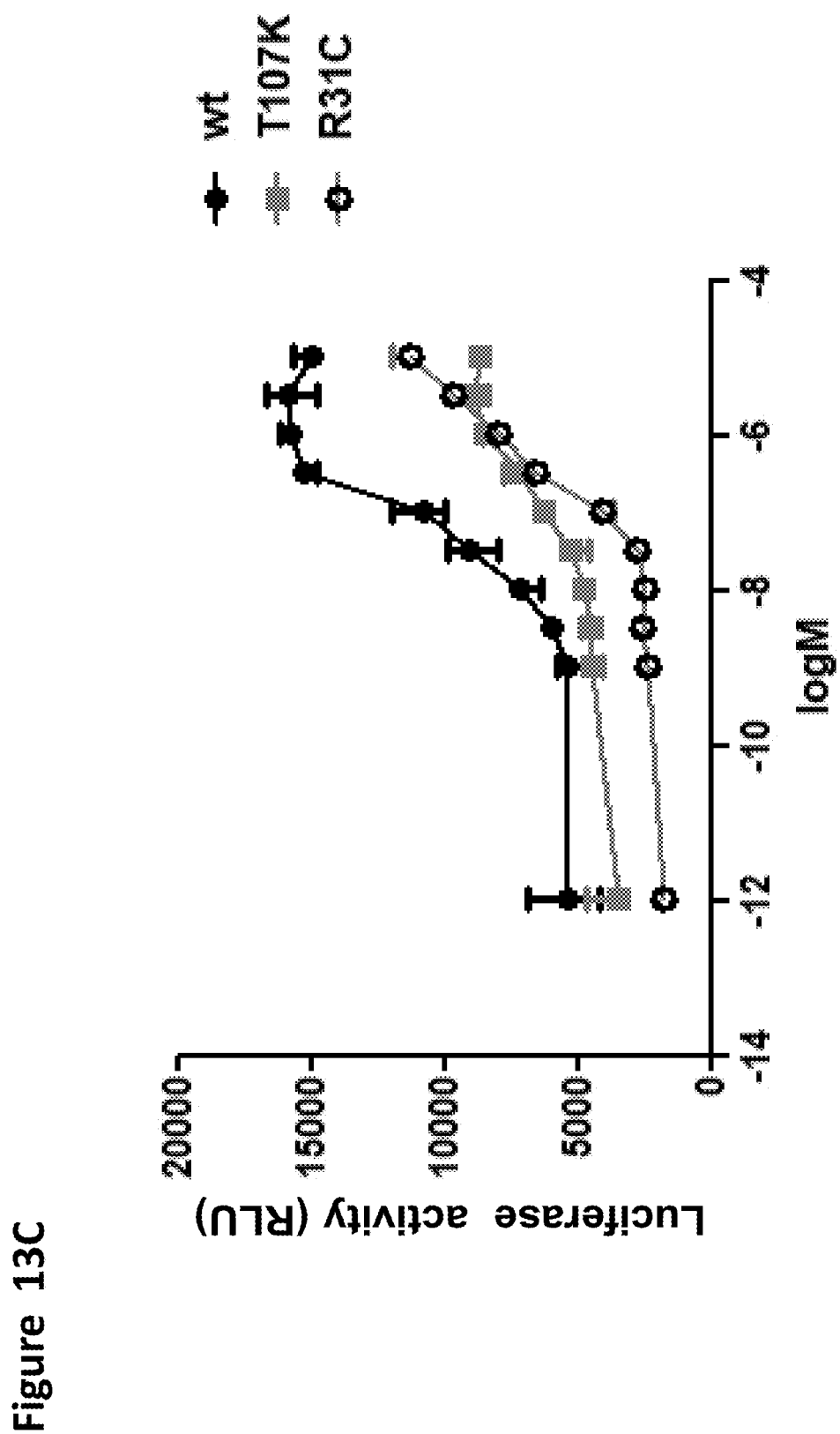
FIG. 13C shows dose response curve for potential drug resistant CDK6 mutant T107K.
Figure 14:
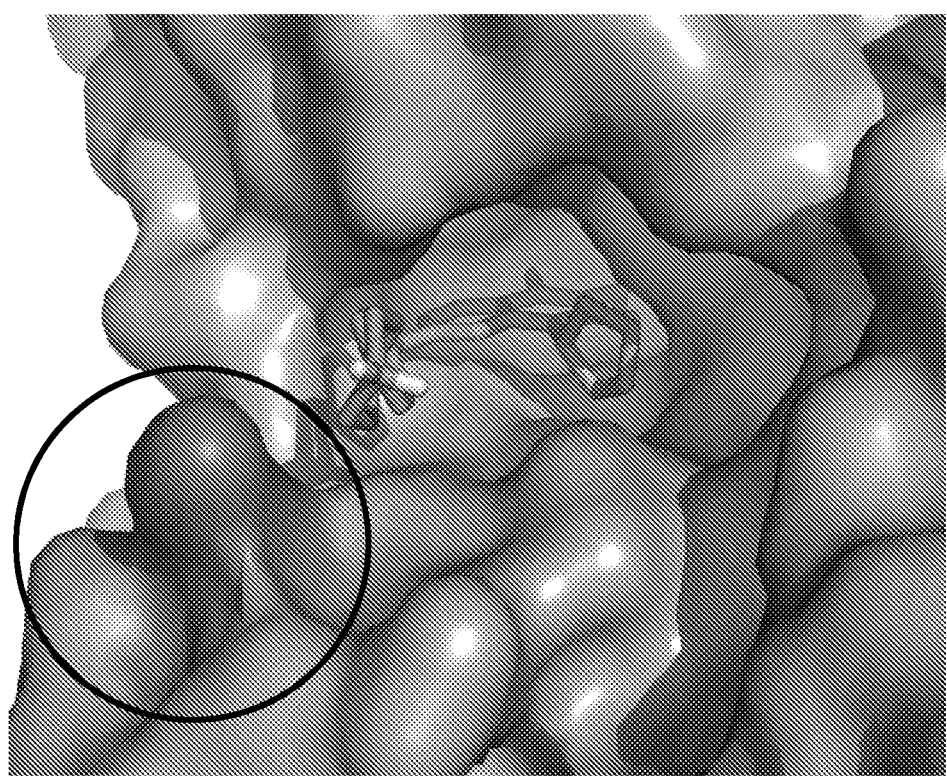
FIG. 14 shows a structural representation of the inhibitor binding channel of CDK6 and specific T107 amino acid residue shown inside the circle.

Since there is no information regarding CDK4 or CDK6 mutations causing drug resistance, potential resistant mutants were created based on available crystal structures of CDK4 and CDK6 with CyclinD1 and Ribociclib. Computer modeling was used to reveal the drug-binding pocket and predict drug-resistant mutants. The mutations in CDK4 and CDK6 were created by site-directed mutagenesis. The primers are indicated in Table 5. WT or mutated CDK4 or CDK6 along with the CyclinD1 and SB-Rb was co-transfected into #11 cell line, under the same conditions as previously indicated. A summary of all predicted CDK4 and CDK6 mutants that can affect either ATP, or CyclinD1 binding is presented in Table 6. Of the mutations created, two mutants for CDK4, F93I and T102K, and one mutant for CDK6, T107K, showed drug resistance. Dose response curves are presented on FIG. 13A and FIG. 13B. Activity of other mutants was very similar to the WT or KD. Mutants T102K for CDK4 or T107K for CDK6 do not directly interact with either Palbociclib or Ribociclib, but mutation of Thr to Lys places the positively charged Lys amino group in proximity to the positively charged amino group of both Palbociclib and Ribociclib, leading to an electrostatic repulsion and thus drug displacement (FIG. 14).

TABLE 5A

Primers for site-directed mutagenesis of predicted CDK4 mutants causing resistance

| CDK4 mutant | Forward Primer | Reverse Primer |
|---|---|---|
| A162V | CTGGCTGACTTTGGCCTGGTCAG AATCTACAGCTACCAGATG [SEQ. ID. NO: 82] | CATCTGGTAGCTGTAGATTCTGAC CAGGCCAAAGTCAGCCAG [SEQ. ID. NO: 83] |
| I51F | GGTGGAGGAGGCCTTCCCtTCAGC ACAGTTCGTGAGGTG [SEQ. ID. NO: 84] | CACCTCACGAACTGTGCTGAaGGG AAGGCCTCCTCCACC [SEQ. ID. NO: 85] |
| T102K | GTAGACCAGGACCTAAGGAaATA TCTGGACAAGGCACCC [SEQ. ID. NO: 86] | GGGTGCCTTGTCCAGATATtCCTT AGGTCCTGGTCTAC [SEQ. ID. NO: 87] |
| T102R | CATGTAGACCAGGACCTAAGGAg ATATCTGGACAAGGCACCC [SEQ. ID. NO: 88] | GGGTGCCTTGTCCAGATATcTCCT TAGGTCCTGGTCTACATG [SEQ. ID. NO: 89] |
| L49R | GGAGGAGGTGGAGGAGGCCgTCC CATCAGCACAGTTCGT [SEQ. ID. NO: 90] | ACGAACTGTGCTGATGGGAcGGCC TCCTCCACCTCCTCC [SEQ. ID. NO: 91] |

TABLE 5A-continued

Primers for site-directed mutagenesis of predicted
CDK4 mutants causing resistance

| CDK4 mutant | Forward Primer | Reverse Primer |
|---|---|---|
| I12L | TCTCGATATGAGCCAGTGGCTGA ACTTGGTGTCGGTGCCTATGGG [SEQ. ID. NO: 92] | CCCATAGGCACCGACACCAAGTT CAGCCACTGGCTCATATCGAGA [SEQ. ID. NO: 93] |
| G18A | ATTGGTGTCGGTGCCTATGcGACA GTGTACAAGGCCCGT [SEQ. ID. NO: 94] | ACGGGCCTTGTACACTGTCgCATA GGCACCGACACCAAT [SEQ. ID. NO: 95] |
| A33S | CACAGTGGCCACTTTGTGtCCCTC AAGAGTGTGAGAGTC [SEQ. ID. NO: 96] | GACTCTCACACTCTTGAGGGaCAC AAAGTGGCCACTGTG [SEQ. ID. NO: 97] |
| F93I | ATCAAGGTAACCCTGGTGaTTGA GCATGTAGACCAGGAC [SEQ. ID. NO: 98] | GTCCTGGTCTACATGCTCAAtCAC CAGGGTTACCTTGAT [SEQ. ID. NO: 99] |
| A157S | GGTGGAACAGTCAAGCTGtCTGA CTTTGGCCTGGCCAGA [SEQ. ID. NO: 100] | TCTGGCCAGGCCAAAGTCAGaCAG CTTGACTGTTCCACC [SEQ. ID. NO: 101] |

TABLE 5B

Primers for site-directed mutagenesis of predicted
CDK6 mutants causing resistance

| CDK6 mutant | Forward Primer | Reverse Primer |
|---|---|---|
| A162S | AGCGGACAAATAAAACTCGtTGACT TCGGCCTTGCCCGC [SEQ. ID. NO: 102] | GCGGGCAAGGCCGAAGTCAaCGA GTTTTATTTGTCCGCT [SEQ. ID. NO: 103] |
| L152V | CTAAAACCACAGAACATTgTGGTGA CCAGCAGCGGACAA [SEQ. ID. NO: 104] | TTGTCCGCTGCTGGTCACCAcAAT GTTCTGTGGTTTTAG [SEQ. ID. NO: 105] |
| T107K | GTCGATCAAGACTTGACCAaaTACTT GGATAAAGTTCCA [SEQ. ID. NO: 106] | TGGAACTTTATCCAAGTAttTGGTC AAGTCTTGATCGAC [SEQ. ID. NO: 107] |
| D104N | TTTGAACATGTCGATCAAaACTTGA CCACTTACTTGGAT [SEQ. ID. NO: 108] | ATCCAAGTAAGTGGTCAAGTtTTG ATCGACATGTTCAAA [SEQ. ID. NO: 109] |
| H100Y | CTAACTTTAGTGTTTGAAtATGTCGA TCAAGACTTGACC [SEQ. ID. NO: 110] | GGTCAAGTCTTGATCGACATaTTC AAACACTAAAGTTAG [SEQ. ID. NO: 111] |
| F98I | ACCAAACTAACTTTAGTGaTTGAAC ATGTCGATCAAGAC [SEQ. ID. NO: 112] | GTCTTGATCGACATGTTCAAtCACT AAAGTTAGTTTGGT [SEQ. ID. NO: 113] |
| A41V | AACGGAGGCCGTTTCGTGGtGTTGA AGCGCGTGCGGGTG [SEQ. ID. NO: 114] | CACCCGCACGCGCTTCAACaCCAC GAAACGGCCTCCGTT [SEQ. ID. NO: 115] |
| V27A | GAGGGCGCCTATGGGAAGGcGTTCA AGGCCCGCGACTTG [SEQ. ID. NO: 116] | CAAGTCGCGGGCCTTGAACgCCTT CCCATAGGCGCCCTC [SEQ. ID. NO: 117] |
| I19L | TACGAATGCGTGGCGGAGcTCGGGG AGGGCGCCTATGGG [SEQ. ID. NO: 118] | CCCATAGGCGCCCTCCCCGAgCTC CGCCACGCATTCGTA [SEQ. ID. NO: 119] |

TABLE 6A

Summary table of predicted drug resistant CDK4 mutants

| | T102K | A33S | F93I | G18A | A157S | T102R | L49R | I51F | A162V | I12L | F93I T102K |
|---|---|---|---|---|---|---|---|---|---|---|---|
| Literature ref. | | | | | | | | | | | |
| COSMIC database count | * | | | * | | | | | | | |
| type of cancer | 1 squamous cell carcinoma | | | 1 uterine corpus end. carcinoma | | | | | | | |
| Observed drug resist. | Resistant | | Resistant | | | | KD | KD | | | Resistant |
| Luc. activity (/wt) | 162 | 182 | 157 | 97.5 | 195 | 156 | 281 | 160 | 254 | 126 | 152 |

TABLE 6B

Summary table of predicted drug resistant CDK6 mutants

| | T107K | I19L | F98I | D104N | L152V | A41V | H100Y | A162V | V27A |
|---|---|---|---|---|---|---|---|---|---|
| Literature ref. | | | | | | | | | |
| COSMIC database count | | | | | | | | | |
| type of cancer | | | | | | | | | |
| Observed drug resist. | Resistant | | | | | | | | |
| Luc. activity (/wt) | 95 | 129 | 176 | 138 | 114 | 132 | 126 | 148 | 149 |

Example 16 Assay Validation by Using COSMIC Mutations and Creating Our Own Database CDK4 and CDK6 mutants with known function and unknown function taken from the COSMIC database were analyzed in the present assay and are summarized in Table 7A and Table 7B. The mutants were classified according to their activity. Table 7A and Table 7B also show the number of counts per mutant in the COSMIC database, type of cancer, and luciferase activity compared to the WT (being 100%).

TABLE 7A

Summary table of all CDK4 mutants checked

| | | K22A | R24A | | | K35M | | |
|---|---|---|---|---|---|---|---|---|
| Literature ref. | | K22A | R24A | | | K35M | | |
| COSMIC database | K22M | | | R24S | R24C | | K35R | V137I |
| count | 2 | 0 | 0 | 2 | 2 | 0 | 1 | 2 |
| type of cancer | melanoma | | | melanoma | melanoma | uterine carcinoma | colon | breast inv. carcinoma |
| Reported activity | | Hyper | Hyper | | | KD | | |
| Luc. activity (/wt) | 141 | 67.5 | 79 | 117 | 91 | 350 | 310 | 120 |
| Literature ref. | | | | D158N | | | | |
| COSMIC database | K155Q | D158Y | | L161L (C-T) | V174G | V174M | R210Q | S285C |

TABLE 7A-continued

Summary table of all CDK4 mutants checked

| count type of cancer | 1 prostate | 1 | 0 | 2 leukemia | 1 uterine carcinoma | 1 oral carcinoma | 2 colo-rectal | 2 gallbladder carcinoma |
|---|---|---|---|---|---|---|---|---|
| Reported activity | | | KD | | | | | |
| Luc. activity (/wt) | 130 | 230 | 300 | 59 | 129 | 47 | 74.5 | 125 |

TABLE 7B

Summary table of all CDK6 mutants checked

| Literature ref. | R31C | K43M | | D163N | | | |
|---|---|---|---|---|---|---|---|
| COSMIC database | | | R144H | | P199L | R220C | R220S |
| count type of cancer | 0 | 0 | 2 colo-rectal | 0 | 2 melanoma | 2 colon melanoma | 1 colo-rectal |
| Reported activity | Hyper | KD | | KD | | | |
| Luc activity (/wt) | 66 | 468 | 267 | 408 | 565 | 164 | 271 |

Example 17 Next-Generation Sequencing to Interrogate Mutation of Tumor for Rb Assay Since loss of Rb function is frequent in different types of cancer, knowing the gene mutations and drug resistance would be beneficial in cancer therapy. To survey the mutation status of the RB gene, whole exome sequencing was performed. Genomic DNA was extracted and used to prepare a library for NGS. The identified mutations, which caused changes in amino acid sequence, were picked to examine their functional effect on the gene in the cell-based assay described below. The patient gene carrying the identified mutation was constructed using a PCR mediated overlapping extension in the format of a linear expression cassette.

Example 18 Construction of Linear Expression Cassette of Human RB

In order to study the effect of unknown mutations in the human RB gene, a linear expression cassette containing the CMV promoter that controls RB expression and coding sequence of RB was generated followed by terminator and polyadenylation signaling. Overlapping extension PCR was employed to construct the linear expression cassette using expression plasmid of human RB as a PCR template. By employing this method, the construction of the linear expression cassette took around 4-8 hours in comparison to the traditional cloning method to generate expression plasmid which takes around 2-4 days. Therefore, making a patient gene in a linear expression cassette format was beneficial because of its quick turn-around time.

Example 19 Construction of Expression Plasmids for Rb Assay

The coding sequences of commercially-available cDNA plasmids encoding human RB and DP1 genes (Dharmacon) were amplified by PCR. Different restriction enzyme sites to forward and reverse primers, respectively, were inserted for purposes of cloning (Table 8). PCR products containing the coding sequences of human RB and DP1 were sub-cloned into the pcDNA 3.1 (+) vector. The nucleotide sequences of all genes were verified by DNA sequencing. Constructed RB expression plasmid was used as a PCR template to provide linear expression cassettes of wild-type (WT) or mutated forms of RB.

TABLE 8

Primers used for RB expression plasmids

| | |
|---|---|
| RB BamHI F | TAATGGATCCGCCGCCACCATGCCGCCCAAAACC [SEQ. ID. NO: 120] |
| RB XhoI R | GCGGCTCGAGTCATTTCTCTTCCTTGTTTGAGG [SEQ. ID. NO: 121] |
| DP1 NheI F | TGGCTAGCCGCCACCATGGCAAAAGATGCCGGTCTAATT [SEQ. ID. NO: 122] |
| DP1 XhoI R | GACTCGAGTCAGTCGTCCTCGTCATTCTC [SEQ. ID. NO: 123] |

Generation of Linear Expression Cassette of WT and Mutated RB

A linear expression cassette of human WT RB was generated by UF-CMV forward and BGH-UR reverse primers. The amplified products were gel-purified. The DNA concentration was quantitated by optical density at 260 nm using Nanodrop.

Figure 15:
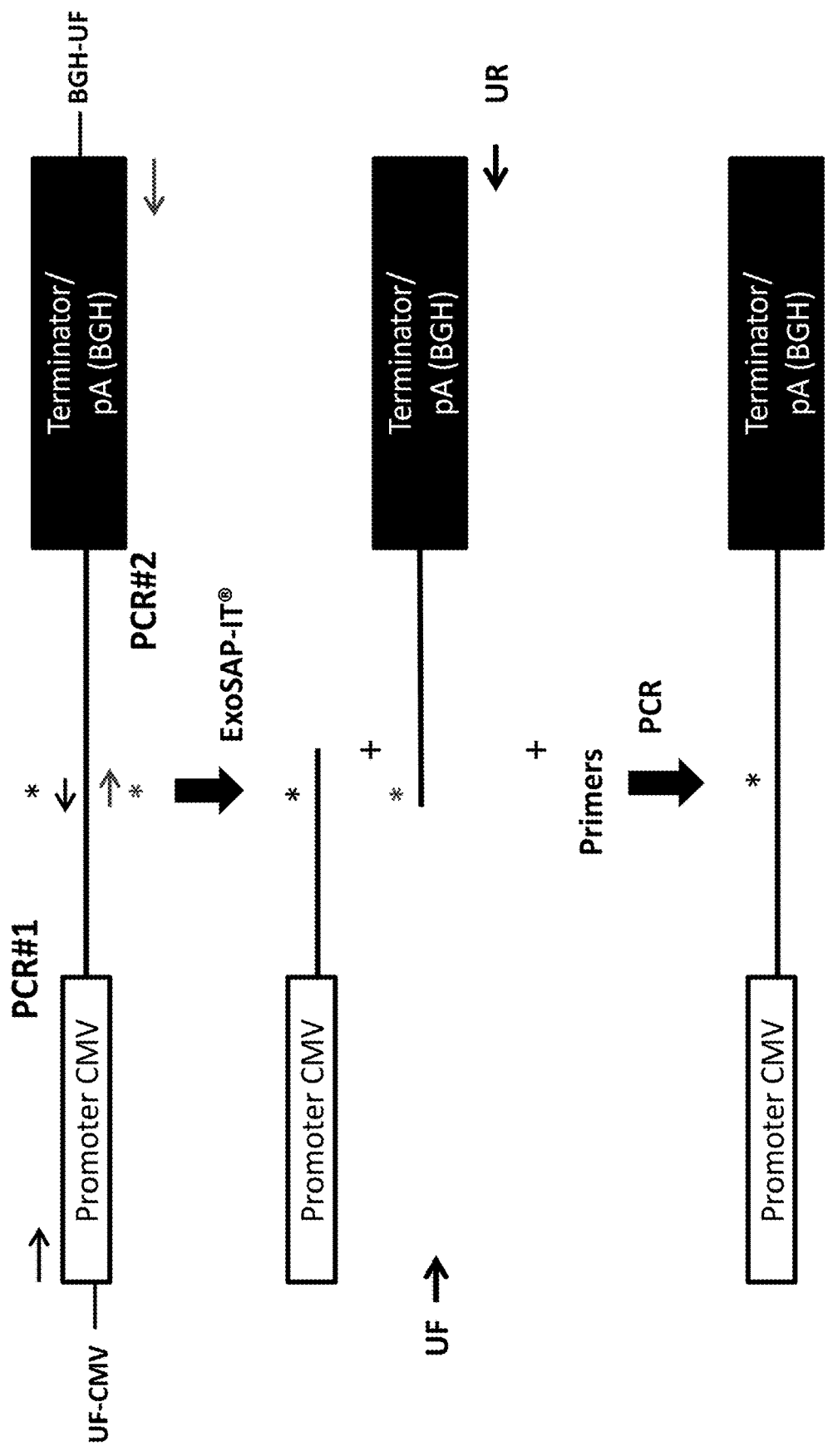
FIG. 15 shows a schematic representation of a PCR-mediated overlapping extension method used for all linear Rb constructs.

A linear expression cassette of mutated RB was generated by PCR via the mediated overlapping extension method. A pair of forward and reverse primers containing the targeted mutations was designed. The mutated codon (3 nucleotides) was located in the middle of the primer flanked by 18-21 nucleotides on each side. Two separate PCRs, named PCR #1 and PCR #2 in FIG. 15, were performed using UF-CMV forward and mutated reverse primers, or mutated forward and BGH-UR primers, respectively. The PCR products were purified via ExoSAP-IT® (Affymetrix) to remove unconsumed dNTPs and primers. The two treated PCR products were mixed together and the mixture was diluted with water. A second round of PCR was performed using the diluted PCR mixture, and UF and UR primers (FIG. 15). The amplified products were gel-purified. The DNA concentration was quantitated by optical density at 260 nm using Nanodrop. The targeted mutations were successfully incorporated into the RB gene during the PCR mediated overlapping extension methods and confirmed by DNA sequencing.

Example 20 Transfection Method

In the described Rb assay, a so called reverse transfection protocol was used whereby freshly passaged HEK293 cells were added to the transfection complexes in order to reduce the hands-on time for the end user. In this scenario, the HEK293 cells were not adhered to the plate surface by the time they interacted with the transfection complexes.

Example 21 Interacting Partners for Rb Activity Assay

An assay that could measure the interaction between Rb, E2F1, and Dp-1 was developed. Since Dp-1 forms a heterodimer with E2F1 and that interaction is crucial for Rb/E2F1 binding, the assay was comprised of three components. When two proteins (Rb and E2F1) are in close proximity or in complex, a light signal was observed. For the purposes of the current assay, split-luciferase complementation was used to measure the interaction between Rb and E2F1. The NanoBiT assay system by Promega (Madison, Wis.; Dixon et al., 2015, ACS ChemBiol) was used in our split luciferase complementation design.

Figure 16:
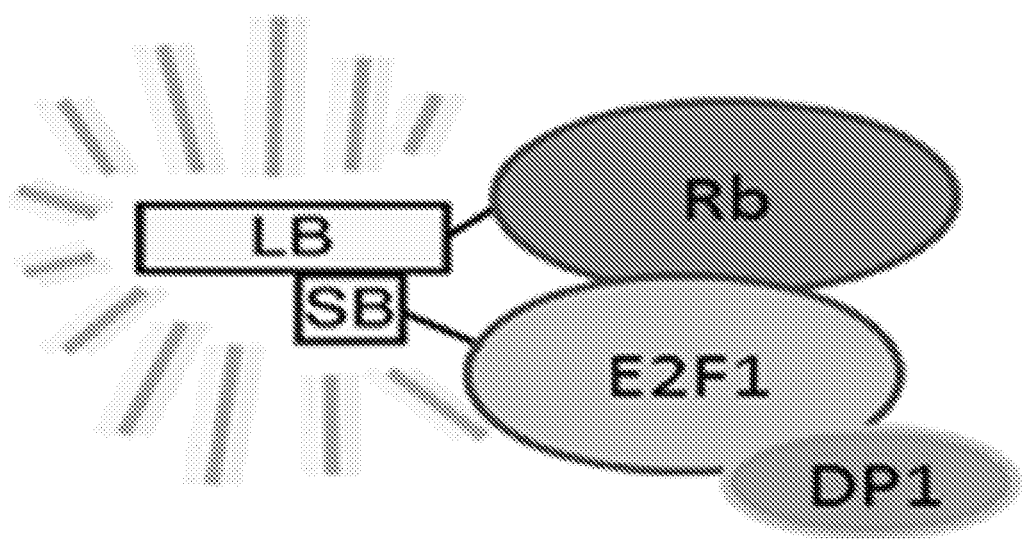
FIG. 16 shows a schematic representation of the NanoBit (Split Luciferase) design.

FIG. 16 depicts the design of a signal system to measure Rb activity. Under basal conditions inside the cell, Rb was active and interacted with the E2F1/Dp-1 heterodimer. For this assay design, cDNAs of Rb linked to different parts of the luciferase protein, either termed as the "Small BiT" (SB), or "Large BiT" (LB) and E2F1 linked to the opposite portion of the luciferase protein were created. When Rb and E2F1/Dp-1 bind, the NanoBiT parts of the luciferase form a complex and emitted a light signal when the luciferase (NanoGlo) substrate was added.

PCR was performed to ligate cDNAs fragments of RB and E2F1 into NanoBiT designed vectors MCS-1, MCS-2, MCS-3, and the MCS-4, respectively (Promega). Oligonucleotide primers used for subcloning are indicated in Table 9.

represents a sample experiment where each condition was performed in triplicate and represent mean+SD. According to the data, a higher luciferase activity was observed for the LB-Rb and E2F1-SB, DP1 constructs in Rb 379-928 activity assay, and Rb-LB and SB-E2F1, DP1 constructs for Rb full length activity assay (only used when there is a need for N-terminal Rb assessment).

Example 23 Rb Assay Validation by Using Known Null Mutants

Figure 18A:
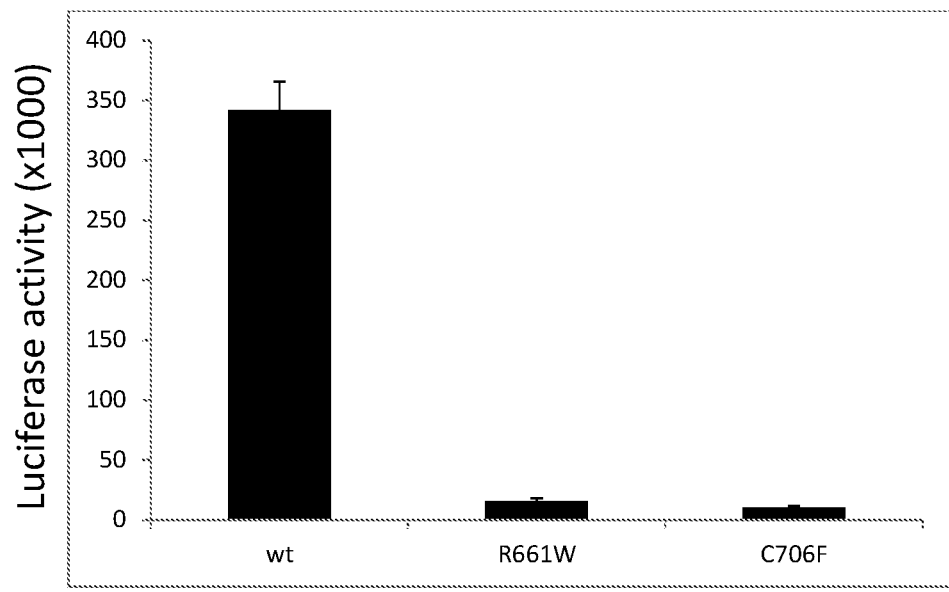
FIG. 18A shows the validation of Rb activity assay by checking known Rb null mutants using the LB-Rb and E2F1-SB, DP1constructs. Absence of luciferase signal in the R661W and C706F mutants show loss of activity.
Figure 18B:
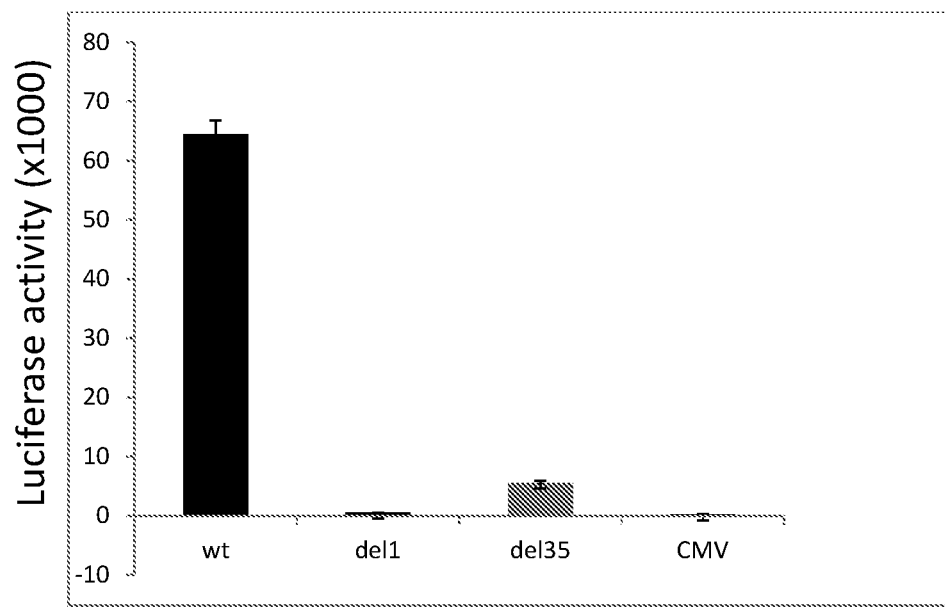
FIG. 18B shows the validation of Rb activity assay by using in- and out-of frame deletion mutants and the LB-Rb and E2F1-SB, DP1 constructs. Absence of luciferase signal shows the loss of function of Rb protein.

The LB-Rb and E2F1-SB with Dp-1 were tested for Rb activity using known Rb null mutants: R661W and C706F (FIG. 18A). Rb point mutants R661W and C706F completely disrupted the E2F1 interaction and a resulting decrease in luciferase activity was observed. Rb in-frame (del35) and out-of frame (del1) deletion mutants (FIG. 18B) were constructed and the observed luciferase activity was close to 0, in particular for del1 mutant, because Rb-E2F1 binding was destroyed.

Example 24 Selection of Stable Cell Clones Carrying E2F1-SB and DP1

Figure 19A:
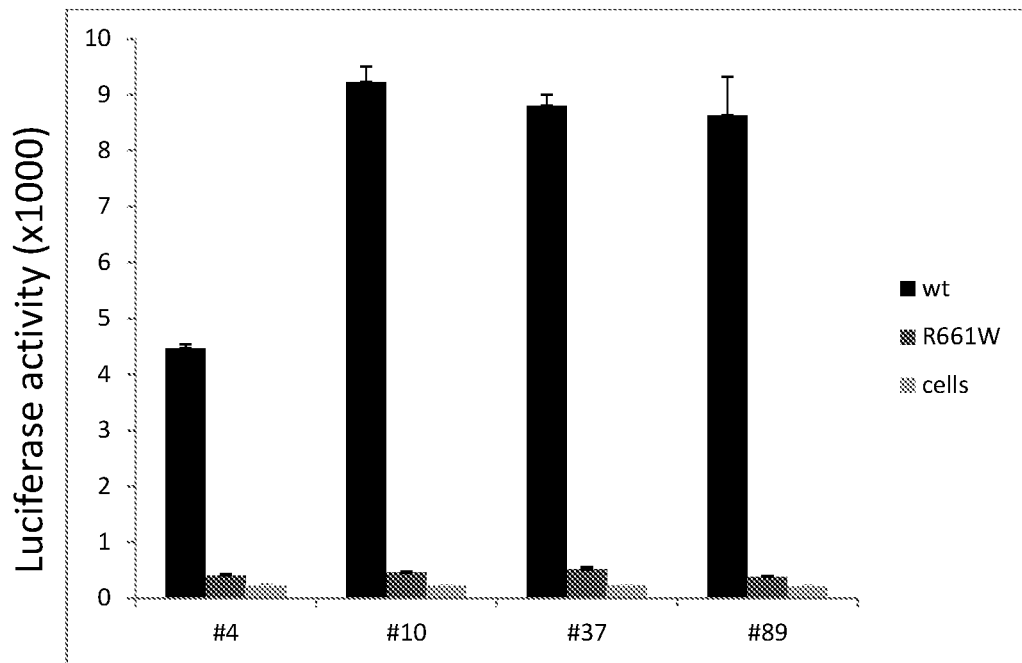
FIG. 19A shows the validation of stable cell clones by using WT Rb and known Rb null mutant.
Figure 19B:
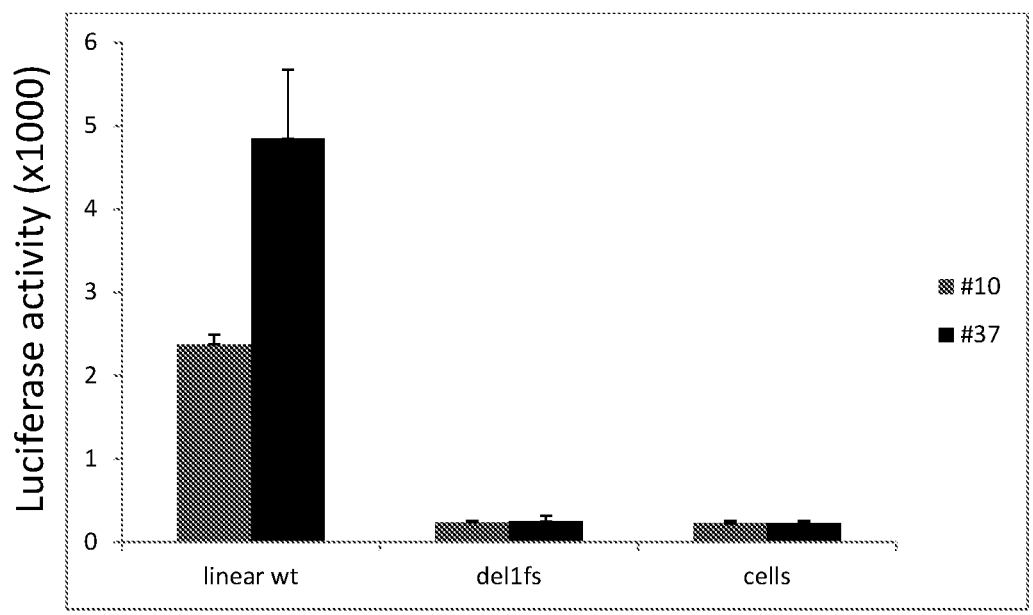
FIG. 19B shows the validation of stable cell clones by using an out of frame Rb deletion mutant.

Within the provided assay design, stable cell lines using the HEK293 CDK DKO cell parent line expressing E2F1-SB and Dp-1 were produced. After selection and screening for positive clones using an LB-Rb-mediated increase in signal, four stable single cell clones were selected and evaluated using different Rb mutants (FIGS. 19A and 19B). The response to E2F1 interaction was also checked by using the plasmid and linear form of DNA. Cell line #37 was selected for all our experiments in assay development due to its favorable response.

TABLE 9

Primers designed for subcloning RB and E2F1 cDNA constructs into NanoBiT vectors

| Target/Purpose | Forward Primer | Reverse Primer |
| --- | --- | --- |
| E2F1-LB, E2F1-SB into MCS-1, MCS-2 using Hind III and EcoRI | CT AAGCTT GCC ACC ATG CTC GAC TAC CAC TTC GGC CT [SEQ. ID. NO: 124] | C AGA ATT CCC CTC CTC AGG GCA CAG GAA AAC [SEQ. ID. NO: 125] |
| RB-LB, RB-SB into MCS-1, MCS-2 using Hind III and EcoRI | CT AAGCTT GCC ACC ATG TAT GCT TCC ACC AGG CCC CCT [SEQ. ID. NO: 126] | C AGA ATT CCC TTT CTC TTC CTT GTT TGA GGT ATC CAT [SEQ. ID. NO: 127] |
| LB-E2F1, SB-E2F1 into MCS-3, MCS-4 using EcoRI and XbaI | AAT TCA CTAGG C GAC TAC CAC TTC GGC CT [SEQ. ID. NO: 128] | AC TCT AGA TTA CTC CTC AGG GCA CAG GAA AAC [SEQ. ID. NO: 129] |
| LB-RB, SB-RB into MCS-3, MCS-4 using EcoRI and XbaI | AGG AAT TCA TAT GCT TCC ACC AGG CCC CCT [SEQ. ID. NO: 130] | AC TCT AGA TTA TTT CTC TTC CTT GTT TGA GGT ATC CAT [SEQ. ID. NO: 131] |

Example 22 Designing Interacting Pairs for the Rb Assay

Figure 17:
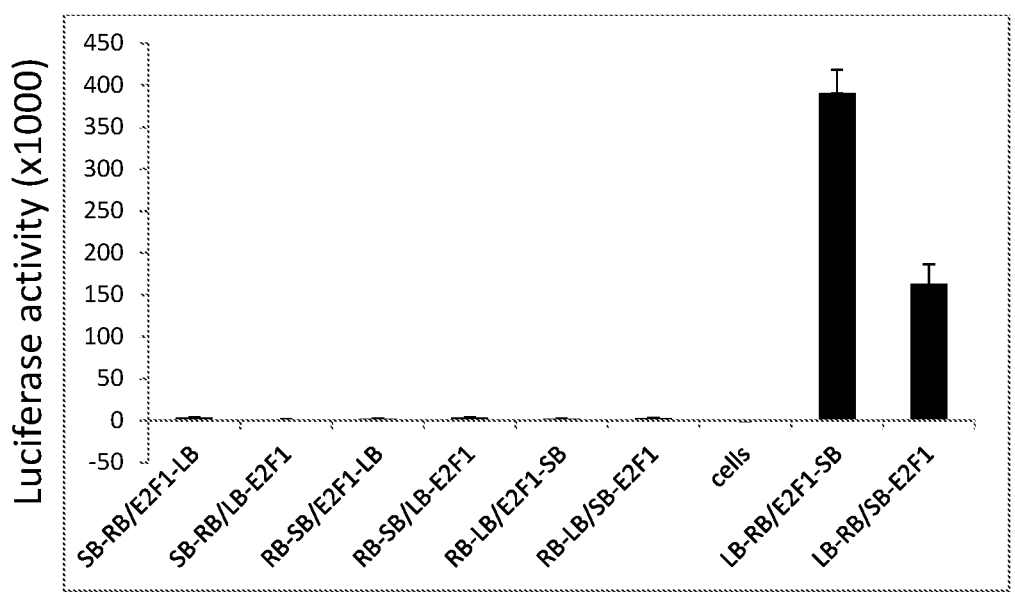
FIG. 17 shows the NanoBit constructs for Rb activity in the Rb assay.

Using the described assay design, HEK293 CDK DKO cells were transiently transfected with different combinations of SB-Rb or LB-Rb and E2F1-LB or E2F1-SB components containing C-terminal and N-terminal constructs (FIG. 17). Relative intensities generated are presented in FIG. 17 as relative luminescence units (RLU). The data

Figure 20:
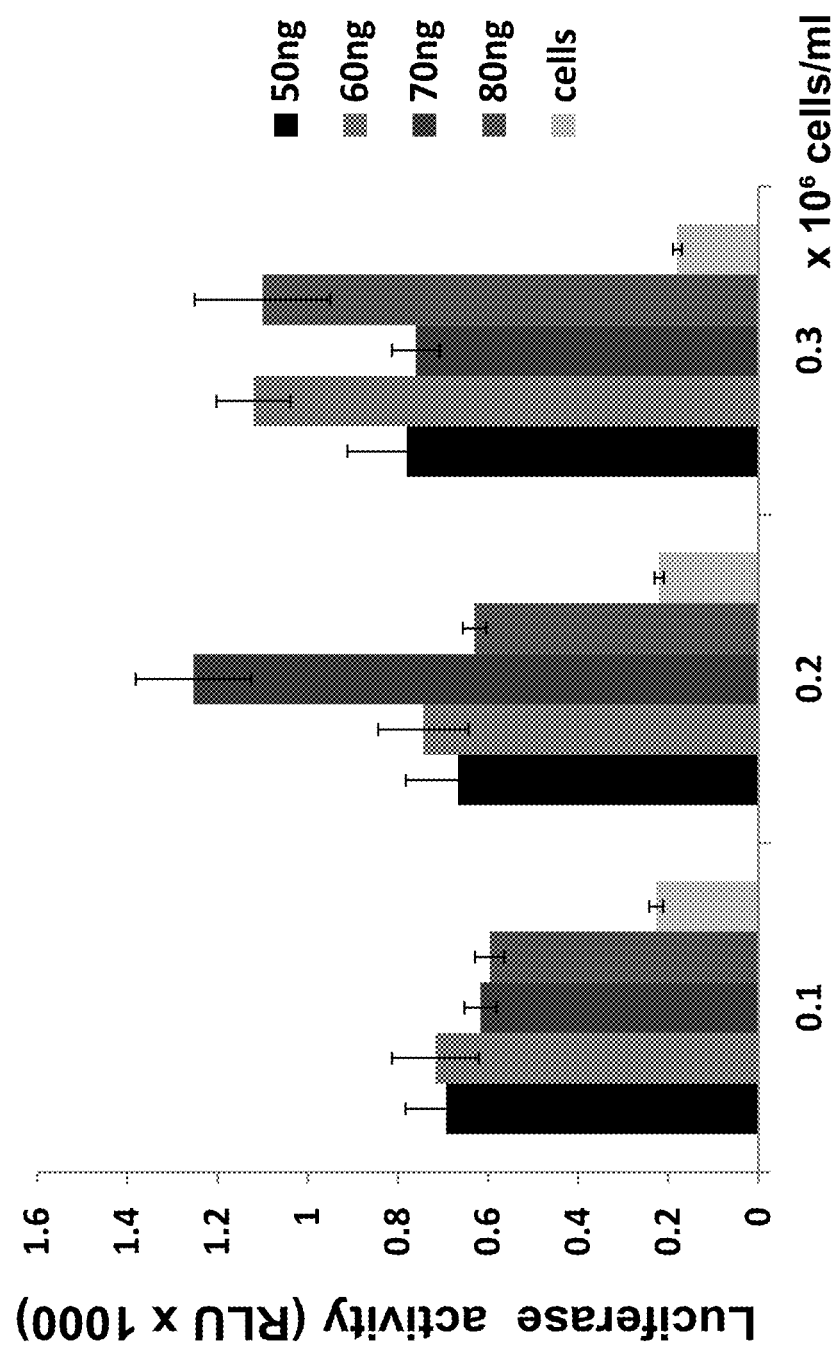
FIG. 20 shows optimization of Rb activity assay by checking different amounts of cells and the amount of transfected Rb linear construct.

Example 25 Rb Assay Optimization by Checking Different Cell Number and Rb Amount The conditions of the assay were further optimized by analyzing different cell numbers and Rb concentrations (FIG. 20). Based on the data, it was decided to use $0.2 \times 10^6$ cells/ml and 70 ng of DNA in the assay.

Figure 21:
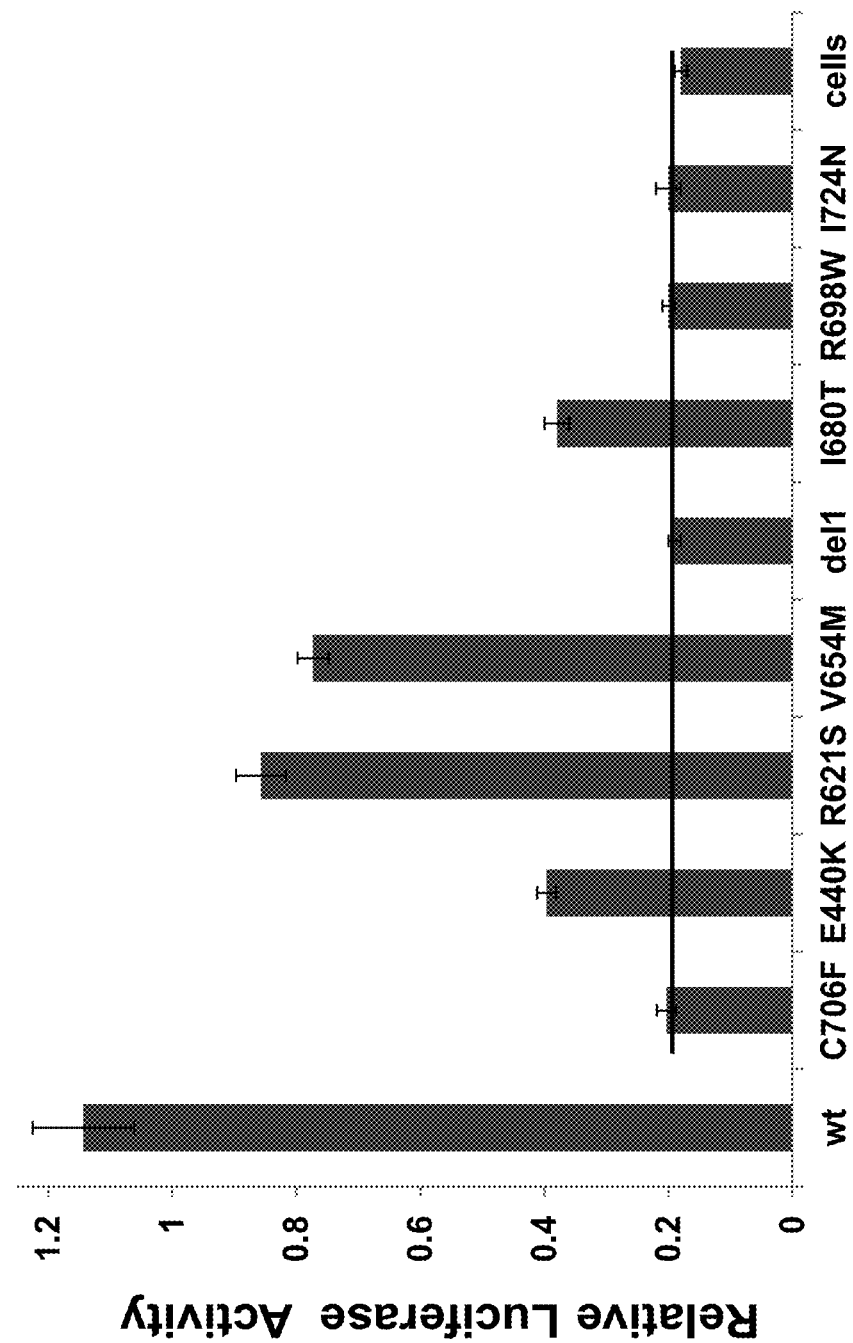
FIG. 21 shows Rb activity using unknown mutants from the COSMIC database.
Figure 22A:
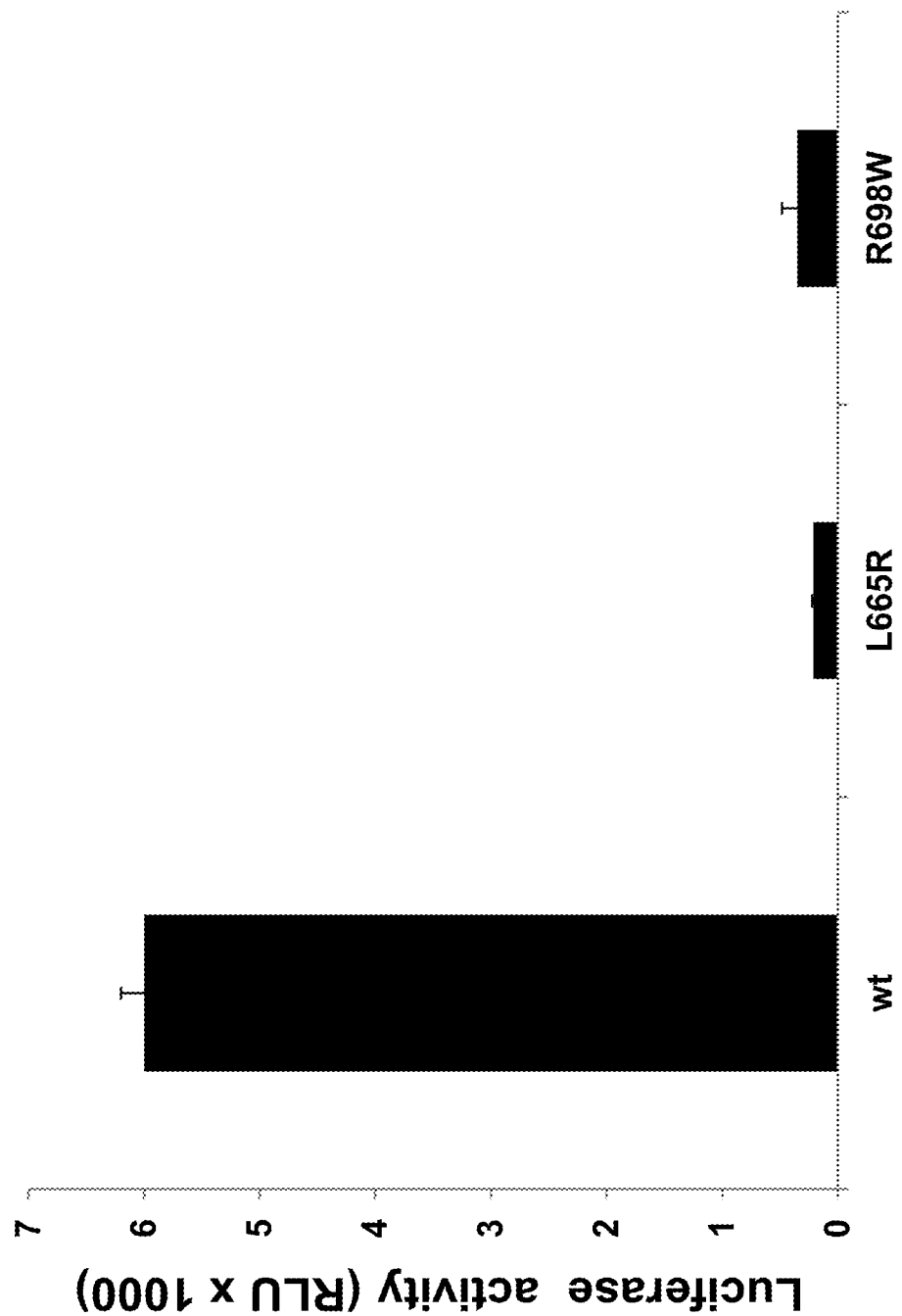
FIG. 22A shows Rb activity for two loss of function mutants from the COSMIC database.
Figure 22B:
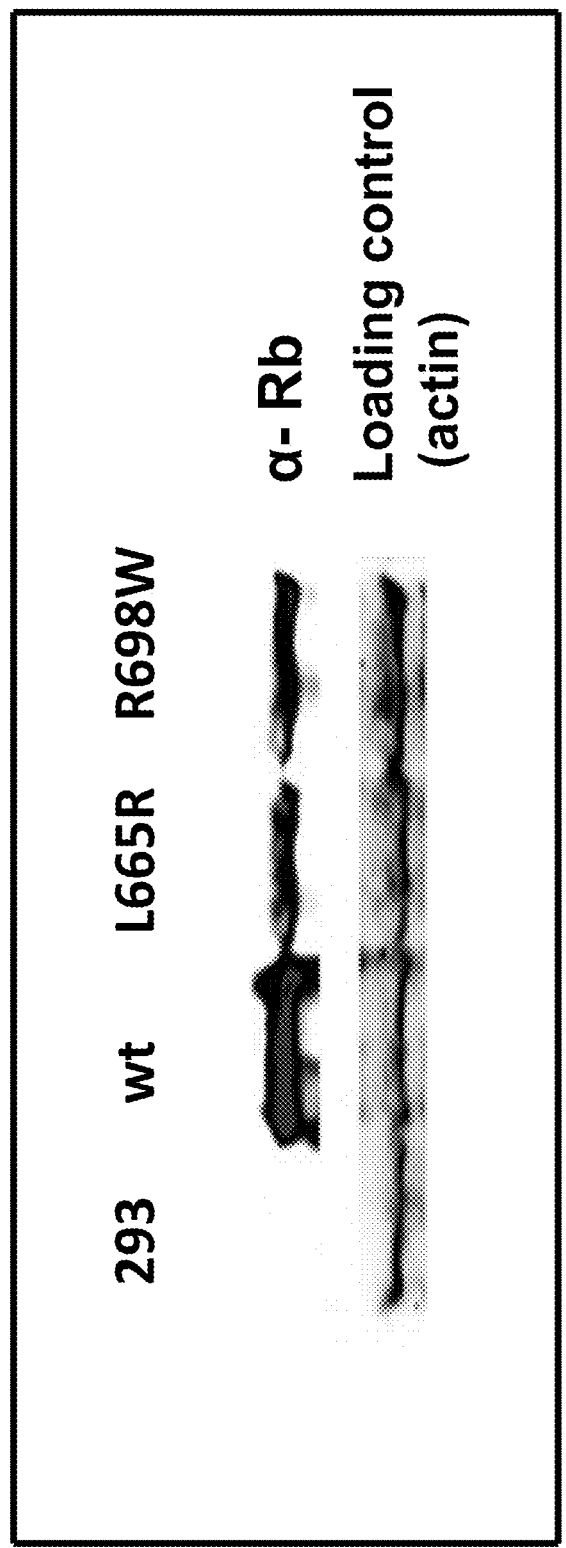
FIG. 22B shows confirmation of protein expression level of corresponding loss of function mutants (taken from COSMIC database) by western blot analysis.

Example 26 Rb Assay Validation by Using Known Null and Deletion Mutants, as Well as Unknown COSMIC Mutants Known null and out/in-frame deletion mutants disrupting E2F1 binding and unknown COSMIC mutants were created to examine the ability of the assay to detect variants in Rb that affect function. The primers are indicated in Table 10A and Table 10B. We transfected WT or mutated Rb using similar conditions as previously indicated (FIG. 20). Overexpression of WT LB-Rb exhibited a similarly observed increase in signal (FIG. 21). In addition, the null C706F and deletion (del1) mutants presented a signal close to zero as expected for loss of function mutants that disrupt E2F1 interaction. Some of the unknown COSMIC mutants demonstrated decreased or close to zero activity, other being as WT. Those unknown mutants with activity close to zero were checked by Western blot analysis and it was found that they had a decent protein expression level compared to the WT, but functionally they were inactive (FIGS. 22A and 22B). This confirmed that the assay was capable of determining the relative activity level of Rb mutants. The data is provided in Luminescence (RLU) of a single experiment with each condition performed in triplicate and represent average+SD.

A summary of all the Rb mutants checked to date is presented in Table 11.

TABLE 10A

Primers for site-directed mutagenesis of RB (Rb379-928) activity assay

| Rb mutant | Forward Primer | Reverse Primer |
|---|---|---|
| R661W | TATCGGCTAGCCTATCTCTGGCTA AATACACTTTGTGAA [SEQ. ID. NO: 132] | TTCACAAAGTGTATTTAGCCAGAGA TAGGCTAGCCGATA [SEQ. ID. NO: 133] |
| C706F | TTGGACCAAATTATGATGTTTTCC ATGTATGGCATATGC [SEQ. ID. NO: 134] | GCATATGCCATACATGGAAAACATC ATAATTTGGTCCAA [SEQ. ID. NO: 135] |
| E440K | GTGGGACAGGGTTGTGTCAAAAT TGGATCACAGCGATACA [SEQ. ID. NO: 136] | TGTATCGCTGTGATCCAATTTTGAC ACAACCCTGTCCCAC [SEQ. ID. NO: 137] |
| A488V | TTCATATGTCTTTATTGGTGTGCG CTCTTGAGGTTGTAAT [SEQ. ID. NO: 138] | ATTACAACCTCAAGAGCGCACACC AATAAAGACATATGAA [SEQ. ID. NO: 139] |
| R656W | TTTTATAAAAAAGTGTATTGGCTA GCCTATCTCCGGCTA [SEQ. ID. NO: 140] | TAGCCGGAGATAGGCTAGCCAATA CACTTTTTTATAAAA [SEQ. ID. NO: 141] |
| R621S | GAAAAAAGGTTCAACTACGAGTG TAAATTCTACTGCAAATG [SEQ. ID. NO: 142] | CATTTGCAGTAGAATTTACACTCGT AGTTGAACCTTTTTC [SEQ. ID. NO: 143] |
| V654M | TCACTGTTTTATAAAAAAATGTAT CGGCTAGCCTATCTC [SEQ. ID. NO: 144] | GAGATAGGCTAGCCGATACATTTTT TTATAAAACAGTGA [SEQ. ID. NO: 145] |
| L665R | ATCTCCGGCTAAATACACGTTGTG AACGCCTTCTGTCTG [SEQ. ID. NO: 146] | CAGACAGAAGGCGTTCACAACGTG TATTTAGCCGGAGAT [SEQ. ID. NO: 147] |
| R798Q | TTCCTAGTTCACCCTTACAGATTC CTGGAGGGAACATCT [SEQ. ID. NO: 148] | AGATGTTCCCTCCAGGAATCTGTAA GGGTGAACTAGGAA [SEQ. ID. NO: 149] |
| I680T | CAGAATTAGAACATATCACCTGG ACCCTTTTCCAGCACA [SEQ. ID. NO: 150] | TGTGCTGGAAAAGGGTCCAGGTGA TATGTTCTAATTCTG [SEQ. ID. NO: 151] |
| R698W | TATGAACTCATGAGAGACTGGCA TTTGGACCAAATTATG [SEQ. ID. NO: 152] | CATAATTTGGTCCAAATGCCAGTCT CTCATGAGTTCATA [SEQ. ID. NO: 153] |
| I724N | ACCTTAAATTCAAAATCAATGTAA CAGCATACAAGGATC [SEQ. ID. NO: 154] | GATCCTTGTATGCTGTTACATTGAT TTTGAATTTAAGGT [SEQ. ID. NO: 155] |
| R798W | TTCCTAGTTCACCCTTACAGATTC CTGGAGGGAACATCT [SEQ. ID. NO: 156] | AGATGTTCCCTCCAGGAATCTGTAA GGGTGAACTAGGAA [SEQ. ID. NO: 157] |
| I703del35 | GAGACAGGCATTTGGACCAAACA TTCAAACGTGTTTTGATC [SEQ. ID. NO: 158] | GATCAAAACACGTTTGAATGTTTGG TCCAAATGCCTGTCTC [SEQ. ID. NO: 159] |

TABLE 10A-continued

Primers for site-directed mutagenesis of RB (Rb379-928) activity assay

| Rb mutant | Forward Primer | Reverse Primer |
|---|---|---|
| R661del1 | GATCAAAACACGTTTGAATGTTTG GTCCAAATGCCTGTCTC [SEQ. ID. NO: 160] | CGTTCACAAAGTGTATTTAGAGATA GGCTAGCCGATACA [SEQ. ID. NO: 161] |

TABLE 10B

Primers for site-directed mutagenesis of full-length RB (Rb1-928) activity assay

| Rb mutant | Forward Primer | Reverse Primer |
|---|---|---|
| R147V | AGTACCAAAGTTGATAATGTTAT GTCAAGACTGTTGAAG [SEQ. ID. NO: 162] | CTTCAACAGTCTTGACATAACAT TATCAACTTTGGTACT [SEQ. ID. NO: 163] |
| V144S | ATTGATACCAGTACCAAAAGTGA TAATGCTATGTCAAGA [SEQ. ID. NO: 164] | TCTTGACATAGCATTATCACTTT TGGTACTGGTATCAAT [SEQ. ID. NO: 165] |
| G100A | AAGAAAAAGGAACTGTGGGCAA TCTGTATCTTTATTGCA [SEQ. ID. NO: 166] | TGCAATAAAGATACAGATTGCC CACAGTTCCTTTTTCTT [SEQ. ID. NO: 167] |
| G100R | AAGAAAAAGGAACTGTGGAGAA TCTGTATCTTTATTGCA [SEQ. ID. NO: 168] | TGCAATAAAGATACAGATTCTCC ACAGTTCCTTTTTCTT [SEQ. ID. NO: 169] |
| T373A | ATGTAATTCCTCCACACAGCCCA GTTAGGACTGTTATGA [SEQ. ID. NO: 170] | TCATAACAGTCCTAACTGGGCTG TGTGGAGGAATTACAT [SEQ. ID. NO: 171] |
| T373E | ATGTAATTCCTCCACACAATCCA GTTAGGACTGTTATGA [SEQ. ID. NO: 172] | TCATAACAGTCCTAACTGGATTG TGTGGAGGAATTACAT [SEQ. ID. NO: 173] |
| P374A | GTAATTCCTCCACACACTGCAGT TAGGACTGTTATGAAC [SEQ. ID. NO: 174] | GTTCATAACAGTCCTAACTGCAG TGTGTGGAGGAATTAC [SEQ. ID. NO: 175] |
| I185T | AGTTCGATATCTACTGAAACAAA TTCTGCATTGGTGCTA [SEQ. ID. NO: 176] | TAGCACCAATGCAGAATTTGTTT CAGTAGATATCGAACT [SEQ. ID. NO: 177] |
| S187T | ATATCTACTGAAATAAATACTGC ATTGGTGCTAAAAGTT [SEQ. ID. NO: 178] | AACTTTTAGCACCAATGCAGTAT TTATTTCAGTAGATAT [SEQ. ID. NO: 179] |
| E137D | CTTTAACTTACTAAAAGATATTG ATACCAGTACCAAAGT [SEQ. ID. NO: 180] | ACTTTGGTACTGGTATCAATATC TTTTAGTAAGTTAAAG [SEQ. ID. NO: 181] |

TABLE 11

Summary of the activity level of Rb mutants investigated

| Liter. ref | R661W | | | | | C706F | | |
|---|---|---|---|---|---|---|---|---|
| COSMIC database | R661W | I680T | A488V | R656W | R698W | C706F | E440K | L665R |
| count | 10 | 9 | 5 | 5 | 4 | 4 | 4 | 4 |
| Type of cancer | bladder colorect. lung | thyroid | bladder | colo- rectal mela- noma | medullo- blastoma | Small- cell lung | bladder | Small- cell lung |

TABLE 11-continued

Summary of the activity level of Rb mutants investigated

| Observed activity % (/wt) | N 5.2 | R 32 | R 51 | A 79 | N 6.4 | N 5.5 | R 47 | N 5 |
|---|---|---|---|---|---|---|---|---|
| Liter. ref | | | | | I703 del35 | | | |
| COSMIC database | R621S | V654M | R661fs* | I724N | I703del | R798W | R798Q | |
| count | 3 | 3 | 3 | 3 | 2 | 2 | 2 | |
| Type of cancer | lymphoma | glioblastoma | Small-cell lung | bladder | Ovarian prostatic | ovarian | colorectal | |
| Observed activity % (/wt) | A 124 | A 132 | N 0.8 | N 7.4 | N 8.6 | A 120 | A 92 | |

N—no activity
A—active as WT
R—reduced activity compared to the WT

Example 27 Next-Generation Sequencing to Interrogate Mutation of Tumor for p16 Activity Assay Since loss of p16 function is frequent in different types of cancer, knowing the gene mutations would be beneficial in cancer therapy. To survey the mutation status of the CDKN2A gene, whole exome sequencing was performed. Genomic DNA was extracted and used to prepare a library for next-generation sequencing. The identified mutations, which caused a change in amino acid sequence, were picked to examine their functional effect on the gene in a cell-based assay described herein. The patient gene carrying the identified mutation was constructed using PCR mediated overlapping extension in the format of linear expression cassette.

Example 28 Construction of Linear Expression Cassette of Human CDKN2A

In order to study the effect of unknown mutations in the human CDKN2A gene, a linear expression cassette was generated that contained a CMV promoter that controls CDKN2A expression and a coding sequence of CDKN2A followed by terminator and polyadenylation signal. Overlapping extension PCR was employed to construct the linear expression cassette using an expression plasmid of human CDKN2A as a PCR template. Under this method, the construction of linear expression cassette takes around 4-8 hours, while the traditional cloning method to generate expression plasmid takes around 2-4 days. Therefore, a patient gene in a linear expression cassette format is beneficial for the clinical diagnostic test because of its quick turn-around time.

Example 29 Generation of Linear Expression Cassette of WT and Mutated CDKN2A A cDNA plasmid encoding human CDKN2A gene was (GenScript) used as a PCR template to provide linear expression cassettes of WT or mutated forms of CDKN2A.

A linear expression cassette of human WT CDKN2A was generated by UF-CMV forward and BGH-UR reverse primers. The amplified products were gel-purified. The DNA concentration was quantitated by the optical density at 260 nm using Nanodrop.

Figure 23:
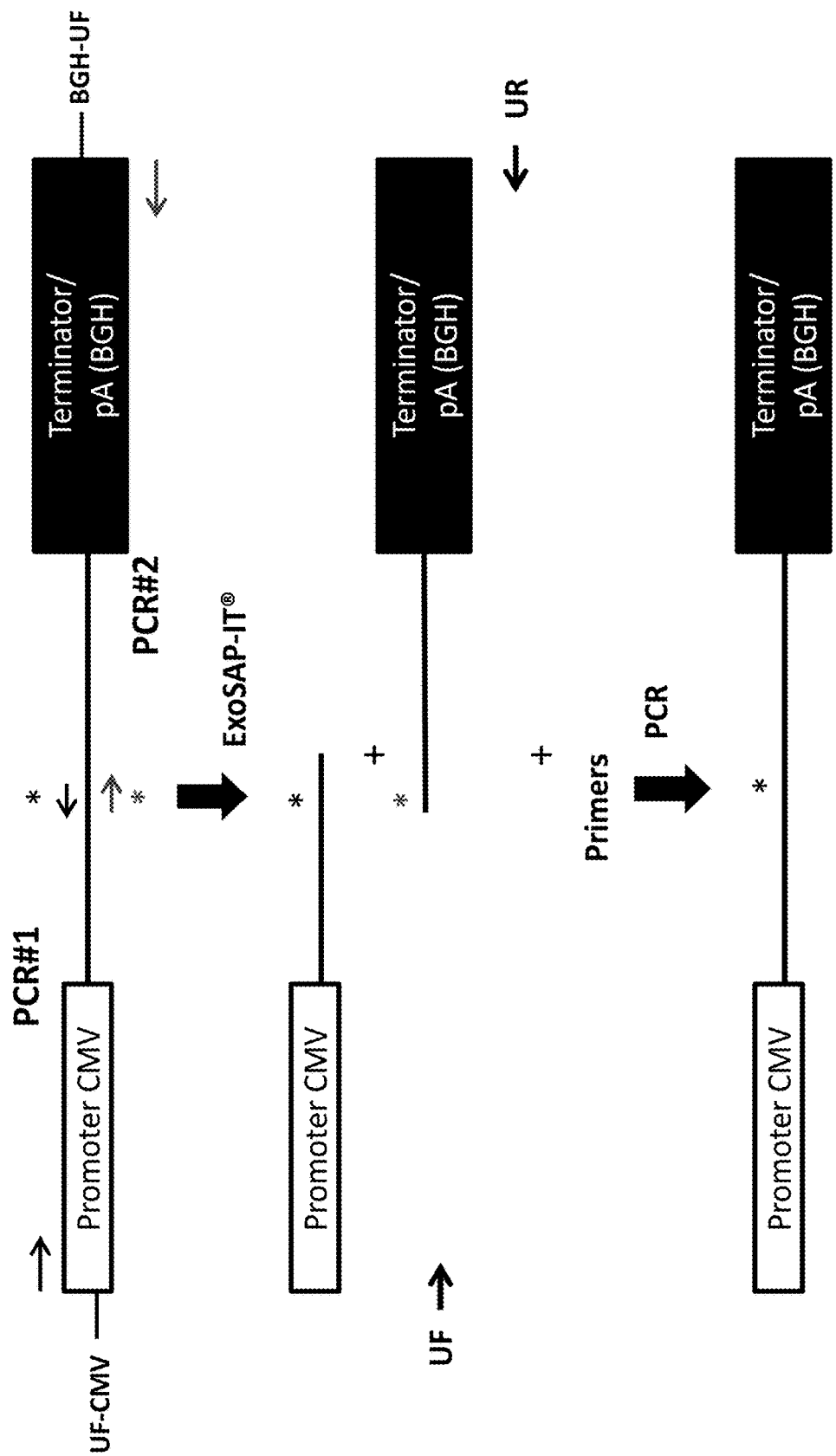
FIG. 23 shows a schematic representation of the PCR-mediated overlapping extension method for the p16 assay.

A linear expression cassette of mutated CDKN2A was generated by PCR mediated overlapping extension method. A pair of forward and reverse primers containing the targeted mutations was designed. The mutated codon was located in the middle of the primer flanked by 18-21 nucleotides in each side. Two separate PCRs, named as PRC #1 and PCR #2, were performed separately using UF-CMV forward and mutated reverse primers and mutated forward and BGH-UR primers were (FIG. 23). ExoSAP-IT® (Affymetrix) was used on the PCR products to remove unconsumed dNTPs and primers. The treated PCR products were mixed together followed by dilution with water. A second round of PCR analysis was performed using the diluted PCR mixture, and UF and UR primers (FIG. 23). The amplified products were gel-purified. The DNA concentration was quantitated by the optical density at 260 nm using Nanodrop. The targeted mutations were successfully incorporated in the CDKN2A gene during the PCR mediated overlapping extension method. The introduced mutations were confirmed by the DNA sequencing.

Example 30 Transfection Method

HEK293 cells are a specific cell line originally derived from human embryonic kidney cells grown in tissue culture. HEK293 cells have been widely used in cell biology research for many years because of their reliable growth and propensity for transfection. In general, there are two major types of transfection, forward and reverse.

A reverse transfection protocol was used as it reduced hands-on time for the end user. In this protocol, freshly passaged cells were added to the transfection complexes. In this scenario, cells were not adhered to the plate surface by the time they interacted with the transfection complexes.

Example 31 NanoBit Approach for p16 Activity Assay

Figure 24:
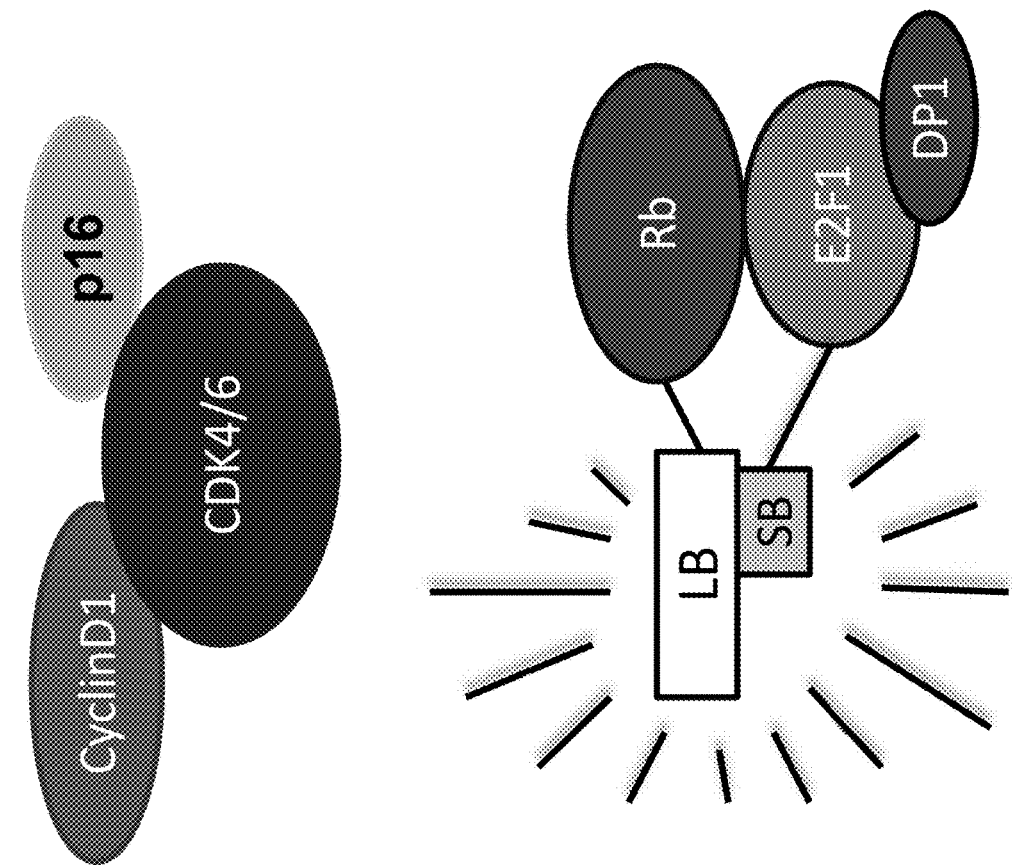
FIG. 24 shows a schematic representation of the NanoBit (Split Luciferase) design for the p16 assay.
Figure 24:
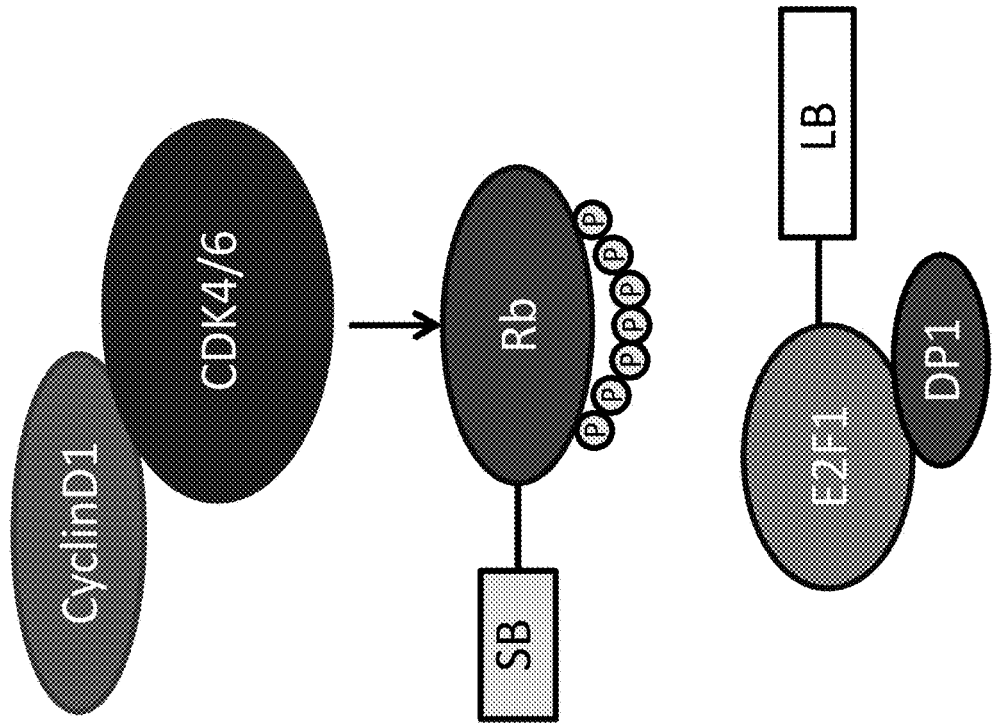

We developed an assay that could measure the interaction between Rb, E2F1 and Dp-1. When the Rb and E2F1 proteins are in close proximity or in complex, a light signal is observed. For the purpose of the assay, split-luciferase complementation was used to measure the interaction between Rb and E2F1, which served as a surrogate measure of CDK4/6 activity and the ability of CDK4/6 to respond to the natural inhibitor p16. The NanoBiT assay system by Promega (Madison, Wis.; Dixon et al., 2015, ACS Chem-Biol) was used in the split luciferase complementation design. FIG. 24 depicts a design of a signal system to measure p16 activity. Under basal conditions inside the cell, Rb is active and interacts with the E2F1/Dp-1 heterodimer. However, in the presence of the CDK4 or CDK6, Rb gets phosphorylated and released from the interacting complex. In the presence of the natural inhibitor p16, CDK4/6 is no longer available to phosphorylate Rb and thus promoting the Rb/E2F1-Dp-1 complex formation.

Example 32 p16 Activity Assay Validation

For the purpose of the current assay, the stable cell line #11 that we generated for the CDK activity assay was used and described above. HEK293 CDK DKO cells containing E2F1-Dp-1-LB was transiently transfected with CDK4/CDK6, CyclinD1, and SB-Rb. The transfected cells were then exposed to the natural inhibitor p16 (FIG. 25). When CDK4 or CDK6 is present, a decrease in activity was observed as Rb gets phosphorylated resulting in no Rb/E2F1-Dp-1 interaction. With treatment of p16, an increase in luminescence was observed, which is consistent with a decrease in CDK4/6 activity resulting in an increased interaction between SB-Rb and E2F1-Dp-1-LB. The data presented was a sample experiment where each condition was performed in triplicate and represented mean+SD.

Example 33 p16 Activity Assay Optimization

Figure 25A:
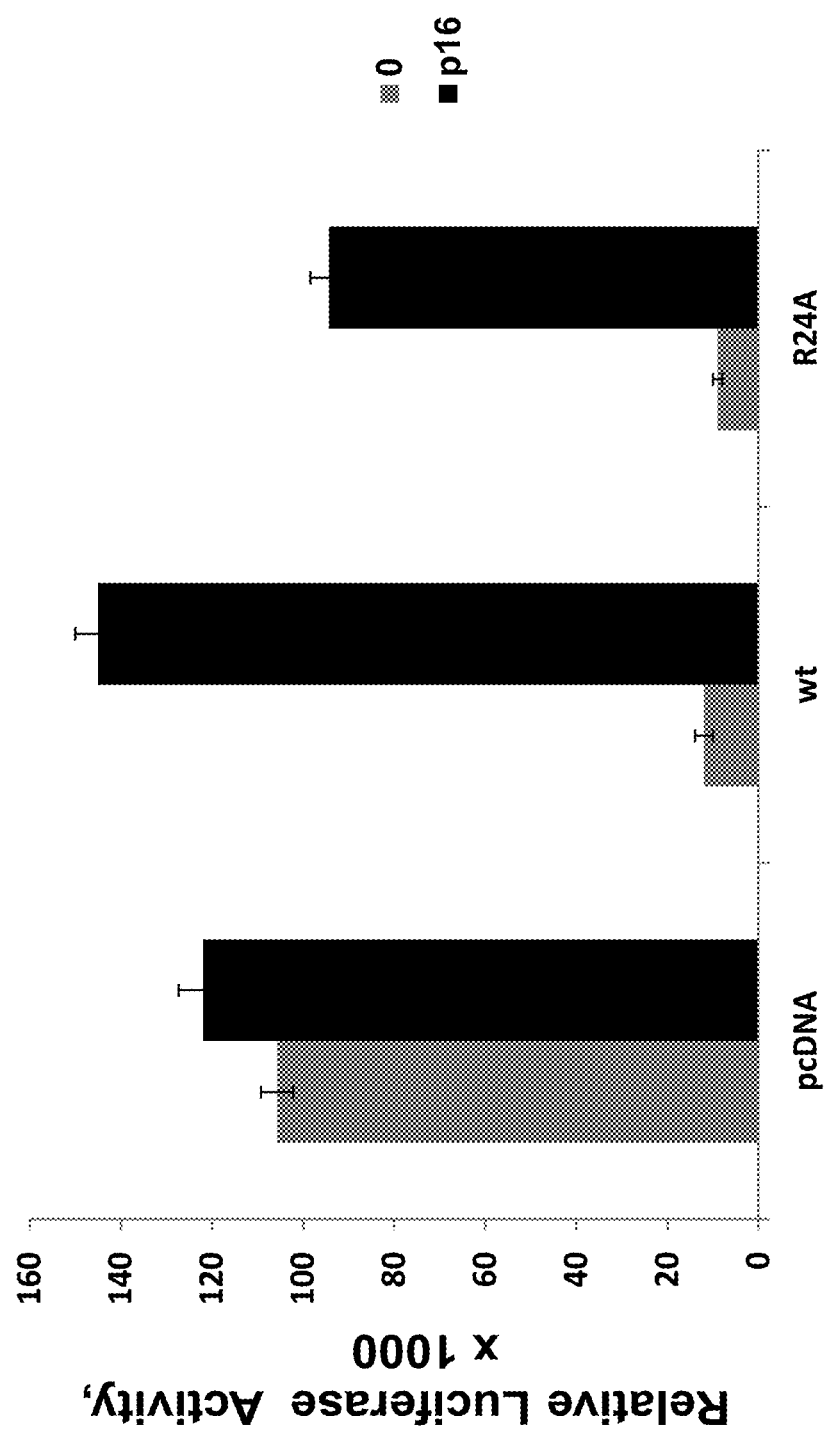
FIG. 25A shows inhibition of CDK4 by p16.
Figure 25B:
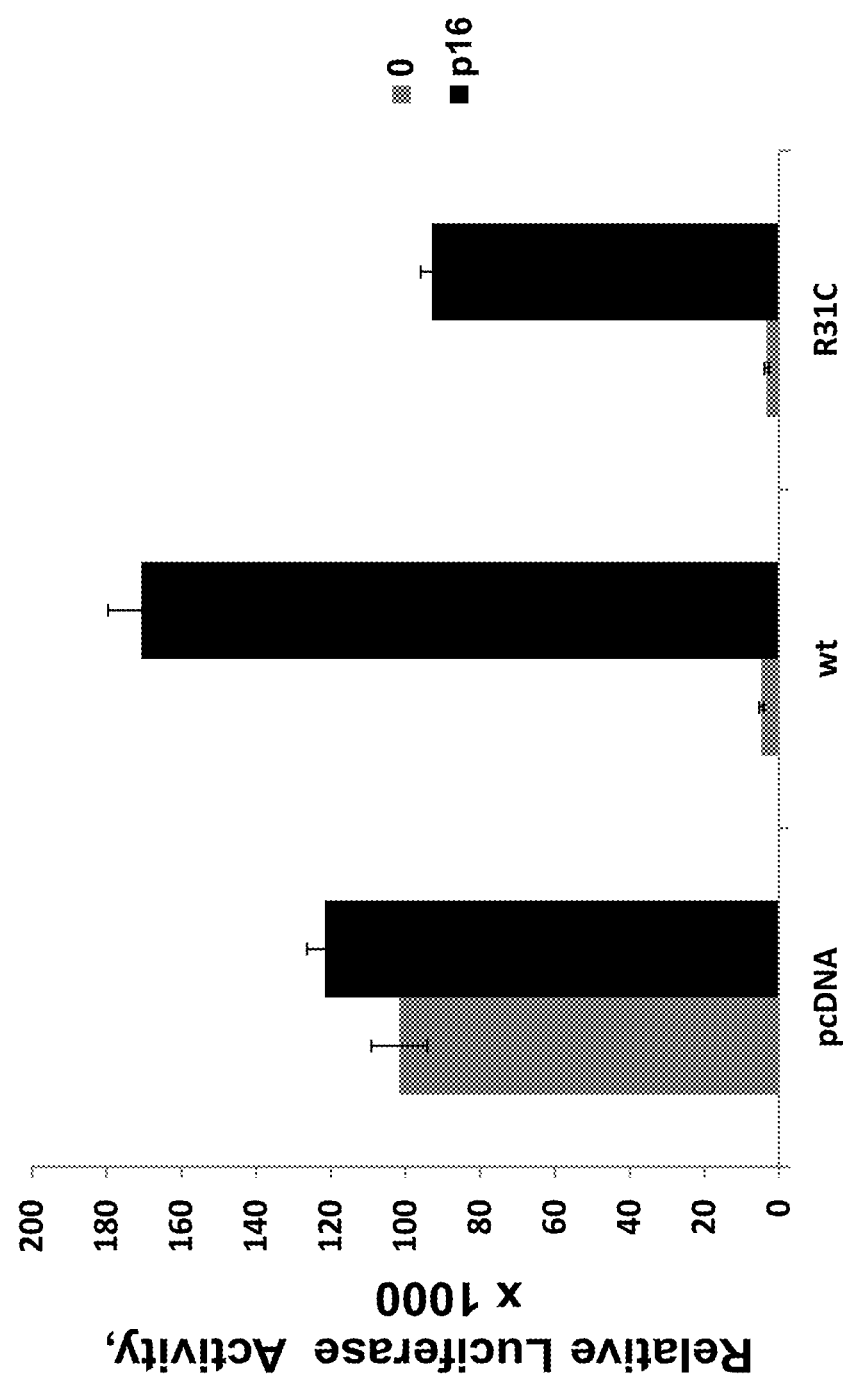
FIG. 25B shows inhibition of CDK6 by p16.

The conditions of the assay were optimized by using different p16 amounts and cell numbers (FIGS. 25A and 25B). Based on the data generated, it was decided that using $0.2 \times 10^6$ cells/ml and 10 ng of p16 would be preferable.

Figure 26A:
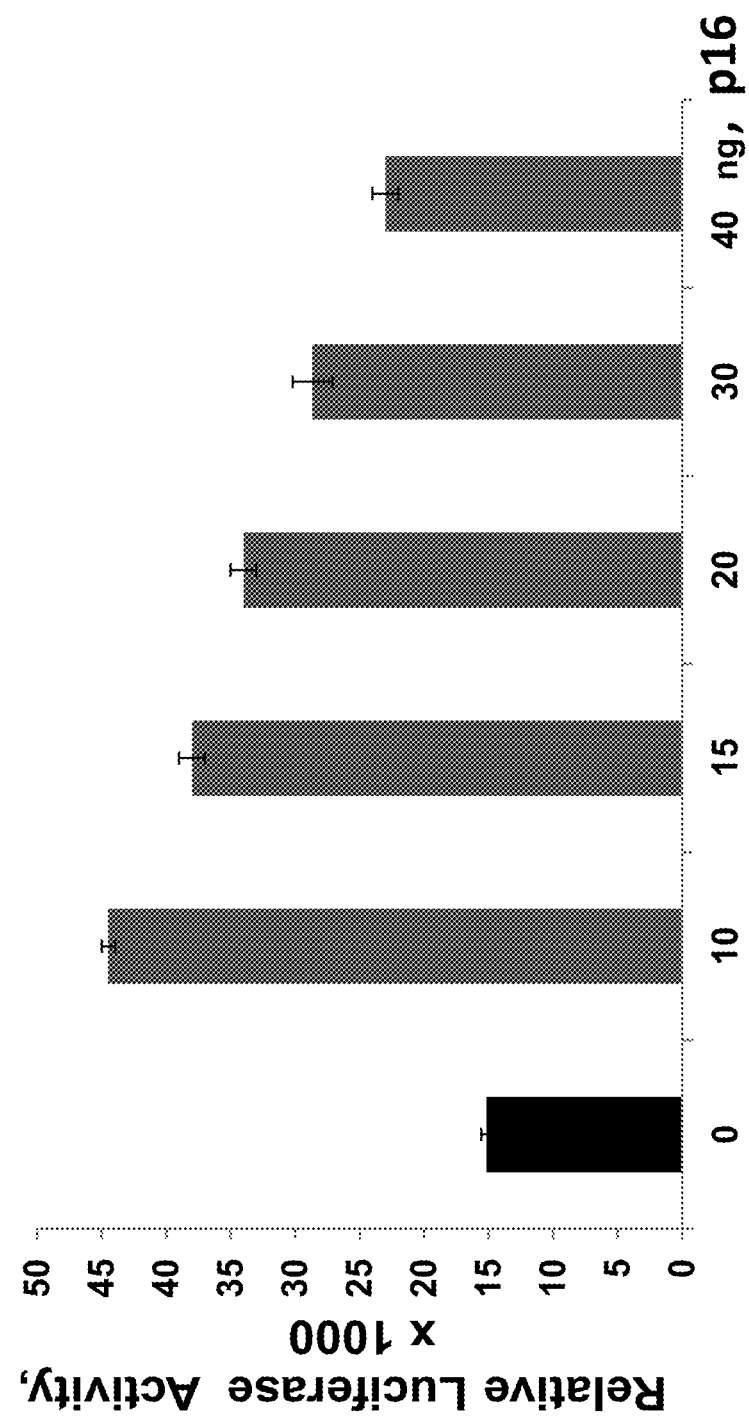
FIG. 26A shows optimization of the p16 activity assay using different amounts of p16 where CDK4:Cyclin D1:SB-Rb are 25 ng:25 ng:30 ng.
Figure 26B:
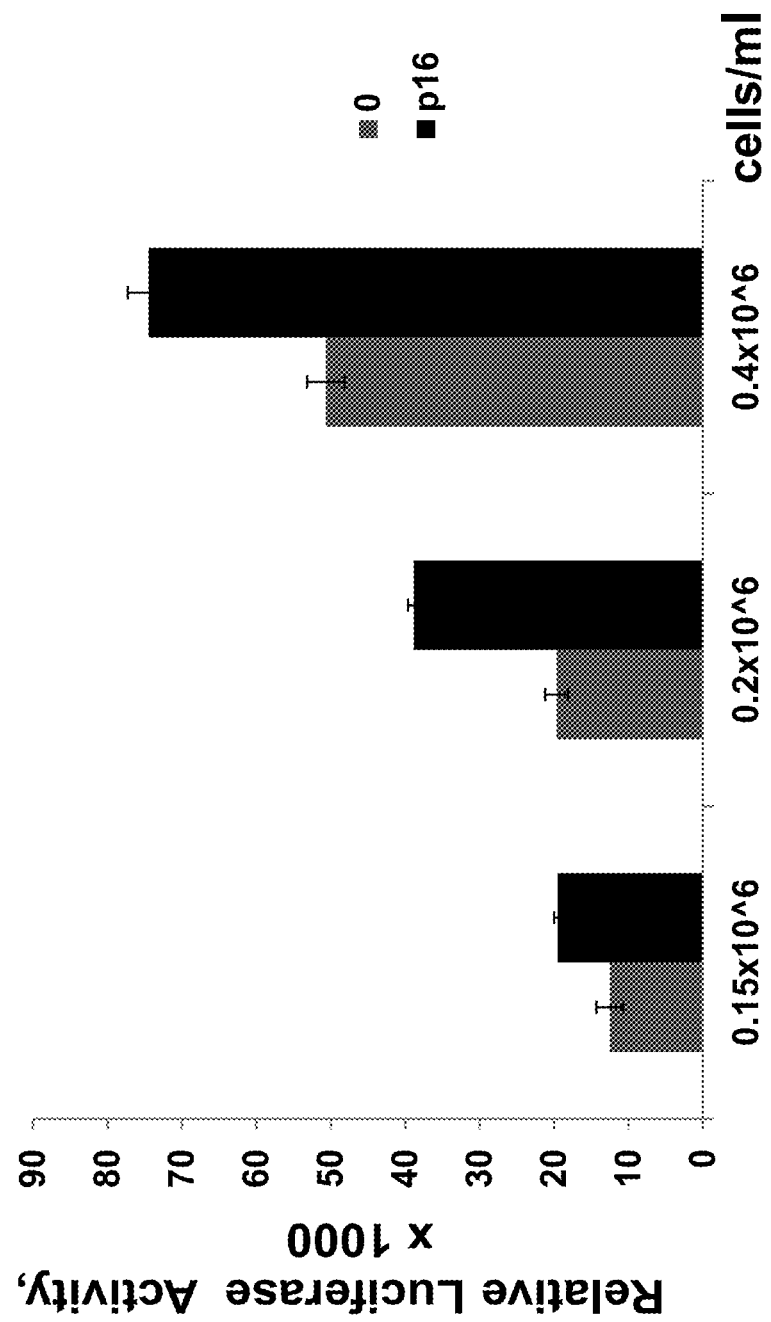
FIG. 26B shows optimization of the p16 activity assay using different cell amounts.
Figure 27:
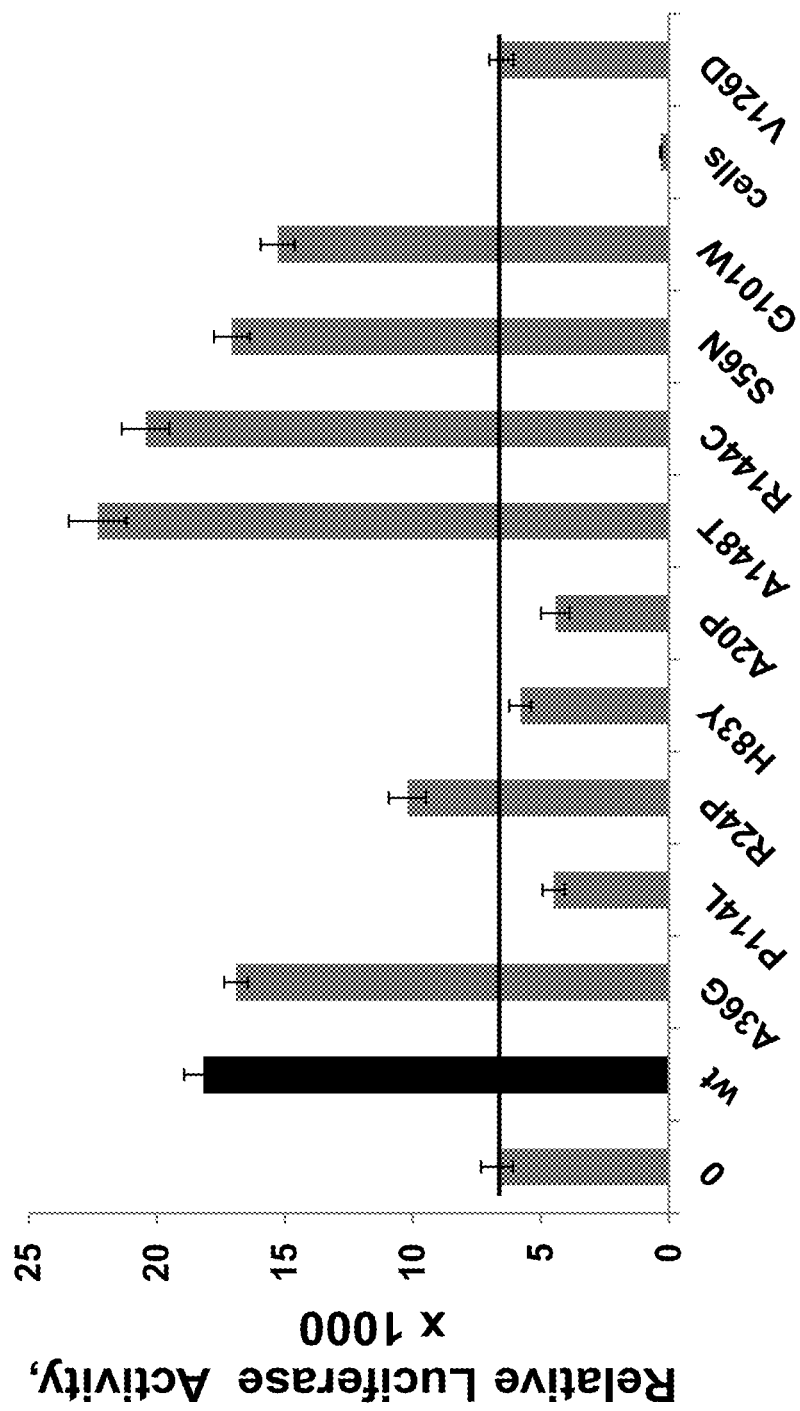
FIG. 27 shows validation of the p16 assay using different p16 mutants and CDK4.

Example 34 p16 Activity Assay Validation by Using Known Loss of Function and Unknown COSMIC Mutants To examine the ability of the assay to detect variants in CDKN2A that affect function, known loss of function mutants and unknown COSMIC mutants were created. The primers used are indicated in Table 12. Wild-type or mutated CDKN2A were prepared in a manner similar to that previously indicated. Over-expression of WT p16 exhibited the previously observed increase in signal (FIG. 26). In addition, the loss of function mutants (A20P, V126D, H83Y, and P114L) generated a signal close to the baseline as expected for loss of function mutants. Some of the COSMIC mutants with unreported functions generated decreased or close to the baseline activity, while other COSMIC mutants were as active as WT or higher. Therefore the p16 activity assay is capable of determining the relative activity level of p16 mutants. The data provided is in Luminescence (RLU) of a single experiment with each condition performed in triplicate and represent average+SD. Summary Table 13 reports p16 mutants tested.

TABLE 12

Primers for site-directed mutagenesis of CDKN2A

| p16 mutant | Forward Primer | Reverse Primer |
| --- | --- | --- |
| H83Y | ACTCTCACCCGACCCGTGTACGAC GCTGCCCGGGAGGGC [SEQ. ID. NO: 182] | GCCCTCCCGGGCAGCGTCGTACACG GGTCGGGTGAGAGT [SEQ. ID. NO: 183] |
| P114L | ATGCCTGGGGCCGTCTGCTCGTGG ACCTGGCTGAGGAGC [SEQ. ID. NO: 184] | GCTCCTCAGCCAGGTCCACGAGCAG ACGGCCCCAGGCAT [SEQ. ID. NO: 185] |
| A36G | GCGCTGCTGGAGGCGGGGGGGCTG CCCAACGCACCGAAT [SEQ. ID. NO: 186] | ATTCGGTGCGTTGGGCAGCCCCCCC GCCTCCAGCAGCGC [SEQ. ID. NO: 187] |
| V126D | GAGCTGGGCCATCGCGATGACGCA CGGTACCTGCGCGCG [SEQ. ID. NO: 188] | CGCGCGCAGGTACCGTGCGTCATCG CGATGGCCCAGCTC [SEQ. ID. NO: 189] |
| M53I | CGGAGGCCGATCCAGGTCATGATA ATGGGCAGCGCCCGAGTGGCG [SEQ. ID. NO: 190] | CGCCACTCGGGCGCTGCCCATTATC ATGACCTGGATCGGCCTCCG [SEQ. ID. NO: 191] |
| R24P | ACGGCCGCGGCCCGGGGTCCGGTA GAGGAGGTGCGGGCG [SEQ. ID. NO: 192] | CGCCCGCACCTCCTCTACCGGACCC CGGGCCGCGGCCGT [SEQ. ID. NO: 193] |
| A20P | GACTGGCTGGCCACGGCCCCGGCC CGGGGTCGGGTAGAG [SEQ. ID. NO: 194] | CTCTACCCGACCCCGGGCCGGGGCC GTGGCCAGCCAGTC [SEQ. ID. NO: 195] |
| A148T | CATGCCCGCATAGATGCCACGGAA GGTCCCTCAGACATC [SEQ. ID. NO: 196] | GATGTCTGAGGGACCTTCCGTGGCA TCTATGCGGGCATG [SEQ. ID. NO: 197] |
| S56N | CAGGTCATGATGATGGGCAACGCC CGAGTGGCGGAGCTG [SEQ. ID. NO: 198] | CAGCTCCGCCACTCGGGCGTTGCCC ATCATCATGACCTG [SEQ. ID. NO: 199] |
| S56I | ATCCAGGTCATGATGATGGGCATC GCCCGAGTGGCGGAGCTGCTG [SEQ. ID. NO: 200] | CAGCAGCTCCGCCACTCGGGCGATG CCCATCATCATGACCTGGAT [SEQ. ID. NO: 201] |

TABLE 12-continued

Primers for site-directed mutagenesis of CDKN2A

| p16 mutant | Forward Primer | Reverse Primer |
| --- | --- | --- |
| G101W | GTGGTGCTGCACCGGGCCTGGGCG CGGCTGGACGTGCGC [SEQ. ID. NO: 202] | GCGCACGTCCAGCCGCGCCCAGGC CCGGTGCAGCACCAC [SEQ. ID. NO: 203] |
| R144C | AGAGGCAGTAACCATGCCTGCATA GATGCCGCGGAAGGT [SEQ. ID. NO: 204] | ACCTTCCGCGGCATCTATGCAGGCA TGGTTACTGCCTCT [SEQ. ID. NO: 205] |
| D14G | AGCATGGAGCCTTCGGCTGGCTGG CTGGCCACGGCCGCG [SEQ. ID. NO: 206] | CGCGGCCGTGGCCAGCCAGCCAGC CGAAGGCTCCATGCT [SEQ. ID. NO: 207] |
| G35E | CGGGCGCTGCTGGAGGCGGAGGC GCTGCCCAACGCACCG [SEQ. ID. NO: 208] | CGGTGCGTTGGGCAGCGCCTCCGCC TCCAGCAGCGCCCG [SEQ. ID. NO: 209] |
| D108N | GCGCGGCTGGACGTGCGCAATGCC TGGGGCCGTCTGCCC [SEQ. ID. NO: 210] | GGGCAGACGGCCCCAGGCATTGCG CACGTCCAGCCGCGC [SEQ. ID. NO: 211] |

TABLE 13

Summary table of all CDKN2A mutants checked

| p16 | A20P | R24P | M53I | V126D | H83Y | P114L | A148T |
| --- | --- | --- | --- | --- | --- | --- | --- |
| Cosmic count | 3 | 6 | 3 | 2 | 58 | 46 | 3 |
| Type of cancer | melanoma bladder prostate | osteo-sarcoma glioblas-toma leukemia | thyroid carcinoma melanoma | pancreatic melanoma | squamous carcinoma pancreatic lung cancer breast cancer melanoma bladder cancer leukemia | melanoma skin cancer bladder cancer squamous cell carcinoma lung cancer | melanoma pancreatic kidney carcinoma |
| Literature reported function | Loss of function | Loss of function | Loss of function | Loss of function | Loss of function | Loss of function | Normal |
| Observed function | Loss of function | Loss of function | Loss of function | Loss of function | Loss of function | Loss of function | Normal |

| p16 | S56N | D14G | G35E | D108N | A36G | G101W | R144C |
| --- | --- | --- | --- | --- | --- | --- | --- |
| Cosmic count | 1 | 1 | 3 | 10 | 10 | 4 | 0 |
| Type of cancer | ampullary carcinoma | squamous cell carcinoma | melanoma | bladder squamous cell carcinoma colorectal endometrial breast cancer lung squamous carcinoma biliary tract cancer head and neck squamous cell carcinoma | skin melanoma head, neck cancer kidney carcinoma | squamous cell carcinoma liver cancer | |

TABLE 13-continued

Summary table of all CDKN2A mutants checked

| Literature reported function | Not reported | Not reported | Not reported | Not reported | Not reported | Loss of function | Normal |
|---|---|---|---|---|---|---|---|
| Observed function | Normal | Normal | Loss of function | Normal | Normal | Reduced | Normal |

Example 35 p16 Activity Assay Validation Using Different CDK4 and CDK6 Mutants

Figure 28:
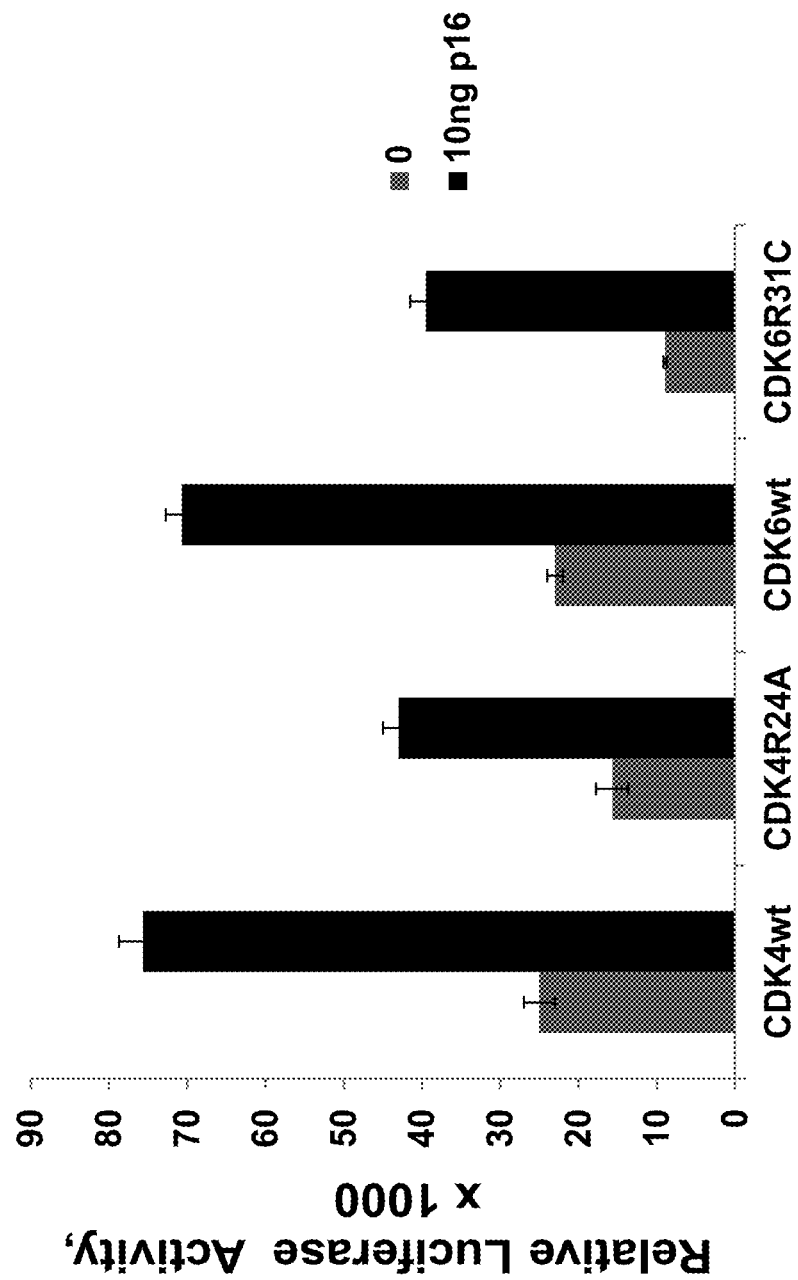
FIG. 28 shows the validation of the p16 assay utilizing hyperactive CDK6 and CDK6 mutants and their binding to p16.
Figure 29:
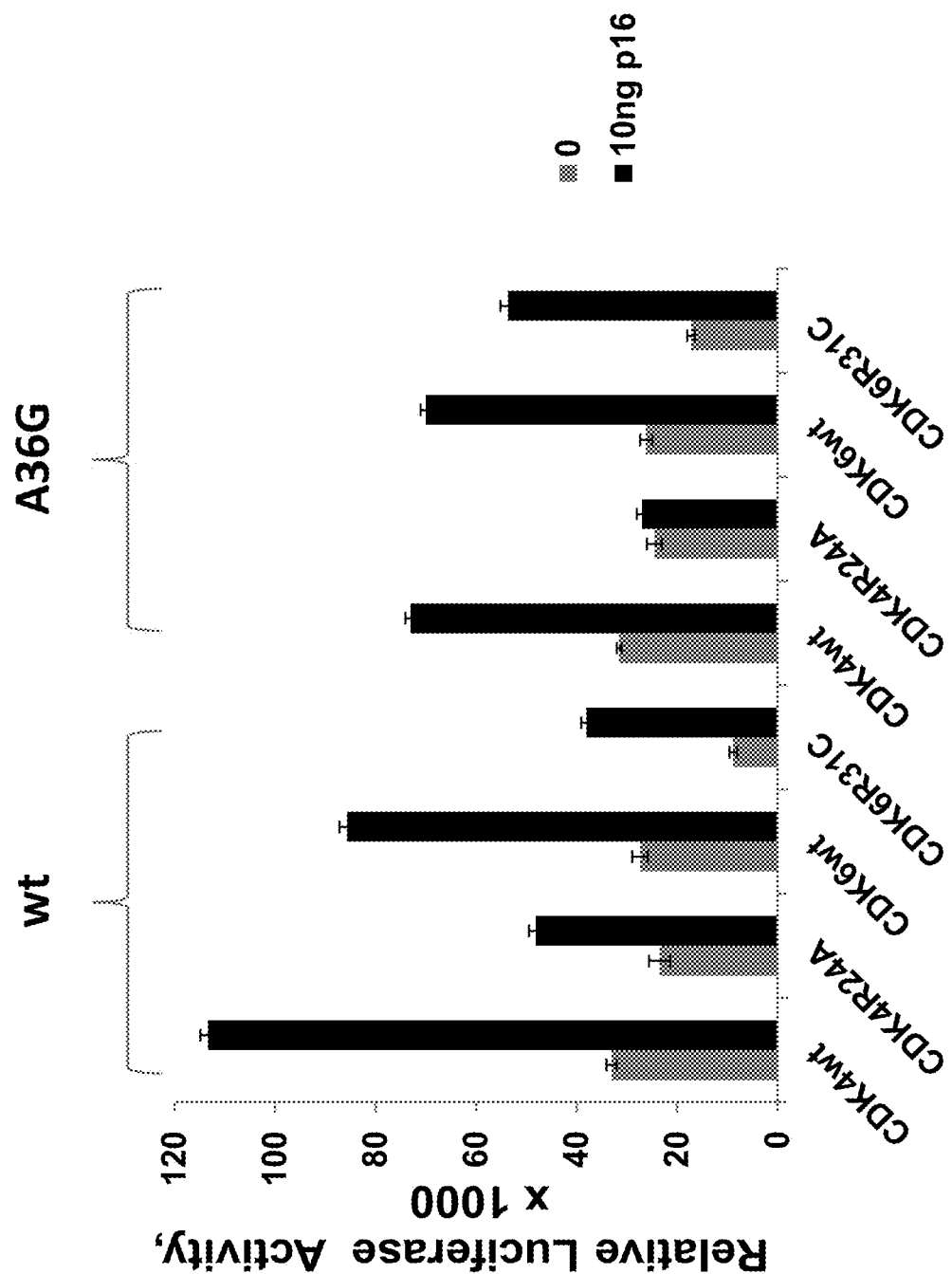
FIG. 29 shows the validation of the p16 assay using A36G p16 mutant binding to CDK4 and CDK6.

In addition to check functional state of p16 mutants, p16 activity assay can be used to look at p16 inhibition response of different CDK4 and CDK6 mutants. Different response of WT CDK4 and CDK6 and hyperactive mutants of CDK4 (R24A) and CDK6 (R31C) is shown on FIG. 28. As expected for hyperactive mutants (due to their less binding to natural inhibitor p16) a decreased level of luminescence was observed, consistent with a decrease in CDK binding to p16. The p16 activity assay is so sensitive and specific that hyperactive CDK4 and CDK6 mutants can show different response to mutant p16. For example, p16 A36G mutant being normal functionally showed different inhibition for R24A CDK4 mutant compared to the WT (FIG. 29).

What is claimed is:

1. A method of determining the activity of a Rb variant in a cell, comprising the steps of:
    a. providing a mammalian cell, said cell comprising a stably integrated first construct, wherein said first construct comprises a first cDNA encoding E2F1 protein which is linked to a first portion of a luciferase gene, and a second cDNA encoding Dp-1 protein;
    b. preparing a linear third cDNA of a Rb variant, wherein said Rb variant contains at least one mutation as compared to wild-type Rb, and said third cDNA is linked to a second portion of a luciferase gene to form a second construct, wherein when said first construct is in close proximity with said second construct a complex is formed that emits light;
    c. transfecting said second construct into said mammalian cell; and
    d. determining the activity of said Rb variant by measuring any generated light emission, wherein an increase in light emission relative to a control mammalian cell is indicative of said Rb variant activity.

2. A method of determining the activity of a p16 variant in a cell comprising the steps of:
    a. providing a mammalian cell, said cell having a knockout of endogenous CDK4 and endogenous CDK6, and a first construct stably integrated into said mammalian cell comprising a first cDNA encoding E2F1 protein linked to Dp-1 protein and a first portion of a luciferase gene at its C-terminus;
    b. preparing a second construct comprising a second cDNA encoding Rb protein which is linked to a second portion of a luciferase gene at its N-terminus, wherein when said first construct is in close proximity with said second construct a complex is formed that emits light;
    c. preparing a third cDNA encoding Cyclin D1 protein and a fourth cDNA encoding CDK4 protein or CDK6 protein;
    d. preparing a fifth cDNA of a CDKN2A variant, said CDKN2A variant having at least one mutation as compared to wild-type CDKN2A;
    e. preparing a transfection complex, said transfection complex comprising said second construct, said third cDNA, said fourth cDNA, and said fifth cDNA;
    f. transfecting said transfection complex into said mammalian cell, wherein said transfection is transient; and
    g. determining the activity of said p16 variant by measuring any generated light emission, wherein an increase in light emission relative to a mammalian cell control is indicative of said p16 variant activity.

3. A method of determining the sensitivity of a CDK4 variant or a CDK6 variant to p16 in a cell, comprising the steps of:
    a. providing a mammalian cell, said cell having a knockout of endogenous CDK4 and endogenous CDK6, and a first construct stably integrated into said cell, said first construct comprising a first cDNA encoding E2F1 protein linked to Dp-1 protein, wherein said Dp-1 protein is linked to a first portion of a luciferase gene at its C-terminus;
    b. preparing a second cDNA of a CDK4 or CDK6 variant from a patient, said CDK4 variant or CDK6 variant containing at least one mutation as compared to wild-type CDK4 or wild-type CDK6;
    c. preparing a second construct comprising a third cDNA encoding Rb protein which is linked to a second portion of a luciferase gene at its N-terminus, wherein when said first construct is in close proximity with said second construct a complex is formed that emits light;
    d. preparing a fourth cDNA encoding Cyclin D1 protein;
    e. preparing a fifth cDNA of wild-type CDKN2A;
    f. preparing a transfection complex comprising said second construct, said third cDNA, said fourth cDNA, and said fifth cDNA;
    g. transfecting said transfection complex into said mammalian cell, wherein said transfection is transient; and
    h. determining whether said CDK4 or CDK6 variant is sensitive to p16 by measuring any generated light emission, wherein an increase in light emission relative to a mammalian cell control is indicative of said CDK4 or CDK6 variant being sensitive to p16.

* * * * *